United States Patent [19]

Harman

[11] Patent Number: 5,406,479
[45] Date of Patent: Apr. 11, 1995

[54] METHOD FOR REBINNING AND FOR CORRECTING CONE BEAM ERROR IN A FAN BEAM COMPUTED TOMOGRAPHIC SCANNER SYSTEM

[75] Inventor: Jonathan W. Harman, So. San Francisco, Calif.

[73] Assignee: Imatron, Inc., So. San Francisco, Calif.

[21] Appl. No.: 170,057

[22] Filed: Dec. 20, 1993

[51] Int. Cl.$^6$ .............................................. G06F 15/00
[52] U.S. Cl. ........................ 364/413.17; 364/413.21; 382/6
[58] Field of Search .................. 364/413.17, 413.21, 364/413.15, 413.20; 382/6, 54; 250/396; 128/653 A, 653 R

[56] References Cited

U.S. PATENT DOCUMENTS

| | | | |
|---|---|---|---|
| 4,352,021 | 9/1982 | Boyd et al. | 378/12 |
| 4,521,900 | 6/1985 | Rand | 378/137 |
| 4,812,983 | 3/1989 | Gullberg et al. | 364/413.17 |
| 5,065,436 | 11/1991 | Matsumura | 382/6 |
| 5,170,439 | 12/1992 | Zeng et al. | 382/6 |
| 5,187,659 | 2/1993 | Eberhard et al. | 364/413.15 |
| 5,293,312 | 3/1994 | Waggener | 364/413.21 |
| 5,307,264 | 4/1994 | Waggener et al. | 364/413.21 |

OTHER PUBLICATIONS

Lin et al, "Parallel algorithms and architectures for DSP applications", 1991 pp. 113-127, Kluwer Academic Publishers, Dordrecht, Netherlands.
O'Sullivan, "A fast sinc gridding algorithm for Fourier inversion in Computer tomography", IEEE Transactions on Medical Imaging, vol. MI-4, No. 4, pp. 200-207.
"Selection of a Convolution Function for Fourier Inversion Using Gridding", by Jackson, Meyer et al, IEEE Transactions on Medical Imaging, vol. 10, No. 3, Sep. 1991, pp. 473-478.
"Backprojection by Unsampled Fourier Series Expansion and Interpolated FET", by Tabei and Ueda, IEEE Transactions on Image Processing, vol. 1, No. 1, Jan. 1992, pp. 77-87.

*Primary Examiner*—Gail O. Hayes
*Assistant Examiner*—Frantzy Poinvil
*Attorney, Agent, or Firm*—Flehr, Hohbach, Test, Albritton & Herbert

[57] ABSTRACT

A method of reconstructing data acquired on a fan beam CT system first rebins the data to parallel beam format using limited angle weighting that fold-over redundant data by adding corner rays of one scan to the center rays of another scan. For each view, now parallel beam data are filtered with a parallel beam kernel, and transformed. The transform is replicated, and multiplied by an interpolation filter. Next, the replicated, multiplied transform is convolved with the gridding function, and added into the Fourier image at an angle corresponding to the view angle. In the case of an n-scan cone beam correction a two-dimensional weighting function is calculated for each view giving the view's contribution to each pixel in the image. Multiplication by this weighting function is accomplished by convolution of the transform of the weighting function with the above transformed view. These steps are repeated for all views, whereafter the two-dimensional inverse Fourier transform is taken to get a preliminary image. The center portion of the preliminary image is then extracted and multiplied by the inverse of the gridding function to get the desired reconstructed image. The image, which is substantially free of cone beam error, is built-up by summing for each view the backprojection of the view times that view's weighting function. Preferably the gridding function is a Kaiser-Bessel function, whose values are pre-calculated and stored in a look-up table.

6 Claims, 10 Drawing Sheets

METHOD FOR REBINNING AND FOR CORRECTING CONE BEAM ERROR IN A FAN BEAM COMPUTED TOMOGRAPHIC SCANNER SYSTEM

FIELD OF THE INVENTION

The present invention relates generally to computed tomography X-ray systems, and more particularly to a method for rebinning fan beam data, and for correcting cone beam error in a fan beam computed tomographic scanner system using a parallel beam reconstruction algorithm.

BACKGROUND OF THE INVENTION

Early in this century, the Austrian mathematician J. Radon demonstrated that a two-dimensional slice of a three-dimensional object may be reproduced from the set of all of its projections. Computed tomography ("CT") X-ray systems generate a set of X-ray beam projections through an object to be examined. The resultant detected X-ray data are computer processed to reconstruct a tomographic image-slice of the object.

CT systems subject the object under examination to one or more pencil-like X-ray beams from all possible directions. The X-ray data may be generated in fan beam format (as is the case for the present invention), or in parallel beam format. In a fan beam system, the X-rays radiate from a source and are collected in a fan. By contrast, in a parallel beam system the X-rays are all parallel within a view. In either system, a view is one projection of the object onto the detectors, and a scan is a collection of all of the views.

In a fan beam scanning electron beam system such as described in U.S. Pat. No. 4,521,900 to Rand, or U.S. Pat. No. 4,352,021 to Boyd, an electron beam is produced by an electron gun and is accelerated downstream along the z-axis of an evacuated chamber. Further downstream a beam optical system deflects the electron beam into a scanning path, typically about 210°. The deflected beam is then focussed upon a suitable target, typically a large arc of tungsten material, which produces a fan beam of X-rays.

The emitted X-rays penetrate an object (e.g., a patient) that is disposed along the z-axis and lying within a so-called reconstruction circle. X-ray beams passing through the object are attenuated by various amounts, depending upon the nature of the object traversed (e.g., bone, tissue, metal). One or more X-ray detectors, disposed on the far side of the object, receive these beams and provide signals proportional to the strength of the incoming X-rays.

Typically the output data from the detectors are processed using a filtered back-projection algorithm. Detector data representing the object scanned from many directions are arranged to produce image profiles for each scan direction. Since the X-rayed object is not homogeneous, these profiles will vary in intensity with the amount of radiation detected by the various detectors on the various scans. The rays from the various projections are then superimposed, or back-projected, to produce a computed tomographic image of the original object. The thus processed data are used to produce a reconstructed image of a slice of the object, which image may be displayed on a video monitor.

Systems similar to what is described in the above patents to Rand or Boyd are manufactured by Imatron, Inc., located in South San Francisco, Calif. These systems are termed "short scan" because the views used for reconstructing an object image cover 180° plus the fan beam angle (about 30°), e.g., about 210° total, rather than a full 360°.

In these systems, the X-ray detectors also span 180° plus the fan angle, and define a first plane that is orthogonal to the z-axis. The source of the X-rays scans or travels within a second plane, also orthogonal to the z-axis, but not necessarily coincident with the first plane. However in scanning electron beam fourth-generation CT systems, the large evacuated chamber and distance separating the target and detectors, can result in these two planes being offset by a dimension $\Delta z$, that may be in the range of a cm or so. Thus, while ideally reconstruction creates an image in a plane perpendicular to the z-axis using views acquired within that plane, due to the cone angle, each acquired view is not perpendicular to the z-axis.

This $\Delta z$ offset causes the X-ray beam to somewhat misalign and sweep out a shallow cone during a scan, and unless the cone beam geometry is accounted for during reconstruction, cone beam error results. Unless corrected, cone beam error produces a reconstructed image that includes unwanted cone beam artifacts that appear as streaks in the reconstructed, displayed image.

To display a reconstructed image of the object slice requires computer intensive reconstruction techniques. Computed tomography is the method of determining the cross section of an X-rayed object by using projections of the object from many different angles. A mathematical reconstruction algorithm is used to reconstruct the object's cross section from the fan beam projections, represented by the detected data.

Computed tomography reconstruction algorithms exist for fan beam data and for parallel beam data. Such fan beam algorithms are described, for example, in "Principles of Computerized Tomographic Imaging" by Avinash Kak and Malcolm Slaney, IEEE Press, N.Y. (1987). The reference "Optimal Short-Scan Convolution Reconstruction for Fan Beam CT" by Dennis Parker, *Med Phys.*, 9:254–257 (1982), describes weights used in short scan fan beam algorithms.

In general, attempting to process fan beam data in real time, e.g., a few seconds or less, requires using custom designed computer equipment. This results because fan beam reconstruction techniques involve spatial domain backprojection algorithms, which are extremely computer intensive in that many computational operations are required. Thus, generally, fan beam reconstruction is less desirable than parallel beam reconstruction.

By contrast, there exist parallel beam reconstruction techniques that use transform domain algorithms that execute rapidly using conventional computer array processors. Relying upon customized backprojection equipment is not desirable because a modification of the CT system can require modification of the backprojection equipment, a costly and time consuming process. Further, relatively few companies produce custom designed backprojectors, and from an engineering and business standpoint, it is undesirable for the CT system manufacturer to rely on sole-source equipment such as backprojectors.

It is therefore preferred that parallel beam reconstruction techniques be practiced, for reasons of speed and for ease of implementation using commercially available array processors. Among parallel beam reconstruction techniques are the so-called gridding Fourier inversion algorithms, wherein each view is transformed, convolved with a gridding function, and then added into a two-dimensional Fourier transform of the image. If such method is done for but one view, the resulting image equals the backprojection of that view, using a filtered backprojection algorithm. See, for example, J. D. O'Sullivan, "A Fast Sinc Function Gridding Algorithm for Fourier Inversion in Computer Tomography" IEEE Trans on Medical Imaging, vol. MI-4, no. 4, pp 200–207, December, 1985, and J. Jackson, C. Meyer, D. Nishimura, A. Macovski, "Selection of a Convolution Function for Fourier Inversion Using Gridding" IEEE Trans on Medical Imaging, vol MI-10, no. 3, pp 473–478. Another parallel beam algorithm was disclosed in M. Tabei, M. Ueda, "Backprojection by Unsampled Fourier Series Expansion and Interpolated FFT", IEEE Trans on Image Proc., vol. 1, No. 1, pp 77–87, a gridding technique, where a Gaussian gridding function was used, as such functions may be calculated rapidly on the fly.

While Tabei-type parallel beam reconstruction algorithms have many advantages, they cannot be used with fan beam data. Fortunately, however, so-called rebinning techniques are known for transforming or converting fan beam data to parallel beam data, whereupon fast parallel beam algorithms such as that disclosed by Tabei may be used for reconstruction. One such rebinning algorithm is described by Gabor Herman, in Image Reconstructions from Projections, 1980 Academic Press, N.Y.

However, even if fan beam data are suitably rebinned for reconstruction using a fast parallel beam reconstruction algorithm, the $\Delta z$ offset noted above produces a so-called cone beam artifact in the reconstructed image. Further, conventional short scan fan beam to parallel beam rebinning techniques discard redundant data appearing at the top and bottom of the fan beam sinogram. This practice is undesirable because, in medical applications, the redundant regions of the sinogram represent data for which the patient was irradiated. Further, discarding the redundant data reduces the signal to noise ratio.

What is needed is a method of retaining redundant data in a fan beam sinogram during a rebinning operation. Preferably such modified rebinning method would make the resultant parallel beam data suitable for correcting cone beam error.

Further, there is a need for a modified Tabei-type algorithm capable of correcting for cone beam error, and capable of permitting imaging zooming on the displayed image from a point other than the center of the image. What is needed is a reconstruction method that permits a zoom view of the reconstructed image, from any point on the image.

The present invention describes such a modified rebinning procedure, and a modified Tabei-type parallel beam reconstruction procedure, whereby cone beam error is substantially reduced. Further, the present invention provides non-center zooming of the reconstructed displayed image. Further, the present invention may be implemented with conventional array processors, and is faster executing than the Tabei reconstruction method.

SUMMARY OF THE INVENTION

The present invention uses spatial techniques and transform techniques to correct for cone beam error in a fan beam CT system. Two or more CT scans, each separated by a small distance in the z-direction, are used to produce one reconstructed image with substantially reduced cone beam errors. A rebinning step is used to transform the fan beam views into parallel beam format, which format permits rapid reconstruction using a modified parallel beam reconstruction algorithm. A special folding step is incorporated into the rebinning step that makes use of redundant rays.

Once rebinned, the views are reconstructed using a gridding-type Fourier technique that has been modified according to the present invention. The views of each scan are treated in such a way as to effect a weighting of the backprojected view by a function that depends on the distance from the reconstruction circle edge, measured in the direction of the view. Rather than perform the weighting in the spatial domain using a custom backprojector, the present invention performs the weighting in the Fourier domain, by convolving the transformed view with the Fourier transform of a suitable weighting function.

Reconstruction according to the present invention is carried out using general purpose array processors, and there is no speed penalty for high order interpolation during backprojection. The quality of the reconstructed image is excellent, and zoomed, off-axis reconstructions are possible.

Thus, in a first aspect, the present invention provides a method for rebinning fan beam data into parallel beam format, a step necessary to make use of a fast executing parallel beam reconstruction algorithm. Applicant's rebinning method consists of two one-dimensional interpolation steps with a folding step in between. The folding step uses rebinning weights that foldover redundant data at the top and bottom of the fan beam sinogram. The redundant rays are found in the upper left and lower right corners of the sinogram in an intermediate step in rebinning, and each redundant ray corresponds to one ray in the central, non-redundant, part of the sinogram.

Weighting is such that the weight of the redundant ray plus the weight of the central ray sum to one, with the sum of the weighted central ray plus the weighted redundant ray replacing the central ray value in the intermediate sinogram. Thus, applicant's fold-over rebinning advantageously uses all of the data from the fan beam X-rays.

Applicant's fold-over rebinning technique may be used in single scan CT reconstructions and in multiple scan cone beam correction reconstructions. For cone beam correction reconstructions, the rebinning technique is applied to two scans at once and results in two parallel beam sinograms.

Redundant rays from one scan are added to the central rays of the other scan and vice versa using the above rebinning weights. This results in parallel beam sinograms properly prepared for use in applicant's cone beam correction parallel beam reconstruction method.

In a second aspect, the present invention provides a fast executing modification of the parallel beam Fourier reconstruction method as described by Tabei. This modification may be used either for reconstruction of single scans or for multiple scan cone beam correction reconstruction. Applicant's reconstruction method first filters the parallel beam data for each view (which has resulted from applicant's modified rebinning algorithm) with a conventional parallel beam kernel, circularly shifts, and then transforms. Next, the transform is replicated and multiplied by an interpolation filter. The thus processed data are then convolved with a gridding function and added into the Fourier image at an angle corresponding to the view angle. After all views have been treated as above, the two-dimensional inverse Fourier transform is taken to yield a preliminary image.

Finally, the center of the preliminary image is extracted and multiplied by the inverse of the transform of the gridding function, thus yielding the desired image. The present invention preferably achieves this implementation by using a Kaiser-Bessel gridding function that is precalculated and stored in a table.

In a third aspect, the present invention implements cone beam correction reconstruction using the above parallel beam Fourier reconstruction method, whereby cone beam error is substantially corrected. Cone beam error correction requires two or more scans to reconstruct an image. In an n-scan reconstruction, the present invention requires n scans that are separated along the z-axis by a distance equal to $d/(n-1)$, where d is the tangent of the cone angle times the reconstruction circle diameter.

Data from each scan is weighted during backprojection using a cone beam weight function. By suitably weighting the data, a resultant composite scan that has zero cone beam error is created perpendicular to the z-axis. Preferably, cone beam weighting occurs in the transform domain at the transform backprojection step of the Tabei algorithm. According to the present invention, the cone beam weight functions are approximated by functions having relatively few non-zero points in their Fourier transform. Multiplication by the cone beam weights in the spatial domain is accomplished by convolution by the transform of the weights in the transform domain. This convolution is accomplished by multiplication of the transformed view by each non-zero co-efficient of the transform of the weights, and gridding at a position determined by the co-efficient. Rapid processing is promoted in that the relatively few non-zero points require less data processing.

The present invention further utilizes a Kaiser-Bessel gridding function, the values for which are pre-stored in a look-up table to expedite processing. The present invention further provides zooming of the reconstructed displayed image, without requiring zooming to be at the image center.

Other features and advantages of the invention will appear from the following description in which the preferred embodiments have been set forth in detail in conjunction with the accompanying drawings.

DESCRIPTION OF THE PREFERRED EMBODIMENTS

Figure 1A:
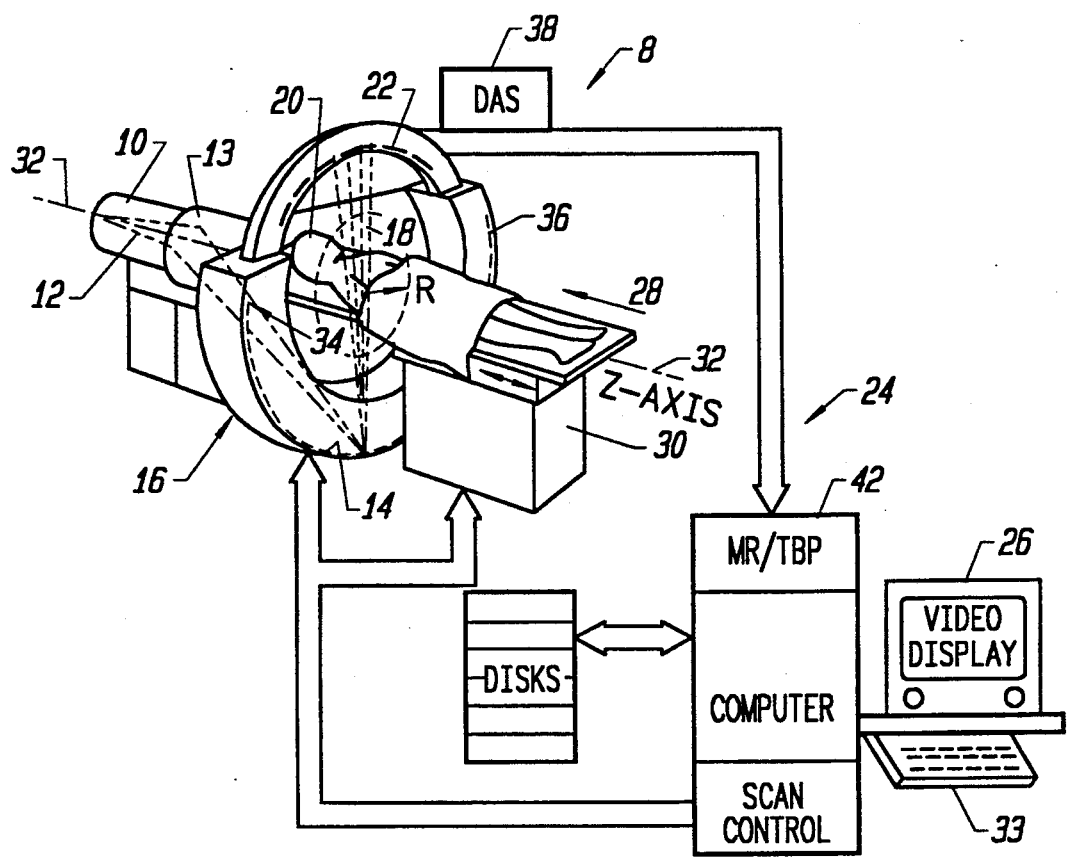
FIG. 1A depicts a fan beam scanning electron beam computed tomography system that includes the present invention.

FIG. 1A depicts a scanning electron beam computed tomography ("CT") system 8 that includes a vacuum housing chamber 10 wherein an electron beam 12 is generated and caused by a beam optics assembly 13 to scan a circular target 14 located within chamber 12's front lower portion 16. Upon being struck by the electron beam, which typically scans 210° or so, the target emits a moving fan-like beam of X-rays 18 that pass through a region of a subject 20 (e.g., a patient or other object) lying within the reconstruction radius R. These rays then register upon a region of a detector array 22 located generally diametrically opposite. The detector array outputs data to a computer processing system 24 that processes and records the data to produce an image of a slice of the subject on a video monitor 26. As indicated in FIG. 1A, the computer system 24 may also control the system 8, and includes the present invention 42, MR/TBP, a modified rebinning and transform back projection method whereby cone beam error is substantially eliminated.

The system of FIG. 1A is a fan-beam system, and provides fan beam data in a fan beam sinogram (or data array). While fan beam data may be suitably processed using spatial domain algorithms to provide a reconstructed image of an X-ray object, such reconstruction involves many mathematical operations that require custom designed special hardware to implement. Thus, for reasons of processing speed and the ability to use standardized array processing equipment, it is preferred to convert, or rebin, the fan beam data to parallel beam data. Once the data has been suitably rebinned, transform domain backprojection techniques suitable for parallel beam data may be used to reconstruct an image, without requiring specialized processing equipment.

Figure 1B:
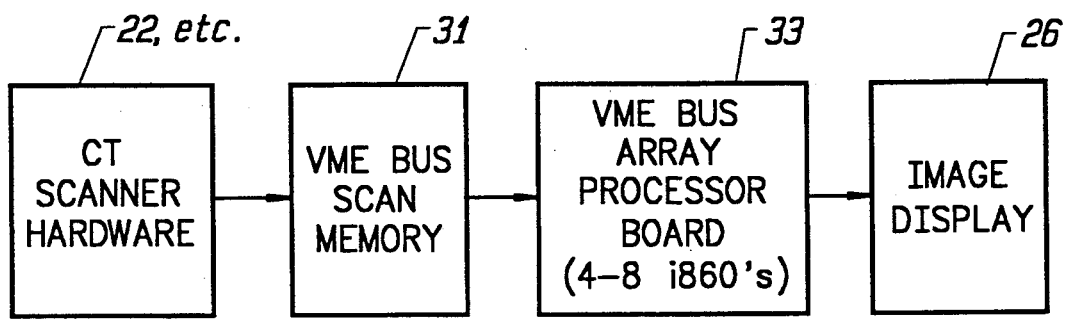
FIG. 1B is a block diagram of reconstruction system hardware, according to the present invention.

FIG. 1B is a more detailed depiction of hardware implementing the present invention. Data from the CT scanner hardware, e.g., from detectors 22, are received into computer processing system 24, more specifically into a VME Bus Scan Memory 31. The data are then moved into a VME Bus array processor board 33 that is part of system 24. The array process board preferably uses four to eight standard, commercially available i860 high speed, floating point computational processors that implement the method of the present invention. The i860 array processors are manufactured by Mercury Computer Systems, Inc., located in Lowell, Mass. After suitable signal processing according to the present invention, which preferably is stored within computer system 24, a reconstructed image, substantially free of cone beam artifacts, is displayed on monitor 26.

Figure 1C:
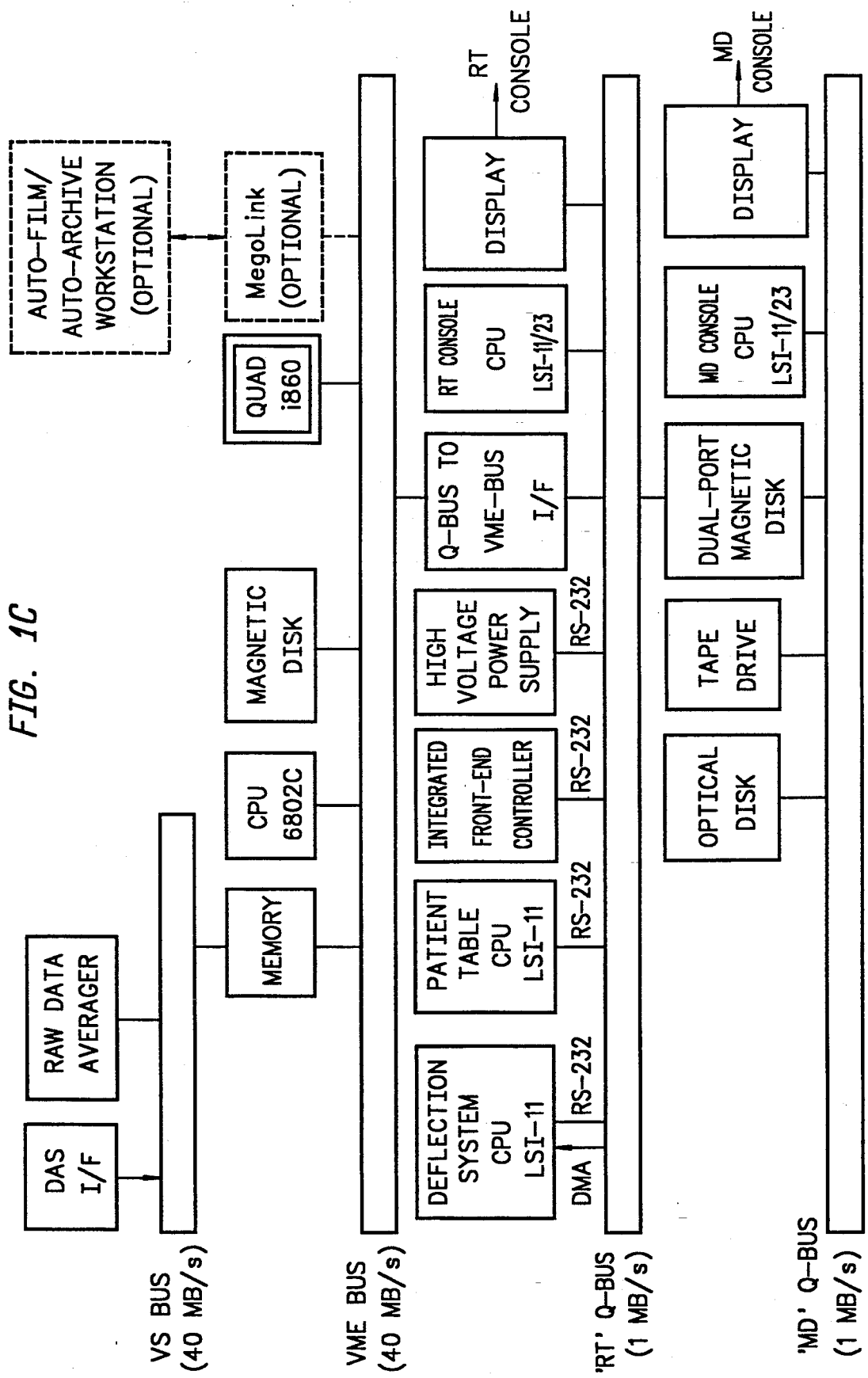
FIG. 1C is a more detailed block diagram of hardware implementing a preferred embodiment of the present invention.

FIG. 1C is a further detailed depiction of system 8.

Figure 2A:
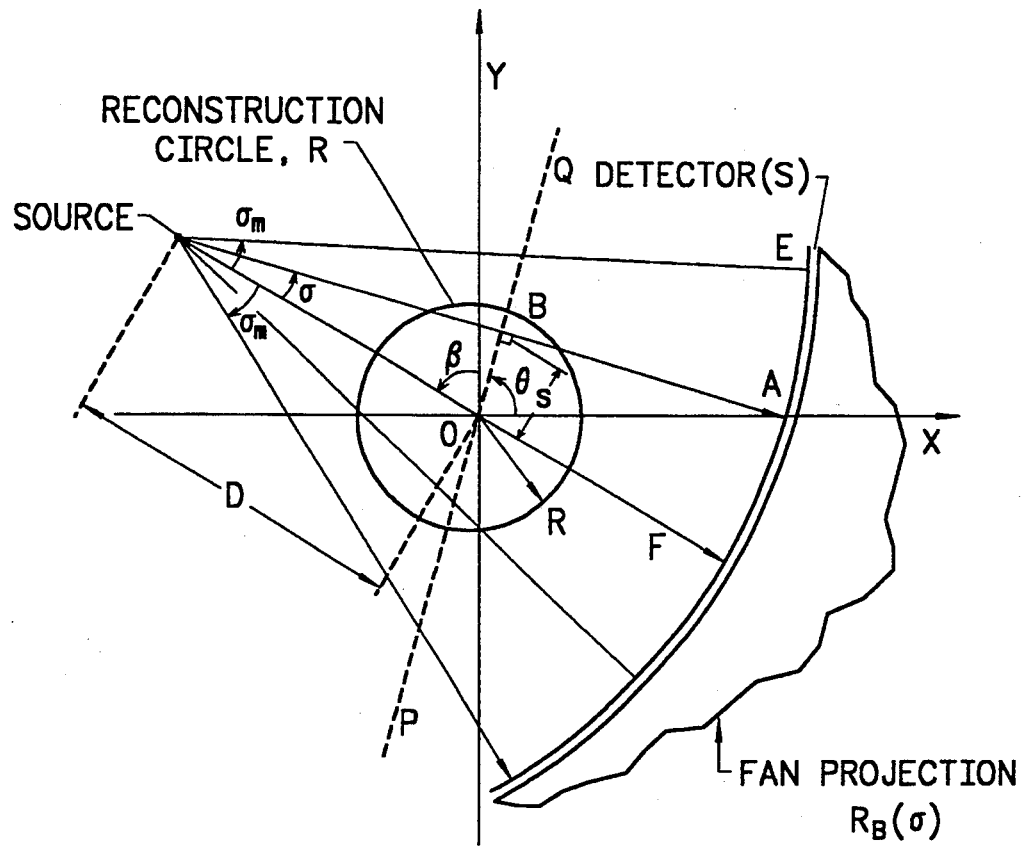
FIG. 2A depicts fan beam geometry, and associated measurement coordinates.
Figure 2B:
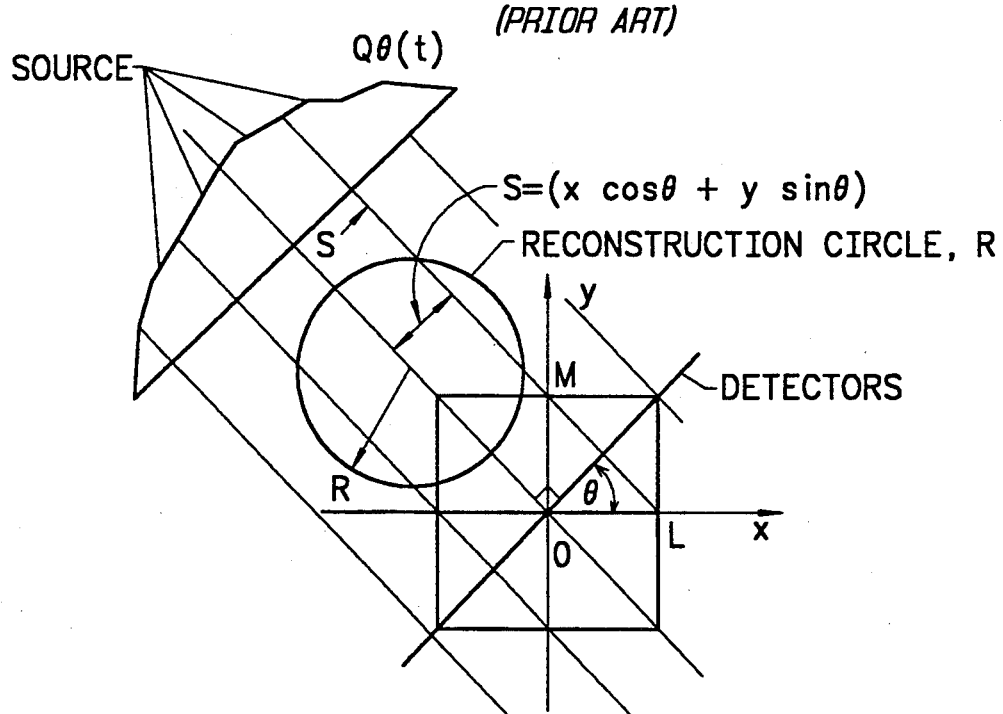
FIG. 2B depicts parallel beam geometry, and associated measurement coordinates.

FIGS. 2A and 2B depict the relationship between the fan beam sinogram coordinates associated with a system such as that shown in FIG. 1A, and parallel beam sinogram coordinates. In the fan beam configuration of FIG. 2A, X-rays radiate fan-like from a common source and are detected, after perhaps being attenuated by an object within a reconstruction radius intermediate to the source and detectors. In FIG. 2A, the detector(s) lie in a circular arc, similar to what is shown in FIG. 1A. In FIG. 2A, $\beta$ is the view angle of the fan center and determines view orientation, while $\sigma$ is the angle of each ray within each fan beam view, where $-A/2 \leq \sigma \leq +A/2$, where A is the fan angle, the maximum angle needed to encompass the entire reconstruction circle of radius R. In the parallel beam configuration of FIG. 2B, rays generated by a source are all parallel in one direction and after perhaps being attenuated by an object within a reconstruction radius are detected by detectors lying in a plane parallel to the plane of the sources. In FIG. 2B, $\theta$ is the angle of the view, and S is the position of the ray within the view, $-R \leq s \leq R$, where R is the reconstruction circle radius.

Because the present invention is used with a fan beam CT system, it is first necessary to rebin the fan beam data into parallel beam format in order to use a modified parallel beam Fourier technique reconstruction method. Rebinning converts fan beam data having fan beam coordinates $(\sigma, \beta)$ into parallel beam geometry that has parallel beam coordinates $(s, \theta)$.

CT data acquired by a fan beam scanner, such as shown in FIG. 1A, is converted by normalization routines into a fan beam sinogram:

$$f(\sigma, \beta), \ -\frac{A}{2} < \sigma < \frac{A}{2}, \ 0 < \beta < \pi + A.$$

where $\beta$ is the view angle, $\theta$ is the angle within a view, and A is the fan angle. The views cover angles from 0 to $\pi + A$, which is the minimum needed for short scan fan beam reconstruction.

It will be appreciated that in a fan beam geometry, each fan ray comes from one parallel view that is parallel to the ray, and vice versa. In essence, rebinning takes such ray and places it into the correct bin in the parallel view.

The rebinning algorithm is a two-dimensional interpolation of the input fan beam data that converts the data into parallel beam coordinates:

$$f(s, \theta), \ -R < s < R, \ 0 < \theta < \pi$$

where $\theta$ is the parallel view angle, s is the distance within the view, and R is the reconstruction radius. The relation between the two coordinate systems is given by:

$$\theta = \beta + \sigma$$

$$s = R \sin \sigma.$$

The input fan beam sinogram 50 covers 180°+fan angle, whereas the output parallel beam sinogram 62 covers 180°.

Figure 3A:
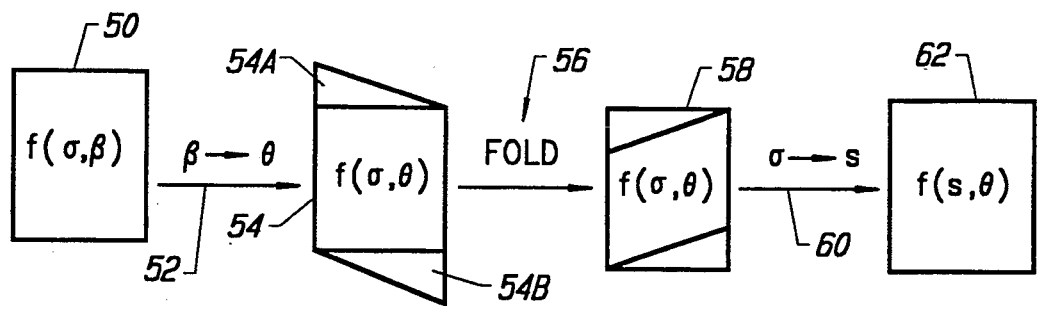
FIG. 3A depicts a modified procedure that provides a foldover step during conversation of fan beam data into parallel beam geometry, according to the present invention.
Figure 3B:
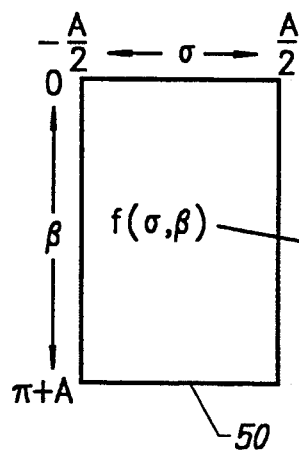
FIG. 3B depicts in further detail the foldover step using in a fan beam to parallel beam rebinning conversion, according to the present invention.

The two-dimensional coordinate change is accomplished in two one-dimensional steps. As shown in the sinogram depiction of FIG. 3A, the input fan beam sinogram 50 first undergoes a one-dimensional transformation of the columns, step 52, from $f(\sigma, \beta)$ to $f(\sigma, \theta)$. The angle between parallel views is chosen to equal the angle between fan beam views. In this case, the transformation on each column is just a shift of the data, which is accomplished by interpolation. This step can be displayed graphically as shown in FIG. 3B.

In the preferred embodiment, the step size in $\theta$ is taken to be equal to the step size in $\beta$, whereupon this interpolation amounts to a shift of each column. With reference to the listing of the rebinning algorithm used in the present invention, APPENDIX 1 attached, the input fan beam sinogram 50 has size fansamps·fanviews, where fansamps is the number of equiangular fan beam samples, and fanviews is the number of fan beam views. The rebinning algorithm assumes that the fan views cover 180 degrees plus the fan angle A. APPENDIX 1 is believed to be sufficiently annotated as to be readily understood by one skilled in the relevant art. To the extent any of the nomenclature in APPENDIX 1 may differ from what is set forth in the Specification text, such differences will be readily apparent to those skilled in the relevant art.

After the rebinning column transformation step 52, the resulting intermediate $f(\sigma, \theta)$ sinogram contains more data than is strictly necessary for a parallel beam reconstruction. More specifically, the central rectangular portion 54 holds all the data necessary for a parallel beam reconstruction. The data in the triangular portions 54A, 54B are redundant. By this it is meant that the spatial position of a ray in 54A determined by the angles $(\sigma, \theta)$ is the same as the position of the ray determined by the angles $(-\sigma, \theta + \pi)$. That ray will fall inside the central rectangle 54. Similarly a ray in the triangle 54B at $(\sigma_1, \theta_1)$ has the same position as $(-\sigma_1, \theta_1 - \pi)$, which is in the central rectangle 54. Thus the data in the corner triangular regions 54A and 54B may be discarded or, more preferably, folded into the central rectangle.

Figure 3C:
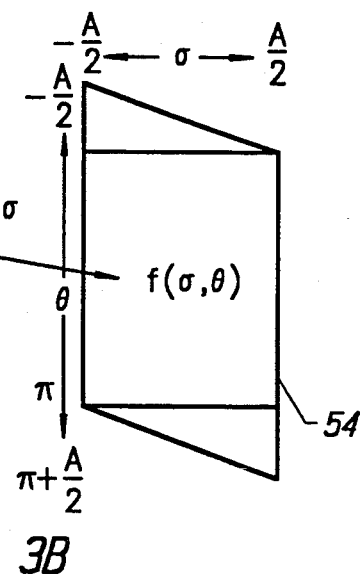
FIG. 3C depicts the effect of the foldover step depicted in FIG. 3B, according to the present invention.

At step 56, foldover occurs, whereby the redundant data in the corner triangles 54A, 54B are folded into the main sinogram 54, resulting in the sinogram shown in FIG. 3C.

In one aspect of the present invention, applicant has discovered that it is possible to create foldover weights, for use at step 56, using formulae known in the art for use with short scan fan beam reconstruction. Applicant's rebinning weights are calculated in the same manner that weights were determined for a short scan fan beam algorithm (wherein no rebinning occurs) as described in the Dennis Parker reference, cited earlier herein. The use of such weights for rebinning as disclosed herein is believed new. The rebinning used with the present invention is especially advantageous in providing a convenient processing step whereat to insert a folding step 56. Further, a multiple scan data foldover step disclosed herein is required to both correct cone beam error and permit reconstruction using parallel beam techniques.

As will be described, foldover 56 is required for subsequent cone beam error correction. Folding over makes full use of all data obtained from a radiated object, and improves the signal-to-noise ratio in the reconstructed image, as viewed on display 26. Further, when acquired from a fan beam system, not all of the redundant data in sinogram 54 are collected in the same plane, due to the $\Delta z$ error noted earlier, which error gives rise to cone beam artifacts when reconstructing the image.

To do cone beam reconstruction according to the present invention, applicant's modified cone beam algorithm makes use of two or more fan beam scans to create one image, thus making it necessary to rebin on two or more scans. Rebinning on a single scan would not yield the desired reconstruction, although a foldover step using data from a single scan would still help reduce cone beam artifacts for that one scan.

For a cone beam reconstruction that requires n scans the rebinning algorithm of the present invention proceeds on pairs of scans as follows. The first scan is paired with scan n, the second with the scan n−1, and so on. If n is odd the middle scan will not have a pair. This scan is then rebinned by itself and the folding is done into itself.

Figure 3D:
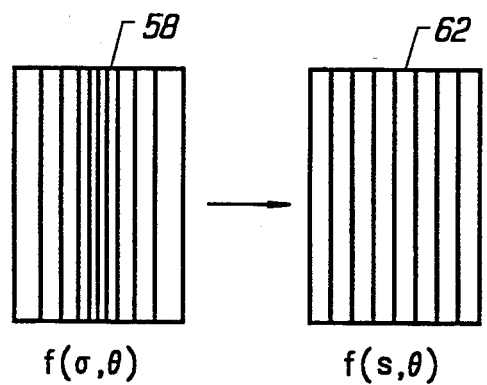
FIG. 3D shows in detail the last rebinning coordinate change, according to the present invention.
Figure 3E:
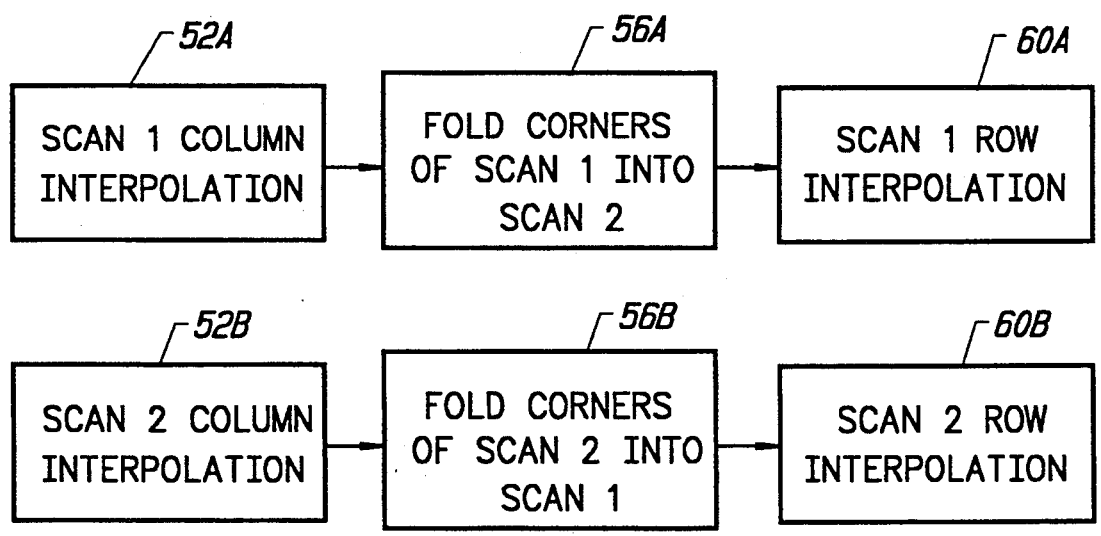
FIG. 3E shows a two scan rebinning procedure, including folding over, according to the present invention.

In the present invention, the corner areas of one scan require folding into the central area of the other scan, in which case the rebinning algorithm performs rebinning on both scans at once. At the folding step, e.g., step 56 in FIG. 3A, the rebinning algorithm folds the corner areas of the first scan into the main portion of the second scan and vice versa. FIG. 3E depicts two scan cone beam rebinning, wherein input data from two fan beam sinograms acquired a small distance $\Delta z$ apart are rebinned simultaneously, with the rebinning output being two parallel beam sinograms. In FIG. 3E, step 52-A denotes column interpolation for the data of the first scan, whereas step 52-B denotes column interpolation for the data of the second scan.

Returning to FIG. 3A, in step 56, in general folding is accomplished by weighting each central point and corresponding corner point or regions 54A, 54B, using weights derived from those used in short scan fan beam reconstruction. The weight used as a co-efficient for the sinogram corner of one scan, and the weight used as the co-efficient for the sinogram center of the other scan always add to one. Thus weighted, the sinogram corner of one scan is added to the sinogram center of the other scan. According to the present invention, by doing the foldover step 56 as shown in FIG. 3E, after the first one-dimensional interpolation, a further interpolation is avoided. A sinogram does not consist of an infinite number of points, but rather a finite number of points at discrete positions. The positions are so chosen that if the coordinates $(\sigma, \theta)$ fall exactly at a data point present in the sinogram then the coordinates $(-\sigma, \theta+\pi)$ or $(-\sigma, \theta-\pi)$ will also fall exactly on a point present in the sinogram. Thus interpolation between two points is not necessary in the folding step. This is not the case if the folding step were done on the sinogram at stage 50 or 62 in FIG. 3A.

For an actual fan beam CT scanner as shown in FIG. 1A, for example the C-150 model manufactured by Imatron, Inc., of So. San Francisco, Calif., data in corners 54A, 54B are not truly redundant. Due to the cone beam geometry of this scanner, the corner rays have a slightly different orientation than the corresponding central rays.

After foldover step 56, the resultant sinogram 58 undergoes a final rebinning step 60 that results in a row transformation from $f(\sigma,\theta)$ to $f(s,\theta)$, resulting in the parallel beam sinogram 62. In step 60, each row is interpolated from $(\sigma,\theta)$ coordinates into parallel beam geometry having parallel beam coordinates $(s,\theta)$. With further reference to FIG. 3A, this second coordinate change 60, from $\sigma$ to s is done on each row of the $f(\sigma,\theta)$ sinogram 58 using the equation $s=D\sin\sigma$, where D is the distance from the X-ray source to the detector. This second coordinate change is accomplished by a straight forward interpolation of each row, and is depicted in FIG. 3D. The vertical lines in FIG. 3D indicate that lines equally spaced in s do not fall an equal distance apart in the sinogram 58, but are converted by step 60 to sinogram 62 in which they are an equal distance apart.

According to the present invention, interpolations are used repeatedly in the rebinning process. The general interpolation algorithm may be described as follows:

Let there be a function f(i) defined on integer points, where it is desired to find the interpolated value of f at a point x where $0<x<1$. This value of the function f(i) is calculated from the formula:

$$f(x) = \sum_{m=-ni}^{m \leq ni} f(m) I(x - m)$$

where I(x) is the interpolation kernel, and ni is the order of the interpolation. An interpolation of order ni will use 2 ni points of the original function for each output point. In the present invention, the interpolation kernel used in the rebinning interpolations is a sinc function, $(\sin \pi x)/\pi x$, tapered by a Gaussian, where the kernel size may be any length n:

$$I(x) = \sin c(x) \cdot \exp-(x^2/ni)$$

In practice, this function is slightly modified in that the values of I(x) are scaled so that for all x, $0 \leq x \leq 1$:

$$\sum_{m=-ni}^{m \leq ni} I(x - m) = 1$$

At this juncture, the original fan beam data have been transformed into a parallel beam sinogram of size nsamps x nviews, where the number of samples per view is nsamps, the number of views is nviews, and where the set of views covers 180°. View v will represent a parallel projection at angle vangle=v·180/nviews. It will be assumed that nr is the least power of two greater or equal to nsamps.

The following describes the preparation of each view prior to backprojection using applicant's parallel beam backprojection modified Fourier technique, which is a modification of prior art gridding type techniques.

By suitably modifying and combining features from these various techniques, the present invention is able to correct cone beam error in a fan beam CT system, using Fourier methods.

Figure 5:
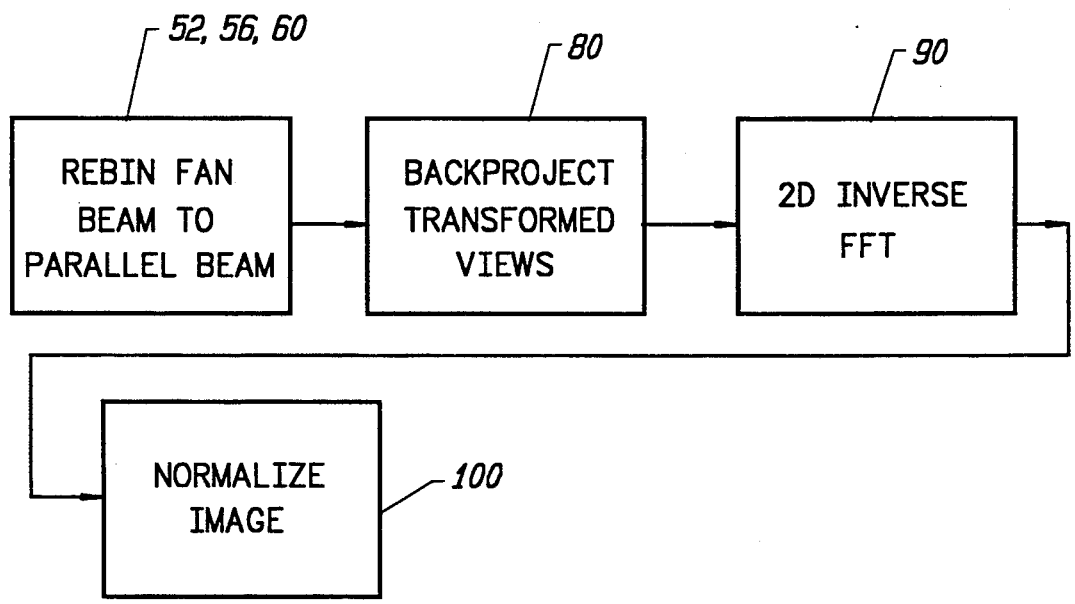
FIG. 5 is a generalized block diagram showing transform backprojection, according to the present invention.
Figure 6:
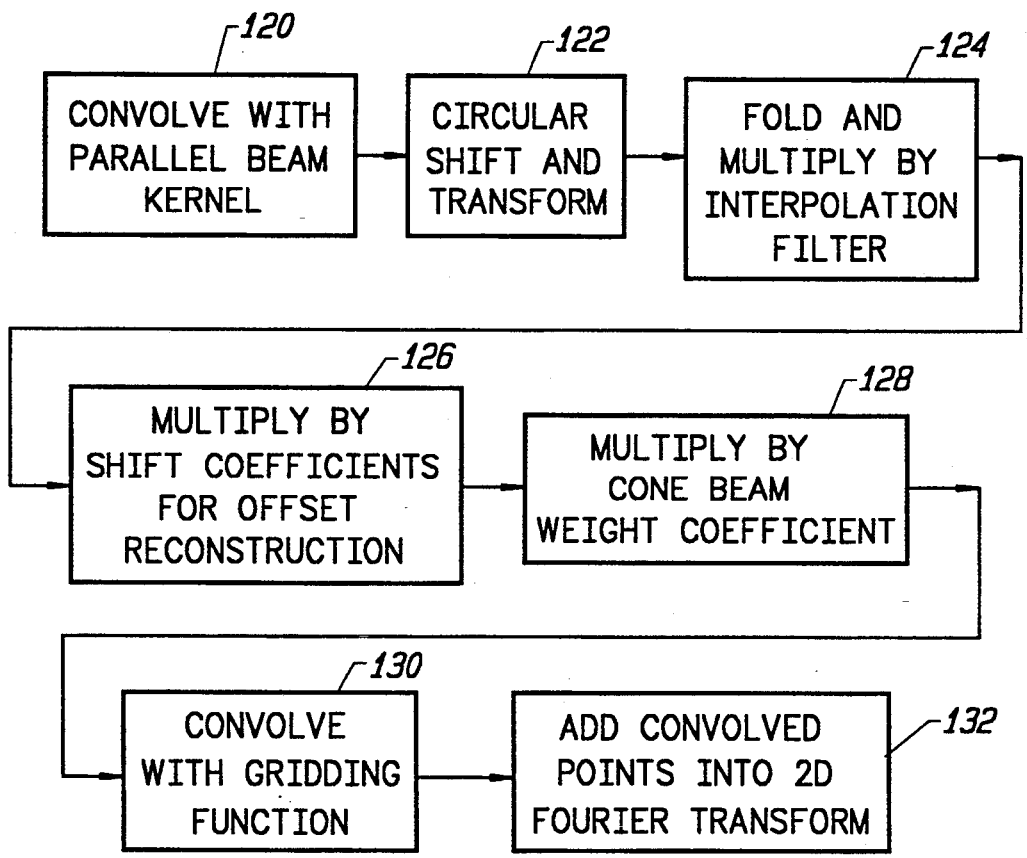
FIG. 6 is a block diagram showing backprojection of transformed views, according to the present invention.
Figure 7:
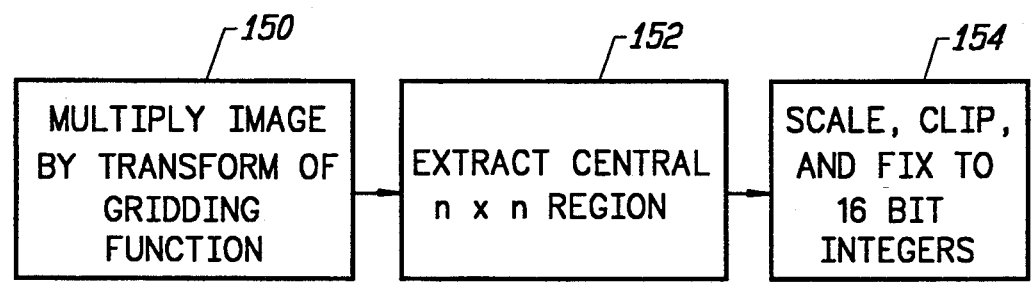
FIG. 7 is a block diagram showing normalization of a reconstructed image, according to the present invention.

According to the present invention, applicant's modified algorithm, a Tabei type transform backprojection algorithm, has the following process steps, as shown in FIGS. 5-7. FIG. 5 gives an overview of the process.

FIG. 6 gives details of FIG. 5 step 80. FIG. 7 gives details of FIG. 5 step 100.

The input to the process is a set of n parallel beam sinograms, each sinogram consisting of a set of views. For each of the n sinograms there is a different cone beam weight function. In the case when n is one then no cone beam correction is done.

(1) for each view, the parallel beam data (which has resulted from applicant's modified rebinning algorithm, is convolved with a conventional parallel beam kernel (FIG. 6, step 120), e.g., see APPENDIX 1, p. 17, executed by subroutine kerconv);

(2) the result of step (1) is then circularly shifted by an amount equal to half the view width and transformed (FIG. 6, step 122, e.g., see APPENDIX 1, p. 18, executed by subroutine cshift);

(3) the result of step (2) is then replicated by complex conjugate folding and multiplied by an interpolation filter (FIG. 6, step 124, see APPENDIX 1, p. 18, subroutines rfft, foldview and vmul);

(4) in the case of an offset reconstruction the result of step (3) is multiplied by shift coefficients (FIG. 6, step 126);

(5) for each non-zero coefficient in the transform of the cone beam weight function associated with the sinogram multiply the result of step (4) by the coefficient and sum the result for all input sinograms (FIG. 6, step 128);

(6) convolve the result of step (5) with the gridding function and add into the Fourier image at an offset determined by the weight coefficient number and along an angle corresponding to the view angle (FIG. 6, steps 130 and 132);

(7) after steps (5) and (6) are repeated for each non-zero weight coefficient and steps (1) through (6) are repeated for all views, take the two dimensional inverse Fourier transform to get a preliminary image (FIG. 5, step 90);

(8) Finally, for such preliminary image extract the central region and multiply by the transform of the gridding function, then scale and fix to integers to get the desired reconstructed image (FIG. 5, step 100 and FIG. 7, steps 150, 152, 154, e.g., see APPENDIX 1, subroutine fbackpdb used for normal cone beam case).

Briefly, the cone beam correction method of the present invention is analogous to a weighting scheme for each backprojected view, wherein a two-dimensional weighting function is calculated for each view that gives the contribution (weighted 0 to 1) of that view to each pixel in the image. Preferably the two-dimensional weighting function is approximated by a function whose two-dimensional Fourier transform consists of a small number of non-zero terms, to promote speed of execution.

Multiplication of the back-projected view by the two-dimensional weighting function may then be done in the transform domain as a convolution step. The reconstructed image is built-up by summing for each view the backprojection of the view times that view's weighting function.

According to the present invention, the weighting function is simplified by requiring that the scans be interpolated into scans that are perpendicular to the z axis (ignoring the cone angle). Such scans will be denoted z-perp scans. A z-perp scan would result, for example, if the system of FIG. 1A were used to make a scan while the patient was stationary, and then the patient were moved along the z-axis relative to the scanner, at which point another scan were made. For such a method of scan acquisition, the two-dimensional cone beam weighting functions approximate a one dimensional function parallel to the view angle. In an alternate method of scan acquisition, called spiral scanning, the patient is continuously moved while the scanning takes place. The scans thus acquired are not perpendicular to the z-axis and are interpolated to z-perp scans before reconstruction with the present invention.

A transformed backprojection fan beam image is reconstructed from n z-perp scans, where number n and spacing of the z-perp scans is governed by the slice width, cone angle, desired reconstruction circle radius R, and position of the desired images. Interpolation from spiral scan to z-perp scan is straightforward, and each point in the z-perp fan beam sinogram is interpolated linearly from the corresponding points in the nearest spiral scans. If desired, a higher order interpolation may be used.

Figure 4A:
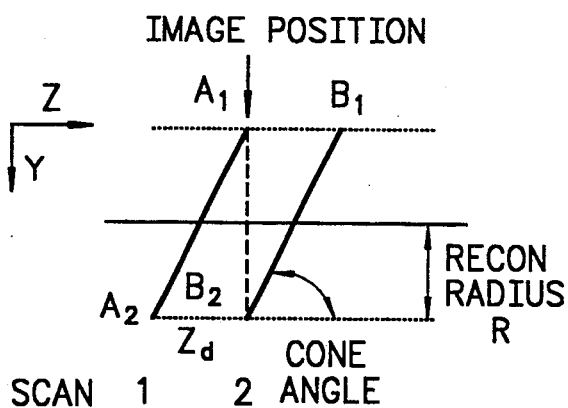
FIGS. 4A and 4B depict scan spacing for a two-scan reconstruction, and associated weighting function, according to the present invention.
Figure 4B:
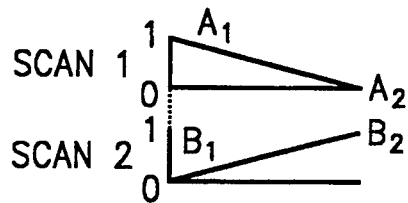

FIGS. 4A and 4B depict z-perp scan spacing and associated weighting functions for a two scan cone beam reconstruction (e.g., two fan beam scans used to reconstruct a single image), while FIGS. 4C, 4D and 4E, 4F are similar depictions for three-scan and four-scan reconstructions, respectively.

Figure 4C:
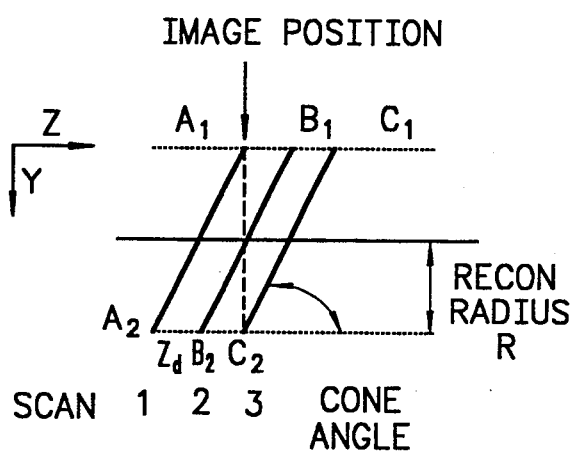
FIGS. 4C and 4D depict scan spacing for a three-scan reconstruction, and associated weighting function, according to the present invention.
Figure 4D:
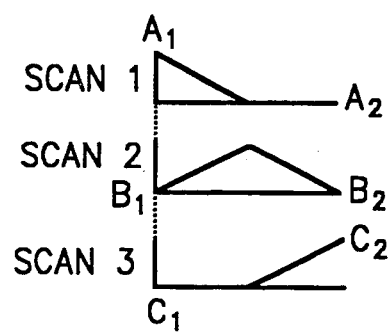
Figure 4E:
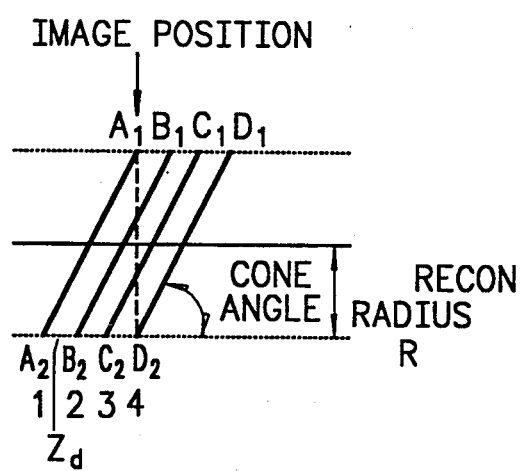
FIGS. 4E and 4F depict scan spacing for a four-scan reconstruction, and associated weighting function, according to the present invention.

In FIGS. 4A, 4C, 4E, there is shown in a vertical phantom line the central rays for one view in each of the two, three and 4 z-perp scans used to create the image whose position is indicated by the dotted line. The inclination of each ray represents the undesired offset in planes defined by the source of the X-ray radiation and by the detectors. By definition, the phantom vertical line has zero offset, and if such a ray actually existed, would represent the desired zero cone beam error condition. In essence, the phantom vertical lines represent a backprojected ray formed as the weighted sum of rays from each scan, which ray does lie in a co-incident plane.

The distance, $z_d$, between z-perp scans is given by $$z_d = d/(n-1)$$

where d is the cone beam distance defined by $$d = \tan(\text{cone angle}) \cdot 2R$$

where n is the number of z-perp scans in the image, and R is the reconstruction radius.

In the case of a 2 scan cone beam correction (FIGS. 4A and 4B), the algorithm will linearly weight each backprojected view in the projection direction with weighting varying from 0 to 1 for the first scan and from 1 to 0 for the second scan. This is done during transform backprojection in the frequency domain by convolving the transformed view with the transform of the weighting function.

In this case, a very simple weighting function may be chosen: a sinewave having but two terms in it's Fourier transform. By zooming in on a small portion of the sine wave near the zero crossing, applicant can synthesize a weighting function that is very nearly linear.

The determination of n, the number of scans input to the cone beam correction, depends on the slice width of each scan, the desired slice width for the image, and the distance d. As a minimum, n should be chosen sufficiently large so 2d is smaller than the scan slice width. Larger n will create an image with a more constant slice width, which will approach the scan slice width as n is increased.

The weighting functions, shown in FIGS. 4B, 4D, 4E for the two, three and four-scan images, are one-dimensional functions that describe the two-dimensional weights applied to the backprojected parallel beam view. The same weight function is applied to all views in a z-perp scan. The weight is applied to the backprojected pixels as a function of distance from the reconstruction circle perimeter measured along the view angle.

Consider, for example, the weighting functions of FIG. 4B. At sweep 1, ray position A1 (FIG. 4A), the data will be perfect because the ray is precisely upon the vertical phantom line position. Therefore the weighting co-efficient is 1 at that position (FIG. 4B, position A1). However for that same ray in sweep 1, as position A2 is reached, the ray goes farther from the ideal vertical position, and accordingly it is given less weight, until at position A2 is given zero weight (see FIG. 4B).

Consider the ray for the second sweep. At position B1 the ray is far from the ideal location, and FIG. 4B indicates that its weight co-efficient is accordingly zero. However at position B2, the ray is precisely on the vertical phantom position, and its co-efficient is 1 (FIG. 4B). By so weighting the rays from sweep 1 and sweep 2, a pseudo-ray having a zero cone beam error position corresponding to the dotted phantom line may be deemed to have been created.

Figure 4F:
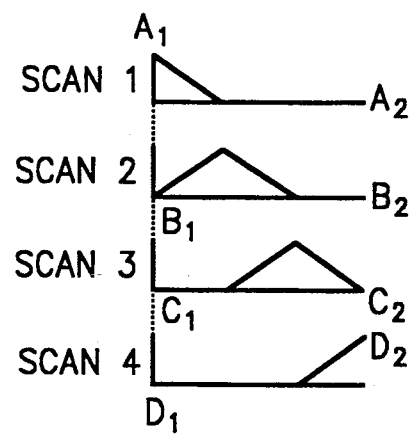

In similar fashion, appropriate weights are depicted in FIGS. 4D and 4F for three and four scan reconstructions, although more than four scans may be used.

Figure 4G:
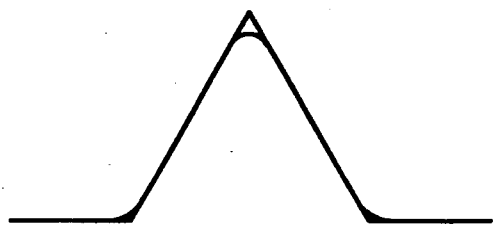
FIG. 4G depicts an approximation to a four-scan weighting function using seven points in the Fourier domain.

These functions used to weight the backprojected views are preferably implemented as a convolution in the transform domain. Since the speed of backprojection varies directly with the number of points in the transform, it is advantageous to approximate the weighting functions with functions requiring fewer transform points. FIG. 4G, for example, is a plot of an approximation to a four scan reconstruction weighting function using only seven points.

FIG. 5 is a generalized block diagram of the present invention, wherein rebinning including steps 52, 56 and 60, as above described, occur first. At process step 80, backprojection of the thus transformed views occurs, and at process step 90, the two-dimension inverse fast Fourier transform of the image is taken, the image being normalized at step 100.

Turning now to FIG. 6, backprojection of transformed views according to the present invention is depicted. Each view in a parallel beam sinogram is processed as shown in FIG. 6, and then added into a two-dimensional Fourier transform.

FIG. 7 provides further detail as to the image normalizing process step 100, shown in FIG. 5.

The method steps shown in FIG. 6 will now be described in further detail. The steps depicted in FIG. 6 are applied to each view in the parallel beam sinogram. In the case of a cone beam scan, there will be two or more parallel beam sinograms that are processed together. Each view will consist of rebinned projection data of length nsamps, with a parallel view angle of vangle, the angle corresponding to angle $\theta$ in FIG. 2B. As noted, the view must be filtered by a parallel beam kernel (FIG. 6, step 120). Preferably this is done by forward transformation, multiplication in the Fourier domain by the transform of the kernel, then inverse transformation. The size of the Fourier transform is 2·nr real points, and the view is padded with zeros to this size.

Next, the convolved view is circularly shifted by nsamps/2 and padded to length nr, see FIG. 6, step 122.

A real Fourier transform is then performed to get an nr/2 +1 length complex vector representing the positive part of the Fourier transform of the convolved view.

The thus transformed view is replicated by folding with conjugation about the nr/2 term producing a nr+1 point complex vector, f(nr/2+i)=f(nr/2−i)*, i=1, . . . , nr/2, FIG. 6, step 124. In practice, the high frequency i=nr term may be discarded, and term 0 is divided by 2.

The replicated view is multiplied by an interpolation filter that may be used to tailor the interpolation frequency response (FIG. 6, step 124). For example, for linear interpolation the filter is $$\sin c(r \cdot \pi/nr)^2, r=0, \ldots, nr-1.$$

For a response closer to cubic interpolation, the filter is $$[8+9 \cdot \cos(\pi \cdot r/nr) - \cos(3 \cdot \pi \cdot r/nr)]/16$$

The view at this stage will be called the transformed view, rather than the convolved, shifted, transformed, replicated, filtered view.

The present invention advantageously permits an off-center image reconstruction by using the Fourier shift theorem to perform a shift in the transform domain (FIG. 5, step 100, FIG. 6, step 126, FIG. 6. The basis of this algorithm is that the parallel beam sinogram, when transformed, becomes a polar coordinate version of the two-dimension fast Fourier transform of the image. Thus, to shift the image, the Fourier shift theorem can be applied to the transformed view.

Assume that shifts of coordinates sx, sy are desired, where the units are such that there are nr units in the reconstruction radius R. The nr complex points in the view are at positions [x(r),y(r)]=[r·−cos(vangle), r·sin(vangle)], r=0, . . . , nr−1. These points are complex-multiplied by $$e^{-(2 \cdot \pi \cdot i \cdot (sx \cdot x(r) + sy \cdot y(r))/nr]}$$

Next, the backprojection of the view is done in the transform domain. The transformed view is convolved with the gridding function and added into the transform of the image. The image is an nf·nf real image, with transform represented as nf/2·nf complex terms.

Backprojection according to the present invention entails providing coordinates for each point in the transformed view, using a gridding function that preferably is a Kaiser-Bessel function whose values are pre-stored in a look-up table, convolution with the gridding function, then addition of the gridded view into the Fourier domain image at positions determined by the coordinates. In the case of a cone beam correction the backprojected view is multiplied by a weighting function. This is accomplished by convolution of the transformed view with the transform of the weight function. This convolution is accomplished by multiplying the transformed view by each non-zero coefficient of the transform of the weight function, and then gridding at coordinates offset from the view coordinates.

More specifically, with respect to the view coordinates, each complex point in the transformed view is given the co-ordinates:

$$(u(r), v(r)) = (-r \cdot reconr \cdot 2 \cdot \cos(vangle), \sin(vangle))$$

where $r = 0, \ldots, nr-1$. Reconr is the fraction of the reconstruction radius R to be covered by the scan. Reconr $= 1.0$ results in a image covering the whole reconstruction circle, whereas reconr $= 0.5$ results in an image covering half of the reconstruction circle, i.e. a zoom of 2.

The point is to be multiplied by the gridding function and added into the image at points centered at the image co-ordinate. The choice of angle $[\cos(vangle), -\sin(vangle)]$ in the Fourier image produces a backprojection angle of $[-\sin(vangle), -\cos(vangle)]$ in the spatial image, where the y direction is positive measured downward.

Since the coordinate calculation depends on cos(vangle) and sin(vangle), symmetries of these trigonometric functions can be used to reduce calculations. The coordinates are calculated for four views at once: the views at vangle, $\pi$-vangle, vangle+$\pi/2$, and $\pi/2$-vangle. Relations between the sines and cosines of these angles allow a reduction in calculation by a factor of two.

The gridding function is preferably a small, separable two-dimensional real function whose width is given by the variable nt. Preferably the gridding function is a Kaiser-Bessel function with shape governed by a parameter $\beta$:

$$cf(x) = besselI0(\beta \cdot \sqrt{(1.0 - w(x))})/besselI0(\beta)$$

$$w(x) = (2 \cdot x/nt)^2$$

$-nt/2 < x < nt/2$, $cf(x) = 0$ elsewhere.

As shown in FIG. 7, step 150, next each point of the transformed view, fv(r) is multiplied by the gridding function and added into the Fourier image, fim(iu,iv) using the formula:

$$fim(iu,iv) = fim(iu,iv) + cf(iu - u(r)) \cdot cf(iv - v(r)) \cdot fv(r)$$

The gridding function is zero except for an nt x nt square around the position (u(r),v(r)). Thus, this method step consists of determining the nt-nt values of the gridding function for the position (u(r),v(r)), multiplying the values by fv(r), and then adding them into the image.

The gridding function is separable so only 2nt values must be determined. These values depend on the fractional errors ceil(u(r))−u(r), and ceil(v(r))−v(r). Rather than calculate the gridding function each time, the present invention pre-calculate a table of values indexed by quantized fractional errors. With respect to FIG. 1A, the look-up table storing these values preferably is associated with computer system 24.

A table size nq=1024 appears sufficient, in which case the table will contain nt entries for each q, q 32 0, ..., nq−1:

$$table[q,j] = cf(q/nq + j - nt/2), j = 0, \ldots, nt-1.$$

The variables governing a two scan cone beam backprojection will now be described, with reference to the attached APPENDIX 1, which lists the relevant code.

va1, va2 are the first and second weighting angles.

$va1 = vangle + \pi$ if $vangle < \pi/2$, and $va1 = vangle$ if $vangle < \pi/2$ $va2 = vangle$ if $vangle < \pi/2$, and $va2 = vangle + \pi$ if $vangle \geq \pi/2$.

cbscale is the slope of the weighting=reconr/coner. A slope of one means that the weighting goes from 0 at +reconr to 1 at −reconr.

cbdist0 is the default value for cbdist, the parameter that determines the amount of zooming in on the sine wave.

cbdist is the distance in Fourier image coordinates between 0 and the positive term of the sine wave expansion. cbdist=cbdist0·cbscale.

cbmult is a needed scale factor:

$$cbmult = .5/\sin(cbdist0 \cdot \pi/2).$$

tsh is an angular shift, different for each scan, that specifies the desired part of the sine wave.

$$tsh1 = cbdist0 \cdot \pi/2 \cdot [1.0 + cbscale \cdot (\sin(va1) \cdot x0 + \cos(-va1) \cdot y0)]$$

$$tsh2 = cbdist0 \cdot \pi/2 \cdot [1.0 + cbscale \cdot (\sin(va2) \cdot x0 + \cos(-va2) \cdot y0)]$$

cbcoeff is the complex coefficient of the Fourier representation of the sinewave.

$$cbcoeff1 = (cbmult \cdot \sin(tsh1), -cbmult \cdot \cos(tsh1))$$

$$cbcoeff2 = (cbmult \cdot \sin(tsh2), +cbmult \cdot \cos(tsh2))$$

Consider now the cone beam backprojection, where view1 is the transformed view of the first scan, and view2 is the transformed view of the second scan. First, view1 is multiplied by cbcoeff1, and view2 is multiplied by cbcoeff2. Next the results are added and then backprojected at the points (sin(va1)·cbdist+u(r), cos(-va1)·cbdist+v(r)), $r=0, \ldots, nr-1$.

Coordinates (u(r) ,v(r) )=r·reconr·2·[cos(vangle),-−sin(vangle)], where $r=0, \ldots, nr-1$, and where reconr is the fraction of the reconstruction radius R to be covered by the scan Next cbcoeff1 and cbcoeff2 are conjugated, the two views multiplied and added as above, and then backprojected at the points (−sin(va1)·cbdist+u(r), −cos(-va1)·cbdist+v(r)), $r=0, \ldots, nr-1$.

Although a preferred implementation reconstructs cone beam data using two scans, more than two scans may instead be used, in which case more sophisticated weighting functions must be synthesized.

In FIG. 4B, for example, the weighting functions for a two scan correction are a negatively sloping ramp going from 1 to 0, and a positively sloping ramp going from 0 to 1. It follows, then, that the weighting functions needed for a four scan cone beam correction will have the downward slope of scan 1 in FIG. 4D, the triangular slope of scan 2 in FIG. 4F, the once-delayed increasing slope of scan 3 in FIG. 4D, and the twice-delayed slope of scan 4 in FIG. 4F. Such shapes can be approximately synthesized by using several terms in the Fourier transform of the weighting function.

Next, the gridded view is added into the Fourier image. The Fourier image, fim(iu,iv) is defined for iu=0, ..., nf/2, iv=0, ..., nf−1. In the fim(iu, iv) gridding formula noted above, iu and iv may range over all integers but are then mapped into the Fourier image modulo nf, i e. iu=iu % nf, iv=iv % nf.

If iu >nf/2, then iv is replaced by nf−iv, iu is replaced by nf−iu, and the value of the term is conjugated.

Inverse transformation and normalization of the image next occurs, FIG. 5, steps 90 and 100. After backprojection of all views, the Fourier image is formatted to conform to the packing convention of the fast Fourier transform software used with the present invention, and is inverse transformed. The resulting image is then divided by the transform of the convolving function.

This transform is calculated as follows. First, a complex function is created using the formula:

$$c(i)=(cf(i), 0) \; i=0, \ldots, nf/2-1.$$

This function is inverse transformed to get a real function $$w(i), i=0, nf-1.$$

Then $n(i)=\sqrt{(scale)}/w(i)$ is formed. Finally, the image point im(i,j) is multiplied by n(i)·n(j). Only the center nf/2·nf/2 portion of the resulting image is used (FIG. 7, step 152), and preferably is fixed to 16 bit integers (FIG. 7, step 154).

Figure 8A:
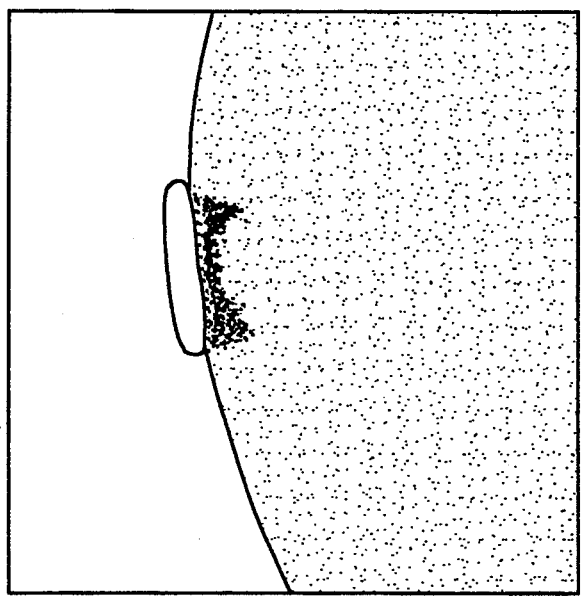
FIGS. 8A and 8B are fan beam reconstructions showing cone beam artifacts.
Figure 8B:
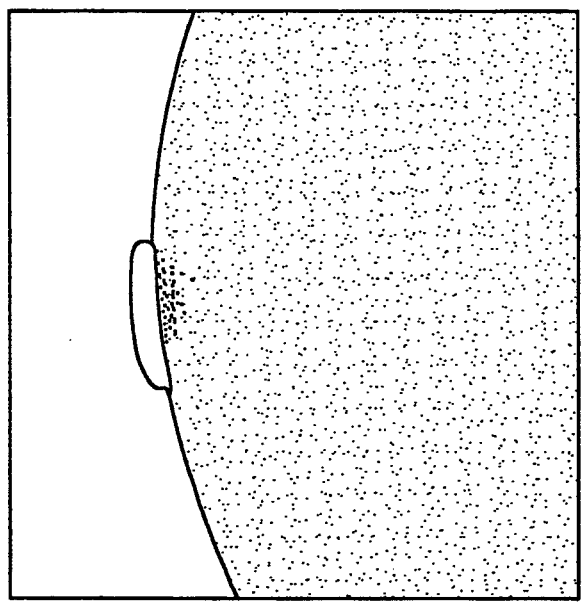
Figure 9A:
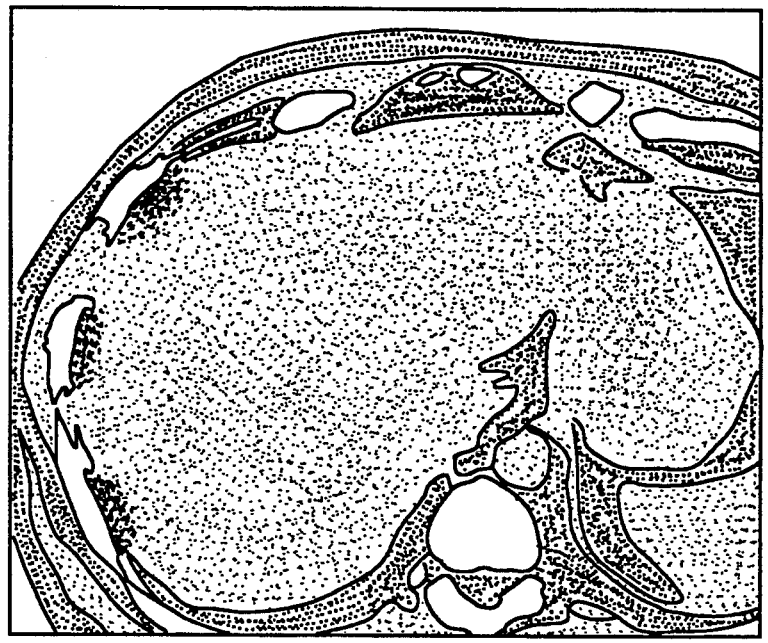
FIGS. 9A and 9B are fan beam reconstructions with reduction of cone beam artifacts, according to the present invention.
Figure 9B:
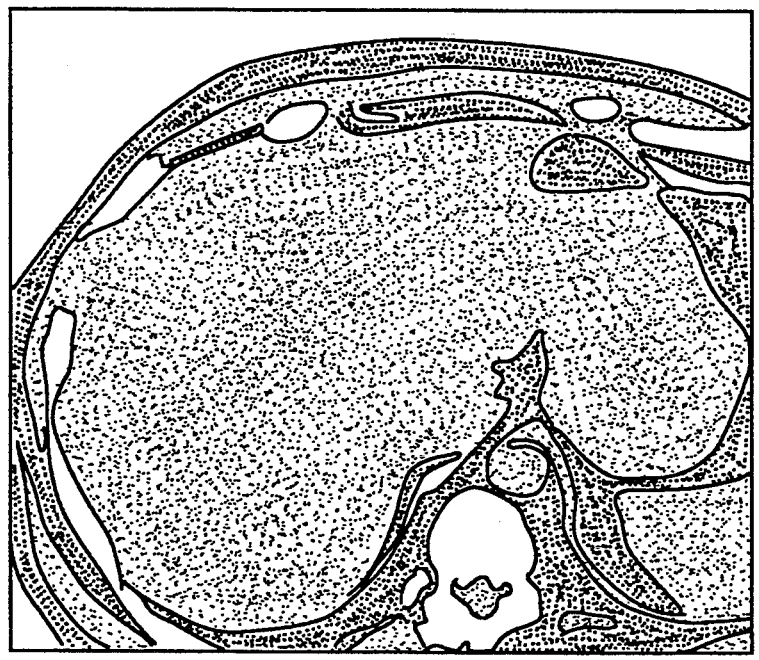

Having described the preferred embodiments, FIGS. 8B and 9B depict the improvement resulting from use of the present invention, when compared to respective FIGS. 8A and 9A. The images of FIGS. 8A, 8B, 9A and 8B were taken from an Imatron model C-150 fan beam scanner, having 6 mm slice thickness, and show a 13 cm reconstruction radius.

FIGS. 8A and 9A are two uncorrected images of a rib phantom, wherein image reconstruction was made using a prior art fan beam algorithm. Note the cone beam error in FIGS. 8A and 9A, manifested by shadowing behind the rib, which appears in white.

By contrast, FIGS. 8B and 9B show an image from the same scanner, after processing by the present invention. Two z-perp scans were used to create the images of FIGS. 8B and 9B, with 3 mm separation between scans. Note the reduction in cone bean error in these figures when compared respectively to FIGS. 8A and 9A. The rib, in white, has substantially no cone beam shadow artifact.

For fan beam data acquired from an Imatron model C-150 scanner, execution time for the present invention running on a single 860 processor is presently approximated by:

$$T=7.5 \cdot Nscans + 9.8 Npoints + 1.5$$

where Nscans is the number of z-perp scans used in the reconstruction, N points is the number of complex points used in the Fourier transform of the weighting function. For example, for a two scan cone beam scan, and a two point weighting function, $T \approx 36.1$ seconds. Of course, this run time may be cut by a factor of four by executing on a quad 860 processor board.

Modifications and variations may be made to the disclosed embodiments without departing from the subject and spirit of the invention as defined by the following claims.

```
/*
 * File Name: trecMain.c
 *
 * Author    : Jon Harman
 *
 * Brief Description: Imatron TBP reconstruction main program.
 *
 * Copyright 1993 Imatron, Inc.
 *
 * Command Line Synopsis:
 *
 * Long Description:
 *
 * Deficiencies / bugs:
 *
 * Return (status) codes, error messages:
 *
 * Abbreviations used:
 *
 * Revision History (latest updates first!): 3/12/93(jonh) New.
 */
/* 1.)  "Imported" data types and defines: */
/* 1.a.) Standard C include files  */
#include      <stdio.h>
#include      <math.h>
#include      <string.h>
#ifndef CSPI
#include      <sys/types.h>
#endif
```

```
/* 1.b.) Imatron ../include files */
#include        "../include/imatron.h"   /* first Imatron include */
#include        "../include/scanner_config.h"   /* scanner config */

/* 1.c.) Project include files                                */
#include        "trec.h"

/* 1.d.) Other include files                                  */

/* 2.) Externals defined in this file (declarations only): */
FORWARD VOID main();

/* 3.) "Imported" externals: */
/* 3.a.) Imported from standard C Library                     */
IMPORT CHAR *malloc();
IMPORT REAL atof();
#ifdef MC860
FORWARD FILE *pu_fopen();
#else
IMPORT FILE *pu_fopen();
#endif
/* 3.b.) Imported from ../xxxxx                       */

/* 3.c.) Imported from other files in this dtrectory */
/* 3.d.) Imported from elsewhere */

/* 4.) "Private" data types, defines, data and code */
EXPORT INT debug = 0, test = 0;

/* Help Message for this Program */
PRIVATE STRING HelpLines[] =
{
  "Usage: trec [Options | Parameter values]",
  "Options:",
  "    -h for this message",
  "    -c100 100ms reconstruction (default)",
  "    -c50 50ms reconstruction",
  "    -test test recon 1",
  "    -d for debug mode",
  "    -q for quiet mode",
  "    -u for non-interactive mode",
  "    -cb for two scan cone beam recon",
  "    -nfd for no folding of sinogram",
  "    -ncf for no corner filling of sinogram",
  "    -si (smooth interp if fr < 1)",
  "    -zo to zero out areas outside of recon circle",
  "Input Options:",
  "    -ps use parallel normalized sinogram for input",
  "Output Options:",
  "    -ss output filled in fan beam sinogram",
  "    -sp output rebinned (parallel) sinogram",
  "    -sc output convolved projections",
  "    -st output transformed views",
  "    -sf output Fourier image",
  "    -sm output M format Fourier image",
  "    -sr output real image",
  "    -sn output center of normed real image",
  "Parameter Values: (note space before value)",
  "    -f input (name of input fan beam sinogram)",
  "    -f2 input2 (name of second input fan beam sinogram)",
  "    -o output (name of output file)",
  "    -ker kernel (kernel number)",
  "    -r fractional recon radius (0 to 1)",
  "    -cr fractional cone beam radius (0 to 1)",
  "    -rc diam of recon circle (cm)",
  "    -s scale (scale factor for image)",
  "    -i interpolation type (0=linear, 2=cubic)",
  "    -rot rot (image rotation)",
  "    -nv nviews (fan beam views over 360)",
  "    -ns nsamps (number of samples per view)",
  "    -fa fan angle (deg)",
  "    -rw rwidth (parallel width after rebinning)",
  "    -iw output image width",
  "    -nt convolution width",
  "    -nq kb table size",
```

```
"     -b beta for gridding fcn",
"     -x0 x center of output image (-1 to 1)",
"     -y0 y center of output image (-1 to 1)",
"     -ac constant added to image",
"     -cl clip2d (parameter for 2D clipping)",
"     -fr radius of radial frequencies(0 to 1)",
"     -gr transition from first to second gridding fcn",
"     -gw half width of transition",
"     -nl set rebinning nl",
"     -nk set rebinning nk",
"     -sk skip fanbeam views",
"     -fl 1/0 flip image",
"     -npv number of phantom views",
"     -cfb cfblim",
"     -cfs cfslim",
   (STRING) NIL                  /* NIL terminator! */
};

/* Function to Print Out Help Message */
PRIVATE VOID
PrintHelp()
{
   STRING *LineP;
   /* Print Lines up to NIL terminator */
   for (LineP = HelpLines; *LineP; LineP++)
      (VOID) printf("%s\n", *LineP);
}

/* 5.) Exported Functions and Data: */

/* MAIN PROGRAM */
/* ARGSUSED *//* <---ARGSUSED is for "lint" */
EXPORT VOID
main(argc, argv)                 /* entry point of program. */
   INT argc;                     /* Number of arg strings, 1 or more */
   STRING argv[];                /* Address of array of ptrs to arg. strings */
{
   INT i, j, k, err = 0, orig, half, recontype = MS100, dorebin = 1;
   INT viewsread, minviews, nl, nsamps, minviews1;
   INT v, v0, v1, skip = 0, noni = 0, doagain = 0;
   INT savef = 0, savep = 0, savet = 0, savec = 0, saver = 0, saveflg = 0;
   INT quiet = 0, saven = 0, saves = 0, savem = 0;
   CHAR str[100], outfile[80], infile[80], fname[80], infile2[80];
   REAL reconc = -1.0, fr = -1.0, btemp;
   REAL32 tottim = 0.0, stim, tim1, tim2, tim3, tim4, tim5;
   FILE *fp;
   TREC_PARAMS trecParams;
   TREC_TABLES trecTables;
   TREC_MEMORY trecMemory;

#ifdef CSPI
   rtc_start_ ();
#endif

/* do initializations and set up defaults */
   outfile[0] = 0;
   infile[0] = 0;

/* initialize trecParams for 100ms recon */
   recontype = MS100;

/* parse the command line */
   for (i = 0; i < argc; i++)
   {
      if (!strcmp(argv[i], "-h"))
      {                          /* -h should always give help message... */
         PrintHelp();
         exit(0);
      }
      if (!strcmp(argv[i], "-d"))
         debug = 1;
      if (!strcmp(argv[i], "-da"))
         doagain = 1;
      if (!strcmp(argv[i], "-q"))
         quiet = 1;
```

```
    if (!strcmp(argv[i], "-ps"))
      dorebin = 0;
    if (!strcmp(argv[i], "-sp"))
      savep = 1;
    if (!strcmp(argv[i], "-sc"))
      savec = 1;
    if (!strcmp(argv[i], "-st"))
      savet = 1;
    if (!strcmp(argv[i], "-sf"))
      savef = 1;
    if (!strcmp(argv[i], "-sm"))
      savem = 1;
    if (!strcmp(argv[i], "-ss"))
      saves = 1;
    if (!strcmp(argv[i], "-sr"))
      saver = 1;
    if (!strcmp(argv[i], "-sn"))
      saven = 1;
    if (!strcmp(argv[i], "-t"))
      test = 1;
    if (!strcmp(argv[i], "-c100"))
      recontype = MS100;
    if (!strcmp(argv[i], "-c50"))
      recontype = MS50;
    if (!strcmp(argv[i], "-test"))
      recontype = TESTR1;
}

/*
 * initialize trecParams for recon before reading the command line
 * changes
 */
initparams(recontype, &trecParams);
for (i = 0; i < argc; i++)
{
  if (!strcmp(argv[i], "-nfd"))
     trecParams.dofold = 0;
  if (!strcmp(argv[i], "-ncf"))
     trecParams.docf = 0;
  if (!strcmp(argv[i], "-zo"))
     trecParams.zout = 1;
  if (!strcmp(argv[i], "-cb"))
     {
       trecParams.cb = 1;
       trecParams.nq = 2048;
     }
  if (!strcmp(argv[i], "-si"))
     trecParams.si = 1;
} for (i = 0; i < argc - 1; i++)
{
  if (!strcmp(argv[i], "-rc"))
     reconc = atof(argv[i + 1]);
  if (!strcmp(argv[i], "-r"))
     trecParams.reconr = atof(argv[i + 1]);
  if (!strcmp(argv[i], "-cr"))
     trecParams.coner = atof(argv[i + 1]);
  if (!strcmp(argv[i], "-c"))
     trecParams.cutoff = atof(argv[i + 1]);
  if (!strcmp(argv[i], "-b"))
     trecParams.beta = atof(argv[i + 1]);
  if (!strcmp(argv[i], "-eck"))
     trecParams.eck = atof(argv[i + 1]);
  if (!strcmp(argv[i], "-ecl"))
     trecParams.ecl = atof(argv[i + 1]);
  if (!strcmp(argv[i], "-rk"))
     trecParams.rk = atof(argv[i + 1]);
  if (!strcmp(argv[i], "-rl"))
     trecParams.rl = atof(argv[i + 1]);
  if (!strcmp(argv[i], "-x0"))
     trecParams.x0 = atof(argv[i + 1]);
  if (!strcmp(argv[i], "-y0"))
     trecParams.y0 = atof(argv[i + 1]);
  if (!strcmp(argv[i], "-xo"))
     trecParams.x0 = atof(argv[i + 1]);
```

```
        if (!strcmp(argv[i], "-yo"))
          trecParams.y0 = atof(argv[i + 1]);
        if (!strcmp(argv[i], "-fa"))
          trecParams.fanang = atof(argv[i + 1]) * PI / 180.0;
        if (!strcmp(argv[i], "-iw"))
          trecParams.iwidth = atoi(argv[i + 1]);
        if (!strcmp(argv[i], "-i"))
          trecParams.itype = atoi(argv[i + 1]);
        if (!strcmp(argv[i], "-ac"))
          trecParams.ctconst = atof(argv[i + 1]);
        if (!strcmp(argv[i], "-s"))
          trecParams.scale = atof(argv[i + 1]);
        if (!strcmp(argv[i], "-rw"))
          trecParams.rwidth = atoi(argv[i + 1]);
        if (!strcmp(argv[i], "-nt"))
          trecParams.nt = atoi(argv[i + 1]);
        if (!strcmp(argv[i], "-nq"))
          trecParams.nq = atoi(argv[i + 1]);
        if (!strcmp(argv[i], "-gr"))
          trecParams.gridr = atoi(argv[i + 1]);
        if (!strcmp(argv[i], "-gw"))
          trecParams.gridw = atoi(argv[i + 1]);
        if (!strcmp(argv[i], "-npv"))
          trecParams.npviews = atoi(argv[i + 1]);
        if (!strcmp(argv[i], "-cfb"))
          trecParams.cfblim = atoi(argv[i + 1]);
        if (!strcmp(argv[i], "-cfs"))
          trecParams.cfslim = atoi(argv[i + 1]);
        if (!strcmp(argv[i], "-nv"))
         {
          trecParams.nviews = atoi(argv[i + 1]);
          trecParams.pviews = trecParams.nviews / 2;
         }
        if (!strcmp(argv[i], "-rot"))
          trecParams.rot = atoi(argv[i + 1]);
        if (!strcmp(argv[i], "-ns"))
          trecParams.nsamps = atoi(argv[i + 1]);
        if (!strcmp(argv[i], "-pv"))
          if(!dorebin) trecParams.pviews = atoi(argv[i + 1]);
        if (!strcmp(argv[i], "-fr"))
          fr = atof(argv[i + 1]);
        if (!strcmp(argv[i], "-cl"))
          trecParams.clip2d = atof(argv[i + 1]);
        if (!strcmp(argv[i], "-fl"))
          trecParams.doflip = atoi(argv[i + 1]);
        if (!strcmp(argv[i], "-o"))
          strcpy(outfile, argv[i + 1]);
        if (!strcmp(argv[i], "-f"))
          strcpy(infile, argv[i + 1]);
        if (!strcmp(argv[i], "-f2"))
          {strcpy(infile2, argv[i + 1]);
           trecParams.cb = 1;
           trecParams.nq = 2048;
          }
        if (!strcmp(argv[i], "-ker"))
          trecParams.ktype = atoi(argv[i + 1]);
        if (!strcmp(argv[i], "-nk"))
          trecParams.nk = atoi(argv[i + 1]);
        if (!strcmp(argv[i], "-nl"))
          trecParams.nl = atoi(argv[i + 1]);
        if (!strcmp(argv[i], "-sk"))
          skip = atoi(argv[i + 1]);
       }

/* now that we have our options do some calculations based on them */

/* 47.5 is assumed to be max recon diam in cm. */
       if(reconc > 0.0) trecParams.reconr = reconc / 47.5;

trecParams.iwidth = (trecParams.iwidth / 2) * 2;      /* make even */

/* usually iwidth equals fwidth/2.  If not reconr needs to be adjusted so
          that iwidth represents a recon radius of 1 */ if(trecParams.iwidth != trecParams.fwidth / 2)
         trecParams.reconr *=  .5 * (REAL) trecParams.fwidth /
            (REAL) trecParams.iwidth;
```

```c
/* fr is the radius in Fourier space that we backproject over.
   It should equal cwidth/2 for full bandwidth.  If it is set lower
   some smoothing may be noticible if si = 1, ringing if si = 0.
   However if the original data does not have high frequencies fr
   can be set lower with si = 0 and little ringing will occur.
   Setting si = 0 and fr = .5 seems to work well for c150 data.
   This seems to avoid "fingerprint" artifacts associated with
   keeping the high frequencies.  So far no ringing has been
   noticed.
*/

/* if fr > 0 user wants to set it */
if(fr > 0.0) trecParams.fr = trecParams.cwidth * fr * .5;
else /* when iwidth < fwidth/2 some smoothing is helpful */
   if(trecParams.reconr > 1.0) trecParams.fr /= trecParams.reconr;
if((trecParams.gridr > 0) &&
    (trecParams.fr < trecParams.gridr + trecParams.gridw))
    trecParams.fr = trecParams.gridr + trecParams.gridw;
if(trecParams.fr > trecParams.cwidth / 2)
   trecParams.fr = trecParams.cwidth / 2;
trecParams.fr = (trecParams.fr / 2) * 2; /* make even, needed by spread5 */
trecParams.gridr = (trecParams.gridr / 2) * 2; /* make even */
trecParams.gridw = (trecParams.gridw / 2) * 2; /* make even */
if(trecParams.fr < 2) trecParams.fr = 2;

if(savec) saveflg += SAVEC;/* tell tbp to save convolved sino */
if(savet) saveflg += SAVET;/* tell tbp to save transformed sino */ if(!trecParams.docf)
  {
   trecParams.npviews = 0;
   trecParams.cfblim = 0;
   trecParams.cfslim = 0;
  }

/*
 * Do the setup's needed.
 */ trecTables.memtot = 0;
trecMemory.memtot = 0;

tmr_start_timesec();

if(dorebin)
  {
  /* create the tables and constants needed for rebinning */
  err = trecRBTable(&trecParams, &trecTables);
  if (err)
    {
     printf("trec: Error:%d when setting up RB tables.\n", err);
     exit(1);
    }
  }

/* create the tables and constants needed for convolution and
   backprojection */
err = trecTBPTable(&trecParams, &trecTables);
if (err)
  {
  printf("trec: Error:%d when setting up TBP tables.\n", err);
  exit(1);
  }

/* allocate the memory needed */
err = allocmem(&trecParams, &trecMemory, dorebin);
if (err)
{
  printf("trec: Error:%d when allocating memory.\n", err);
  exit(1);
} if(test)
  {
  if(trecParams.nt == 5)
    {
    printf("*** Special test mode nt 5 -> 3. norm with 5\n");
    btemp = trecParams.beta;
    trecParams.beta = 10.3;
```

```
      make_imgwin(&trecParams, trecTables.imgwin);
      trecParams.beta = btemp;
      for(i=0;i<trecParams.nq;i++)
        {
         trecTables.grtable[i * 5] = 0.0;
         trecTables.grtable[i * 5 + 4] = 0.0;
        }
     }
   if(trecParams.nt == 3)
     {
      printf("*** Special test mode nt 3 norm with 5.\n");
      trecParams.nt = 5;
      btemp = trecParams.beta;
      trecParams.beta = 10.3;
      make_imgwin(&trecParams, trecTables.imgwin);
      trecParams.nt = 3;
      trecParams.beta = btemp;
     }
  } tmr_get_timesec(&stim); /* this is the setup time */

/* these are some abbreviations */
 nl = trecParams.nl;
 nsamps = trecParams.nsamps;
 minviews = trecParams.minviews;
 minviews1 = minviews + 2 * nl; /* actual number of views needed */

/* tell what we know so far */ if (!quiet)
 {
   if (dorebin)
    {
  printf("trec. rebin fan:%g nviews:%d nsamps:%d rw:%d fd:%d rot:%d\n",
         trecParams.fanang * 180 / PI, trecParams.nviews, nsamps,
         trecParams.rwidth,trecParams.dofold, trecParams.rot);
     printf(
      "trec. mv:%d rscale:%g cf:%d c2d:%g nl:%d ecl:%g rl:%g nk:%d eck:%g\n",
            minviews, trecParams.rscale, trecParams.docf, trecParams.clip2d,
            nl, trecParams.ecl, trecParams.rl, trecParams.nk, trecParams.eck);
    }
   printf("trec. pviews:%d cwidth:%d fwidth:%d iwidth:%d flip:%d scale:%g\n",
          trecParams.pviews, trecParams.cwidth, trecParams.fwidth,
          trecParams.iwidth, trecParams.doflip, trecParams.scale);

if(!trecParams.cb)
     printf("trec. x0:%g y0:%g reconr:%g kernel:%d\n",
            trecParams.x0, trecParams.y0, trecParams.reconr,
            trecParams.ktype);
   else
     printf("trec. x0:%g y0:%g reconr:%g coner:%g kernel:%d\n",
            trecParams.x0, trecParams.y0, trecParams.reconr,
            trecParams.coner, trecParams.ktype);

printf("trec. nt:%d beta:%g nq:%d fr:%d si:%d itype:%d\n",
          trecParams.nt, trecParams.beta, trecParams.nq,
          trecParams.fr, trecParams.si, trecParams.itype);

if(trecParams.gridr > 0)
     printf("trec. gridr:%d gridw:%d\n", trecParams.gridr, trecParams.gridw);

printf("trec. Tbls:%d Mem:%d Setup time:%g\n",
          trecTables.memtot, trecMemory.memtot, stim);
 }

/* time to ask for input file, if file cannot be opened will ask again */
getinput:
 tottim = 0.0;

if (!infile[0]) /* file not specified on input line */
    {
     if (noni)
      {
       printf("trec. Error, no input file specified.\n");
       exit(1);
      }
```

```
    printf("Enter input:");
    gets(infile);
  }
strcpy(fname, infile);

/* check to see that file can be opened */
if (!(fp = pu_fopen(fname, "r")))
{
  if (noni)
  {
    printf("trec. Error opening input file %s.\n", fname);
    exit(1);
  }
  printf("trec. Cannot open file:%s\n", fname);
  infile[0] = 0;
  goto getinput;
}

/* read in the input data */
if (!quiet)
  printf("trec. Reading input sinogram.\n");
tmr_start_timesec();

/* readinput gets the data.  It knows whether the data is fan beam
   or parallel beam.
*/
viewsread = readinput(trecMemory.fansino, trecMemory.psino,
            &trecParams, dorebin, skip, fp);
if (viewsread <= 0)
  {
  printf("trec. Error reading from file %s.\n", fname);
  if (noni)  exit(1);
  infile[0] = 0;
  goto getinput;
  } tmr_get_timesec(&tim1);
/* keep track of file read time to give some idea of file read speed.
   for the MC860 in runmc mode it is very slow */
if (!quiet) printf("trec. Sino input time: %.2f \n", tim1);

if(!trecParams.cb) goto getout;
/* in cone beam mode we need two input sinograms */
getinput2:
  if (!infile2[0])
  {
    if (noni)
    {
      printf("trec. Error, no second input file specified.\n");
      exit(1);
    }
    printf("Enter second input filename:");
    gets(infile2);
  }
  strcpy(fname, infile2);

if (!(fp = pu_fopen(fname, "r")))
{
  if (noni)
  {
    printf("trec. Error opening input file %s.\n", fname);
    exit(1);
  }
  printf("trec. Cannot open file:%s\n", fname);
  infile2[0] = 0;
  goto getinput2;
}

/* read in the input data */
if (!quiet)
  printf("trec. Reading second input sinogram.\n");
tmr_start_timesec();

err = readinput(trecMemory.fansino2, trecMemory.psino2,
            &trecParams, dorebin, skip, fp);
if(err < viewsread) viewsread = err;
if (viewsread <= 0)
```

```
      {
        printf("trec. Error reading from file %s.\n", fname);
        if (noni) exit(1);
        infile[0] = 0;
        goto getinput2;
      } tmr_get_timesec(&tim1);
    if (!quiet) printf("trec. Sino2 input time: %.2f \n", tim1);

/* before doing the recon we check that the output file can be
   opened.
*/ getout:
    if (!outfile[0]) /* outfile not specified on command line */
    {
      if (noni)
      {
        printf("trec. Error, no output file specified.\n");
        exit(1);
      }
      sprintf(str, "%s.tbp", infile); /* provide a default output name */
      printf("Enter output file name[%s]:", str);
      gets(outfile);
      if (!strlen(outfile))
        strcpy(outfile, str);
    }
    strcpy(fname, outfile);

if (!(fp = pu_fopen(fname, "w"))) /* check that it can be opened */
    {
      if (noni)
      {
        printf("trec. Error opening output file %s.\n", fname);
        exit(1);
      }
      printf("trec. Cannot open file:%s\n", fname);
      goto reset;
    } if (!quiet)
     {printf("trec. Input:%s Views read:%d Output:%s\n",
            infile, viewsread, outfile);
      if(trecParams.cb) printf("Second input:%s\n", infile2);
     }

/* Begin the reconstruction */ tmr_start_timesec();

if (dorebin)
      {
        /* Rebinning step: go from fan beam sinogram in fansino to a
           parallel beam sinogram in psino.
           We need 180 + fan + 2*nl views.  The 2 * nl are needed for the
           beta to theta interpolation, nl views at the beginning and end.
           Since we have read in at least 180 + fan we can create any missing
           views from data already read in.
           In the case of un-corner-filled data there are phantom views at
           the beginning and end of the sinogram plus the empty corners.
           At the present we merely fill in the nl phantom views near the
           good views and we don't fill in any of the corners.  This is not
           optimal and needs work.
        */ v0 = trecParams.npviews;
        v1 = v0 + nl;

for (v = v0; v < v1; v++)
          {
            fanfillin(trecMemory.fansino, v, nl, viewsread, trecParams.nviews,
                      nsamps, trecParams.fanang);

if(trecParams.cb)
              fanfillin(trecMemory.fansino2, v, nl, viewsread,
                        trecParams.nviews, nsamps, trecParams.fanang);
```

```
  } v0 = viewsread + nl - trecParams.npviews;
v1 = v0 + nl;
if(v1 > minviews1) v1 = minviews1;

for (v = v0; v < v1; v++)
  {
    fanfillin(trecMemory.fansino, v, nl, viewsread, trecParams.nviews,
              nsamps, trecParams.fanang);
    if(trecParams.cb)
      fanfillin(trecMemory.fansino2, v, nl, viewsread,
                trecParams.nviews, nsamps, trecParams.fanang);
  } if (saves)
  {
    printf("Saving filled in sinogram. width:%d length:%d\n",
           nsamps, minviews1);
    i = fwrite(trecMemory.fansino, sizeof(REAL32),
               minviews1 * nsamps, fp);
    if (i != minviews1 * nsamps)
      printf("trec. Error writing to file:%s\n", outfile);
    fclose(fp);
    exit(0);
  }

/* do the rebinning */ err = trecRebin(&trecParams, &trecTables, &trecMemory);
tmr_get_timesec(&tim1);
tottim = tim1;
if (!quiet) printf("trec. Rebin time: %.2f \n", tim1);

if (err)
  {
    printf("trec. Error:%d when rebinning.\n", err);
    exit(1);
  } if (savep)
  {
    printf("Saving rebinned sinogram. width:%d length:%d\n",
           trecParams.rwidth, trecParams.pviews);
    i = fwrite(trecMemory.psino, sizeof(REAL32),
               trecParams.rwidth * trecParams.pviews, fp);
      if (i != trecParams.rwidth * trecParams.pviews)
        printf("trec. Error writing to file:%s\n", outfile);
      fclose(fp);
      if(trecParams.cb)
        {
          sprintf(str, "%s.l2", infile);
          printf("trec. Enter second output file name[%s]:", str);
          gets(outfile);
          if (!strlen(outfile)) strcpy(outfile, str);
          strcpy(fname, outfile);

if (!(fp = pu_fopen(fname, "w")))
            {
              printf("trec. Cannot open file:%s\n", fname);
              exit(1);
            }
          i = fwrite(trecMemory.psino2, sizeof(REAL32),
                     trecParams.rwidth * trecParams.pviews, fp);
          if (i != trecParams.rwidth * trecParams.pviews)
            printf("trec. Error writing to file:%s\n", outfile);
          fclose(fp);
        }
    exit(0);
  }

}/* if dorebin */

/* the convolved and trensformed sinos are saved from inside tbp */
if (savec)
  printf("trec. Saving convolved sinogram. width:%d length:%d\n",
         trecParams.rwidth, trecParams.pviews);
```

```
  if (savet)
     printf("trec. Saving transformed sinogram. width:%d length:%d\n",
            trecParams.cwidth, trecParams.pviews);

tmr_start_timesec();

tbp(&trecMemory, &trecTables, &trecParams, saveflg, fp);

if(savec || savet) /* exit in this case */
   {
    fclose(fp);
    exit(0);
   } tmr_get_timesec(&tim2);
  tottim += tim2;
  if(!quiet) printf("trec. TBP   time:%.2f\n", tim2);

if (savef)
  {
    if (!quiet)
      printf("trec. Saving Fourier image. width:%d\n", trecParams.fwidth);
    i = fwrite(trecMemory.fimage, sizeof(REAL32),
            trecParams.fwidth * (trecParams.fwidth + 2), fp);
    if (i != trecParams.fwidth * (trecParams.fwidth + 2))
       printf("trec. Error writing to file:%s\n", fname);
    fclose(fp);
    exit(0);
  }

/* do the inverse 2D FFT */ tmr_start_timesec();

/* get the Fourier image into the format required by rfft2d */
  mformat(trecMemory.fimage, trecParams.fwidth, trecParams.fwidth);
    if (savem)
    {
      if (!quiet)
        printf("trec. Saving M format Fourier image. width:%d\n",
            trecParams.fwidth);
      i = fwrite(trecMemory.fimage, sizeof(REAL32),
            trecParams.fwidth * trecParams.fwidth , fp);
      if (i != trecParams.fwidth * trecParams.fwidth)
          printf("trec. Error writing to file:%s\n", fname);
      fclose(fp);
      exit(0);
    }

/* do the 2D real inverse FFT. We need to "flip" the image */
    rfft2dsh(trecMemory.fimage, trecParams.fwidth, trecParams.fwidth, 1, 1, 0);

tmr_get_timesec(&tim3);
    tottim += tim3;

if(!quiet) printf("trec. 2DFFT time: %.2f\n", tim3);

if (saver)
    {
      if (!quiet)
        printf("trec. Saving real image. width:%d\n", trecParams.fwidth);
      i = fwrite(trecMemory.fimage, sizeof(REAL32),
            trecParams.fwidth * trecParams.fwidth, fp);
      if (i != trecParams.fwidth * trecParams.fwidth)
          printf("trec. Error writing to file:%s\n", fname);
      fclose(fp);
      exit(0);
    } tmr_start_timesec();

/* final step is to divide by the transform of the convolution
     function, clip  and fix to an integer */
  norm_image(&trecTables, &trecMemory, &trecParams, debug | saven);

tmr_get_timesec(&tim4);
  tottim += tim4;
```

```
    if(!quiet) printf("trec. Norm  time: %.2f\n", tim4);

if(!quiet) printf("trec. Total time:%.2f\n", tottim);
    if(debug || saven)
      printf("trec. Saving real %dx%d image.\n", trecParams.iwidth, trecParams.iwidth);
    if(debug || saven)
      i = fwrite(trecMemory.image, sizeof(REAL32),
             trecParams.iwidth * trecParams.iwidth, fp);
    else
      i = fwrite(trecMemory.image, sizeof(INT16),
             trecParams.iwidth * trecParams.iwidth, fp);

if (i != trecParams.iwidth * trecParams.iwidth)
    {
      printf("trec. Error writing to file:%s\n", fname);
      exit(5);
    } fclose(fp);
    if (!quiet)
      printf("trec. Finished.\n");
reset:
    outfile[0] = 0;
    infile[0] = 0;
    infile2[0] = 0;

if(doagain) goto getinput;/* mainly to test ability to do repeated recons */

/* 5d.) Termination Code: */
    exit(0);
}                          /* END main */

/* #ifdef MC860 */
EXPORT
FILE * pu_fopen(str1, str2)
  CHAR *str1, *str2;
{
  return (fopen(str1, str2));
}
/* #endif */

/* little program to initialize all the parameters we need */
INT
initparams(recontype, trecParams)
  INT recontype;
  TREC_PARAMS *trecParams;
{
 /* the default is MS100 */
 trecParams->nviews = 1440;
 trecParams->nsamps = SMPL_PER_VIEW_100;
 trecParams->pviews = 720;
 trecParams->rwidth = 1024;
 trecParams->dofold = 1;
 trecParams->docf = 1;
 trecParams->doflip = 1;
 trecParams->nl = 3;
 trecParams->nk = 6;
 trecParams->rot = 360;
 trecParams->si = 0;
 trecParams->cb = 0;
 trecParams->reverse = 0;
 trecParams->fwidth = 1024;
 trecParams->cwidth = 2048;
 trecParams->npviews = 12;
 trecParams->cfslim = 520;
 trecParams->cfblim = 180;
 trecParams->fr = 512;
 trecParams->gridr = -1;
 trecParams->gridw = 0;
 trecParams->iwidth = 512;
 trecParams->nt = 5;
 trecParams->nq = 1024;
 trecParams->cutoff = -1.0;
```

```
    trecParams->beta = 10.3;
    trecParams->ktype = 0;
    trecParams->itype = 0;
    trecParams->x0 = 0.0;
    trecParams->y0 = 0.0;
    trecParams->ctmin = 0.0;
    trecParams->ctmax = 4095.0;
    trecParams->ctconst = 0.0;
    trecParams->zout = 0;
    trecParams->fanang = FAN_ANGLE_100 * PI / 180.;
    trecParams->reconr = 1.0;
    trecParams->coner = .5;
    trecParams->cbdist = .03;
    trecParams->rscale = 4.2296;
    trecParams->scale = 1.0;
    trecParams->sampoffset = 0.0;
    trecParams->clip2d = 0.02;
    trecParams->tshift = 0.0;
    trecParams->ecl = 1.0;
    trecParams->eck = 1.0;
    trecParams->rl = 1.15;
    trecParams->rk = 1.0;

switch (recontype)
    {
    case MS50:
       trecParams->nviews = 720;
       trecParams->nsamps = SMPL_PER_VIEW_50;
       trecParams->pviews = 360;
       trecParams->rwidth = 512;
       trecParams->docf = 2;
       trecParams->nl = 2;
       trecParams->nk = 4;
       trecParams->rot = 180;
       trecParams->fwidth = 512;
       trecParams->cwidth = 1024;
       trecParams->fr = 320;
       trecParams->gridr = -1;
       trecParams->gridw = 0;
       trecParams->iwidth = 256;
       trecParams->fanang = FAN_ANGLE_50 * PI / 180.;
       trecParams->clip2d = 0.08;
       trecParams->npviews = 6;
       trecParams->cfslim = 260;
       trecParams->cfblim = 90;
       break;
    case TESTR1:
       trecParams->nviews = 512;
       trecParams->nsamps = 256;
       trecParams->pviews = 256;
       trecParams->rwidth = 256;
       trecParams->rot = 483;
       trecParams->dofold = 1;
       trecParams->docf = 0;
       trecParams->doflip = 0;
       trecParams->nl = 2;
       trecParams->nk = 3;
       trecParams->fwidth = 512;
       trecParams->cwidth = 512;
       trecParams->fr = 256;
       trecParams->gridr = -1;
       trecParams->gridw = 0;
       trecParams->iwidth = 256;
       trecParams->fanang = 42. * PI / 180.;
       trecParams->rscale = 1.0;
       trecParams->clip2d = 0.0;
       trecParams->npviews = 0;
       trecParams->cfslim = 0;
       trecParams->cfblim = 0;
       break;
    }
    return(0);
}
```

```
/*
 * File Name: trecTbp.c
 *
 * Author    : Jon Harman
 *
 * Brief Description: TBP functions for trec.
 *
 * Copyright 1993 Imatron, Inc.
 *
 * Command Line Synopsis:
 *
 * Long Description:
 *
 * Deficiencies / bugs:
 *
 * Return (status) codes, error messages:
 *
 * Abbreviations used:
 *
 * Revision History (latest updates first!): 3/15/93(jonh) New.
 */
/* LINTLIBRARY *//* suppresses some unneeded lint messages */

/* 1.) "Imported" data types and defines: */
/* 1.a.) Standard C include files   */
#include         <stdio.h>
#include         <math.h>
#include         <string.h>
#ifndef CSPI
#include         <sys/types.h>
#endif
#ifdef     MC860
#include         <mcos.h>
#include         <sal_defs.h>
endif /* 1.b.) Imatron ../include files */
include         "../include/imatron.h"   /* first Imatron include */

/* 1.c.) Project include files                                    */
#include         "trec.h"

/* 1.d.) Other include files                                      */

/* 2.) Externals defined in this file (declarations onry): */

/* 3.) "Imported" externals: */
/* 3.a.) Imported from standard C Library                         */
IMPORT CHAR *malloc();

/* 3.b.) Imported from ../xxxxx                        */

/* 3.c.) Imported from other files in this dtrectory */
/* 3.d.) Imported from elsewhere */
IMPORT INT debug;

/* 4.) "Private" data types, defines, data and code */
#ifdef MC860
IMPORT REAL32 salcache[4];
#else
#define SAL_NC  1
#define SAL_NCC 1
#define SAL_CCN 1
#define SAL_CNC 1
#define SAL_CN  1
#define SAL_CC  1
#define SAL_C   1
PRIVATE REAL32 salcache[2048];

endif

PRIVATE INT ncalc = 0;
PRIVATE REAL stab[NCALC],itab[NCALC];

/* 5.) Exported Functions and Data: */

/* This is the main transform domain backprojection routine.
   It goes through the views and backprojects them using
```

```
    Fourier techniques (also called gridding.)
    My main reference for this technique is:
    Backprojection by Upsampled Fourier Series Expansion
    and Interpolated FFT in vol 1 of IEEE trans on Image Processing.
    By: Makoto Tabei and Mitsuhiro Ueda
*/
EXPORT INT
   tbp(trecMemory, trecTables, trecParams, saveflg, fp)
TREC_MEMORY *trecMemory;
TREC_TABLES *trecTables;
TREC_PARAMS *trecParams;
INT saveflg; /* indicated if any diagnostic results should be saved */
FILE *fp;    /* file for saving diagnostic results */

{INT i, j, k, v, pv, qv, rv, rwidth, nr, vw, cw, fr;
 REAL32 *psino, *psino2;
 REAL32 *view1, *view2, *view3, *view4;
 REAL32 *cbview1, *cbview2, *cbview3, *cbview4;
 REAL vangle, pvangle, qvangle, rvangle;
 CHAR str[100];

/* some abbreviations */
 vw = trecParams->rwidth;   /* view width */
 cw = trecParams->cwidth;   /* convolution width */
 nr = trecParams->cwidth / 2;
 fr = trecParams->fr;
 psino = trecMemory->psino;
 psino2 = trecMemory->psino2;
 view1 = trecMemory->view1;
 view2 = trecMemory->view2;
 view3 = trecMemory->view3;
 view4 = trecMemory->view4;
 cbview1 = trecMemory->cbview1;
 cbview2 = trecMemory->cbview2;
 cbview3 = trecMemory->cbview3;
 cbview4 = trecMemory->cbview4;

/* zero out the Fourier image */
 init_img(trecMemory->fimage, trecParams->fwidth);

/* v is the view variable */
 for(v = 0;v < trecParams->pviews / 4; v++)
  { if(debug)
    {printf("Enter v[%d]:",v);
     gets(str);
     if(strlen(str)) v = atoi(str);
    } vangle = PI * (REAL) v / (REAL) trecParams->pviews;

/* pv is the view at PI/2 - v */
   pv = trecParams->pviews / 2 - v;
   if(!v) pv = trecParams->pviews / 4; /* special case */

/* qv is the view at PI/2 + v */
   qv = trecParams->pviews / 2 + v;
   if(!v) qv = trecParams->pviews / 2; /* special case */
   /* rv is the view at PI/2 + v */
   rv = trecParams->pviews - v;
   if(!v) rv = 3 * trecParams->pviews / 4; /* special case */ if(debug) {pv = v; qv = v; rv = v;printf("vangle:%g\n",vangle*180/PI);} pvangle = PI * (REAL) pv / (REAL) trecParams->pviews;
   qvangle = PI * (REAL) qv / (REAL) trecParams->pviews;
   rvangle = PI * (REAL) rv / (REAL) trecParams->pviews;

vclr(view1 + vw, 1, cw - vw);
   vclr(view2 + vw, 1, cw - vw);
   vclr(view3 + vw, 1, cw - vw);
   vclr(view4 + vw, 1, cw - vw);
   if(trecParams->cb)
```

```
    {
      vclr(cbview1 + vw, 1, cw - vw);
      vclr(cbview2 + vw, 1, cw - vw);
      vclr(cbview3 + vw, 1, cw - vw);
      vclr(cbview4 + vw, 1, cw - vw);
    } vmov(psino + v * vw, 1, view1, 1, vw);
    vmov(psino + pv * vw, 1, view2, 1, vw);
    vmov(psino + qv * vw, 1, view3, 1, vw);
    vmov(psino + rv * vw, 1, view4, 1, vw);
    if(trecParams->cb)
     {
      vmov(psino2 + v * vw, 1, cbview1, 1, vw);
      vmov(psino2 + pv * vw, 1, cbview2, 1, vw);
      vmov(psino2 + qv * vw, 1, cbview3, 1, vw);
      vmov(psino2 + rv * vw, 1, cbview4, 1, vw);
     } if(debug) /* only want one copy of view */
     {vclr(view2, 1, cw);
      vclr(view3, 1, cw);
      vclr(view4, 1, cw);
      if(trecParams->cb)
        {vclr(cbview2, 1, cw);
         vclr(cbview3, 1, cw);
         vclr(cbview4, 1, cw);
        }
     }

/* do the convolution by the parallel beam kernel */ kerconv(view1, trecTables->kernel, cw);
   kerconv(view2, trecTables->kernel, cw);
   kerconv(view3, trecTables->kernel, cw);
   kerconv(view4, trecTables->kernel, cw);
   if(trecParams->cb)
    {
     kerconv(cbview1, trecTables->kernel, cw);
     kerconv(cbview2, trecTables->kernel, cw);
     kerconv(cbview3, trecTables->kernel, cw);
     kerconv(cbview4, trecTables->kernel, cw);
    } if (saveflg & SAVEC)  /* write out convolved sino */
     {fwrite(view1, sizeof(REAL32), vw, fp);
      fwrite(view2, sizeof(REAL32), vw, fp);
      fwrite(view3, sizeof(REAL32), vw, fp);
      fwrite(view4, sizeof(REAL32), vw, fp);
      if(trecParams->cb)
        {fwrite(cbview1, sizeof(REAL32), vw, fp);
         fwrite(cbview2, sizeof(REAL32), vw, fp);
         fwrite(cbview3, sizeof(REAL32), vw, fp);
         fwrite(cbview4, sizeof(REAL32), vw, fp);
        }
      continue;
     }

/* now circularly shift the convolved view */ cshift(view1, vw, nr);
cshift(view2, vw, nr);
cshift(view3, vw, nr);
cshift(view4, vw, nr);
if(trecParams->cb)
  {
   cshift(cbview1, vw, nr);
   cshift(cbview2, vw, nr);
   cshift(cbview3, vw, nr);
   cshift(cbview4, vw, nr);
  }

/* transform */
rfft(view1, nr, 1);
rfft(view2, nr, 1);
rfft(view3, nr, 1);
```

```
   rfft(view4, nr, 1);
   if(trecParams->cb)
    {
      rfft(cbview1, nr, 1);
      rfft(cbview2, nr, 1);
      rfft(cbview3, nr, 1);
      rfft(cbview4, nr, 1);
    }

/* fold around nr */
   foldview(view1, nr);
   foldview(view2, nr);
   foldview(view3, nr);
   foldview(view4, nr);
   if(trecParams->cb)
    {
      foldview(cbview1, nr);
      foldview(cbview2, nr);
      foldview(cbview3, nr);
      foldview(cbview4, nr);
    }

/* multiply by the interpolation filter */ vmul(view1, 1, trecTables->ifil, 1, view1, 1, fr * 2);
   vmul(view2, 1, trecTables->ifil, 1, view2, 1, fr * 2);
   vmul(view3, 1, trecTables->ifil, 1, view3, 1, fr * 2);
   vmul(view4, 1, trecTables->ifil, 1, view4, 1, fr * 2);
   if(trecParams->cb)
    {
      vmul(cbview1, 1, trecTables->ifil, 1, cbview1, 1, fr * 2);
      vmul(cbview2, 1, trecTables->ifil, 1, cbview2, 1, fr * 2);
      vmul(cbview3, 1, trecTables->ifil, 1, cbview3, 1, fr * 2);
      vmul(cbview4, 1, trecTables->ifil, 1, cbview4, 1, fr * 2);
    }

/* perform a shift by multiplying in the Fourier domain
      the shift works on 2 (plus 2 cone beam) views at once.
      they must satisfy vangle2 = PI - vangle1
   */ if(v != 0)
    {
      shifttransv(trecTables, trecMemory, trecParams, vangle, v,
               view1, view4, cbview1, cbview4);
      shifttransv(trecTables, trecMemory, trecParams, pvangle, pv,
               view2, view3, cbview2, cbview3);
    }
   else
    {
      shifttransv(trecTables, trecMemory, trecParams, vangle, v,
               view1, view3, cbview1, cbview3);
      shifttransv(trecTables, trecMemory, trecParams, pvangle, pv,
               view2, view4, cbview2, cbview4);
    }

/* write out transformed sino */ if (saveflg & SAVET)
   {fwrite(view1, sizeof(REAL32), cw, fp);
    fwrite(view2, sizeof(REAL32), cw, fp);
    fwrite(view3, sizeof(REAL32), cw, fp);
    fwrite(view4, sizeof(REAL32), cw, fp);
    if(trecParams->cb)
      {fwrite(cbview1, sizeof(REAL32), cw, fp);
       fwrite(cbview2, sizeof(REAL32), cw, fp);
       fwrite(cbview3, sizeof(REAL32), cw, fp);
       fwrite(cbview4, sizeof(REAL32), cw, fp);
      }
    continue;
   }

/* finally we do the backprojection.  fbackp uses symmetry of the
   sines and cosines of our angles to save computation.  Thus it
   does all four views at once.  fbackpcb could do the same, but
   the complication is tremedous.  Maybe sometime in the future.
```

```
  */
  if(!trecParams->cb)
    fbackp(trecTables, trecMemory, trecParams, vangle, v);
  else
    {
    ncalc = 0;
    fbackpcb(trecTables, trecMemory, trecParams, vangle, view1, cbview1, 0);
    fbackpcb(trecTables, trecMemory, trecParams, pvangle, view2, cbview2, 0);
    fbackpcb(trecTables, trecMemory, trecParams, qvangle, view3, cbview3, 1);
    fbackpcb(trecTables, trecMemory, trecParams, rvangle, view4, cbview4, 1);
    if(ncalc > NCALC)
       printf("trec. Error!! ncalc:%d v:%d\n",ncalc, v);
    } if(debug) break;

}/* for v = ... */ return(0);
}

/* fold view.  This effectively doubles the frequency range of the
view, and eliminates ringing artifacts.  To make the higher frequencies
we reflect and conjugate the view around nr in the freq domain.
*/
INT
foldview(view, nr)
REAL32 *view;
INT nr;
{INT i;REAL32 neg1 = -1.0;

view[0] *= .5;
 view[nr] = view[1];/* rfft format puts real part of nr at 1 */
 view[1] = 0.0; /* don't bother with this term */
 view[nr + 1] = 0.0;/* true due to real fft symmetry */
 vmov(view + nr - 2, -2, view + nr + 2, 2, nr/2 - 1);
 vsmul(view + nr - 1, -2, &neg1, view + nr + 3, 2, nr/2 - 1);
/*
 for(i=1;i < nr/2; i++)
   {
    view[nr + i * 2] = view[(nr - i * 2)];
    view[nr + i * 2 + 1] = -view[(nr - i * 2) + 1];
   }
*/
 return(0);

}

/* kerconv: do the convolution by transforming , multiplying, and
   transforming back.  cw is the width of the padded view.  The view
   must be padded to at least twice it's length to avoid errors in
   convolution.
*/

/* do the convolution with the kernel by multiplying in the Fourier domain */
INT
kerconv(view, kernel, cw)
REAL32 *view, *kernel;
INT cw;
{
 /* forward rfft */
 rfft(view, cw, 1);

/* do the convolution in freq domain by a complex multiply */
 cvmul(view + 2, 2, kernel + 2, 2, view + 2, 2, (cw / 2) - 1, 1);

/* these points are special due to real fft format */
 view[0] *= kernel[0];
 view[1] *= kernel[1];

/* reverse rfft */
 rfft(view, cw, -1);

return(0);
```

}

```c
/* circularly shift the convolved view by 180 degrees */
INT
    cshift(view, vw, nr)
REAL32 *view;
INT vw, nr;
{

/* save the first half */
 vmov(view, 1, view + nr, 1, vw / 2);

/* move second half to first half */
 vmov(view + vw / 2, 1, view, 1, vw / 2);

/* move saved first half to second half */
 vmov(view + nr, 1, view + nr - vw / 2, 1, vw / 2);

if(nr > vw)  vclr(view + vw / 2, 1, nr - vw);

return(0);
}

/* Transform domain backprojection routine.  This routine backprojects
    four views at once.  One is at vangle, the others at PI/2-vangle,
    PI/2 + vangle. PI-vangle.
    This allows us to save a little calculation by making use of the
    symmetries of sines and cosines.  The first view (view0 = 0) is a
    special case.
    The backprojection is done in the transform domain by convolving
    the view with an nt x nt convolving function then adding into the
    2D Fourier matrix.  For each complex point in the view we need to
    calculate the coordinates (kx0,ky0) in the big matrix of the little
    nt x nt matrix.  We also calculate the coefficients of the little
    matrix.  Since it is separable, we need two nt length vectors: vx and
    vy.  These use values precalculated and saved in the grtable.
*/

INT
    fbackp(trecTables, trecMemory, trecParams, vangle, view0)
TREC_TABLES *trecTables;
TREC_MEMORY *trecMemory;
TREC_PARAMS *trecParams;
REAL vangle;
INT view0;
{INT i, fr;
 REAL rsin, rcos;
 REAL32 *grtable;
 INT32 *vkx0 = trecMemory->vkx0,*vky0 = trecMemory->vky0;
 REAL32 **vvx = trecMemory->vvx, **vvy = trecMemory->vvy;
 REAL32 *vs = trecMemory->vs;
 REAL32 *view1, *view2, *view3, *view4;

view1 = trecMemory->view1; /* the view at vangle: (rcos, -rsin) */
 view2 = trecMemory->view2; /* the view at PI/2 - vangle: (rsin, -rcos) */
 view3 = trecMemory->view3; /* the view at PI/2 + vangle: (-rsin, -rcos) */
 view4 = trecMemory->view4; /* the view at PI - vangle: (-rcos, -rsin) */
 if(trecParams->doflip && (view0 != 0))
  {/* flip causes first coord to get negated */
   view1 = trecMemory->view4; /* the view at PI - vangle: (rcos, -rsin) */
   view2 = trecMemory->view3; /* the view at PI/2 + vangle: (rsin, -rcos)*/
   view3 = trecMemory->view2; /* the view at PI/2 - vangle: (-rsin, -rcos) */
   view4 = trecMemory->view1; /* the view at vangle: (-rcos, -rsin)*/
  }

/* fr is the length (in complex elements) of the view that we backproject */
fr = trecParams->fr;
grtable = trecTables->grtable;

if(view0 != 0)
 {
  rcos = trecParams->reconr * 2.0 * cos(vangle);
  rsin = trecParams->reconr * 2.0 * sin(vangle);
```

```
    /* calculate the matrix coords and the coefficients for -rcos and -rsin */
    calccoord(trecParams, grtable, 0.0, -rcos, vkx0, vvx, vs);
    calccoord(trecParams, grtable, 0.0, -rsin, vky0, vvy, vs);

/* now do the gridding into the matrix */

/* view4 is at (-rcos, -rsin) */
    vgrid(trecParams, trecMemory, trecTables, vkx0, vky0, vvx, vvy, view4);
    /* view3 is at (-rsin, -rcos) */
    vgrid(trecParams, trecMemory, trecTables, vky0, vkx0, vvy, vvx, view3);

/* view2 is at (rsin, -rcos) */
    /* have to calculate rsin, stash results in view3 and view4 */
    calccoord(trecParams, grtable, 0.0, rsin, view3, view4, vs);
    vgrid(trecParams, trecMemory, trecTables, view3, vkx0, view4, vvx, view2);
    /* view1 is at (rcos, -rsin) */
    /* have to calculate rcos, stash results in view3 and view4 */
    calccoord(trecParams, grtable, 0.0, rcos, view3, view4, vs);
    vgrid(trecParams, trecMemory, trecTables, view3, vky0, view4, vvy, view1);
  }
  else
  {
    /* view 0 is a special case. here we store
       vangle = 0 in view1 at (1,0)      flip: (-1,0)
       vangle = PI/4 in view2 at (.707,-.707) flip: (-.707,-.707)
       vangle = PI/2 in view3 at (0,-1)  flip: (0,-1)
       vangle = 3PI/2 in view4 at (-.707,-.707) flip:(.707,-.707)
    */ if(!trecParams->doflip)
    {
      rcos = trecParams->reconr * 2.0;
      rsin = 0.0;
      calccoord(trecParams, grtable, 0.0, rcos, vkx0, vvx, vs);
      calccoord(trecParams, grtable, 0.0, rsin, vky0, vvy, vs);
      vgrid(trecParams, trecMemory, trecTables, vkx0, vky0, vvx, vvy, view1);
      calccoord(trecParams, grtable, 0.0, -rcos, vkx0, vvx, vs);
      vgrid(trecParams, trecMemory, trecTables, vky0, vkx0, vvy, vvx, view3);
      rcos = trecParams->reconr * 2.0 * cos(PI / 4.0);
      rsin = trecParams->reconr * 2.0 * sin(PI / 4.0);
      calccoord(trecParams, grtable, 0.0, rcos, vkx0, vvx, vs);
      calccoord(trecParams, grtable, 0.0, -rsin, vky0, vvy, vs);
      vgrid(trecParams, trecMemory, trecTables, vkx0, vky0, vvx, vvy, view2);
      vgrid(trecParams, trecMemory, trecTables, vky0, vky0, vvy, vvy, view4);
    }
    else
    {
      rcos = -trecParams->reconr * 2.0;
      rsin = 0.0;
      calccoord(trecParams, grtable, 0.0, rcos, vkx0, vvx, vs);
      calccoord(trecParams, grtable, 0.0, rsin, vky0, vvy, vs);
      vgrid(trecParams, trecMemory, trecTables, vkx0, vky0, vvx, vvy, view1);
      vgrid(trecParams, trecMemory, trecTables, vky0, vkx0, vvy, vvx, view3);
      rcos = trecParams->reconr * 2.0 * cos(PI / 4.0);
      rsin = trecParams->reconr * 2.0 * sin(PI / 4.0);
      calccoord(trecParams, grtable, 0.0, -rcos, vkx0, vvx, vs);
      calccoord(trecParams, grtable, 0.0, rsin, vky0, vvy, vs);
      vgrid(trecParams, trecMemory, trecTables, vkx0, vkx0, vvx, vvx, view2);
      vgrid(trecParams, trecMemory, trecTables, vky0, vkx0, vvy, vvx, view4);
    }

} return(0);
}

/* Transform domain cone beam backprojection routine.
   This routine backprojects two views (the cone beam pair at vangle)
   at once. The goal of the cone beam algorithm is to weight each
   view with a linear weighting function during backprojection. It does
   this by convolving the view with a simple weight function in the
   Fourier domain. In fact we use a sine function near the zero crossing,
   but very much zoomed in, to approximate a linear weighting function in
   the spatial domain. This requires a convolution by a two point function.
   One point is at (sx0,sy0) with complex value cmul1.re,cmul1.im.
```

The other is at (-sx0,-sy0) and has complex value cmul1.re, -cmul1.im.
The second view has the same vangle but is shaded oppositely, i.e.
the shading direction is the same, but the weighing function has
opposite slope. We save time by using the same vspread routine to do
both views: we just add the two views before vspread.
*/

```
INT
   fbackpcb(trecTables, trecMemory, trecParams, vangle, view1, view2, opp)
TREC_TABLES *trecTables;
TREC_MEMORY *trecMemory;
TREC_PARAMS *trecParams;
REAL vangle;
REAL32 *view1, *view2;
INT opp;
{INT i, fr, cindex, cwidth = trecParams->cwidth;
 REAL sx0, sy0, rsin, rcos, cbdist, cbmult, va1, va2, tsh, cbscale;
 INT32 *vkx0 ,*vky0;
 REAL32 **vvx, **vvy;
 REAL32 *cbtemp1 = trecMemory->cbtemp1, *cbtemp2 = trecMemory->cbtemp2;
 COMPLEX32 cmul1, cmul2;

fr = trecParams->fr;

/* the parameters that govern the cone beam shading are:
     cbscale: a scale factor that reflects the desired slope of the shade
              function. For reconr = 1 and coner = 1 the shade function
              will go from 0 to 1 over iwidth (center half of fimage).
              This corresponds to a cbscale of 1. For reconr = .5, coner
              = 1.0 we want the shade function to go from .25 to .75
              so cbscale = .5.
     cbdist:  distance from 0 of each cb term. If cbdist = 1 then the
              shade function will be a sine wave with period equal to
              fwidth (=2 * iwidth). A smaller cbdist will result in a
              larger period. We want the shading function to be
              approximately linear so we choose a very small cbdist (.03)
              to begin with.  (nq limits the smallness of cbdist)
              We use cbdist to implement cbscale: zooming in on the sine
              wave results in a lower slope for the shading function.
     cbmult:  This is a scale factor. It is used to establish the basic scale
              for reconr = coner = 1.  Then cbdist is used to further scale
              the shading function.
     tsh:     An angular shift to get the sine wave into the right position.
              For x0 = 0 and y0 = 0 this means put the zero crossing of the
              shading at the center of the image. In general the zero
              crossing must be adjusted to reflect the position of the
              center of the recon circle in the image.
 */ cbscale = trecParams->reconr / trecParams->coner;
 cbdist = trecParams->cbdist * cbscale;
 cbmult = .5 / sin(trecParams->cbdist * PI / 2.0);

va1 = vangle + PI; /* shading angle for view 1 */
 va2 = vangle; /* shading angle for view 2 */ if(opp) /* opp means shade oppositely: true for second half of views */
   {va1 = vangle;
    va2 = vangle + PI;
   } if(trecParams->doflip) {va1 = -va1;va2 = -va2;}

/* (rcos,rsin) is the angle the view is backprojected at. It is the same
    as the non cone beam case */
 rcos = trecParams->reconr * 2.0 * cos(vangle);
 if(trecParams->doflip) rcos = -rcos;
 rsin = -trecParams->reconr * 2.0 * sin(vangle);

/* (sx0,sy0) is a vector offset from the nominal position (0,0)
    of the backprojection.
 */ sx0 = sin(va1) * cbdist;
 sy0 = cos(va1) * cbdist;
```

```
tsh = trecParams->cbdist * PI / 2.0 *
   (1.0 + (sin(va1) * trecParams->x0 + cos(va1) * trecParams->y0) * cbscale);

cmul1.re = cbmult * sin(tsh);
cmul1.im = -cbmult * cos(tsh);
  if(debug) printf("vangle:%g rcos:%g rsin:%g val:%g sx0:%g sy0:%g\n",
                 vangle * 180 / PI, rcos, rsin,
                 va1 * 180 / PI, sx0, sy0);
  if(debug) printf("cbdist:%g tsh:%g cm1.re:%g cm1.im:%g\n",
                 cbdist, tsh * 180 / PI, cmul1.re, cmul1.im);

cbcc(trecParams, trecTables, trecMemory, sx0, rcos, &cindex);
vkx0 = (INT32 *) trecMemory->cbcoords + cindex * cwidth;
vvx = (REAL32 **) vkx0 + cwidth / 2;
cbcc(trecParams, trecTables, trecMemory, sy0, rsin, &cindex);
vky0 = (INT32 *) trecMemory->cbcoords + cindex * cwidth;
vvy = (REAL32 **) vky0 + cwidth / 2;

tsh = trecParams->cbdist * PI / 2.0 *
   (1.0 + (sin(va2) * trecParams->x0 + cos(va2) * trecParams->y0) * cbscale);

cmul2.re = cbmult * sin(tsh);
cmul2.im = cbmult * cos(tsh); /* note the difference */ if(debug)
   printf("cm1: %g %g cm2:%g %g\n",cmul1.re,cmul1.im, cmul2.re,cmul2.im);

/* multiply the views by their complex coefficients */
cvcsml(view1, 2, &cmul1, cbtemp1, 2, fr);
cvcsml(view2, 2, &cmul2, cbtemp2, 2, fr);

/* add the two views */
vadd(cbtemp1, 1, cbtemp2, 1, cbtemp1, 1, 2 * fr);

vgrid(trecParams, trecMemory, trecTables, vkx0, vky0, vvx, vvy, cbtemp1);

sx0 = -sin(va1) * cbdist;
sy0 = -cos(va1) * cbdist;

cbcc(trecParams, trecTables, trecMemory, sx0, rcos, &cindex);
vkx0 = (INT32 *) trecMemory->cbcoords + cindex * cwidth;
vvx = (REAL32 **) vkx0 + cwidth / 2;
cbcc(trecParams, trecTables, trecMemory, sy0, rsin, &cindex);
vky0 = (INT32 *) trecMemory->cbcoords + cindex * cwidth;
vvy = (REAL32 **) vky0 + cwidth / 2;

/* for the second backprojection the coefficients are conjugated */
cmul1.im = -cmul1.im;
cmul2.im = -cmul2.im;

/* multiply by the coefficients */
cvcsml(view1, 2, &cmul1, cbtemp1, 2, fr);
cvcsml(view2, 2, &cmul2, cbtemp2, 2, fr);

/* add the two views */ vadd(cbtemp1, 1, cbtemp2, 1, cbtemp1, 1, 2 * fr);

vgrid(trecParams, trecMemory, trecTables, vkx0, vky0, vvx, vvy, cbtemp1);

return(0);
}

/* Cone beam coordinate calculation. We backproject 4 views at once
because due to symmetry we can get away with half the coordinate
calculations. For non-cone beam we actually figured out the
symmetries for the 4 backprojections. For cone beam there are 8
backprojections and 16 coordinate calcs. This is just too many
different cases to consider. Therefore we try a different approach.
The coordinate calculation depends on s0 and inc. We store the pairs
(s0,inc) and coordiante arrays that we have already calculated. Then
```

```
for each new coordinate calc we check if (s0,inc) match a previously
calculated pair. If so we use the previous pair's array, if not we
calculate a new one.
*/
#define ACCUR (5.0e-9)

INT cbcc(trecParams, trecTables, trecMemory, s0, inc, cindex)
TREC_PARAMS *trecParams;
TREC_TABLES *trecTables;
TREC_MEMORY *trecMemory;
REAL s0, inc;
INT *cindex;
{
 INT i, cwidth = trecParams->cwidth;
 INT32 *vk;
 REAL32 **vv;

/* look to see if we have already calculated these coords */
 for(i=0;i<ncalc;i++)
   {if((fabs(s0 - stab[i]) < ACCUR) && (fabs(inc - itab[i]) < ACCUR))
     {*cindex = i;
      return(0);
     }
   }

/* need to calculate a new set */
 vk = (INT32 *) trecMemory->cbcoords + ncalc * cwidth;
 vv = (REAL32 **) vk + cwidth/2;
 calccoord(trecParams, trecTables->grtable, s0, inc, vk, vv, trecMemory->vs);
 stab[ncalc] = s0;
 itab[ncalc] = inc;
 *cindex = ncalc++;

return(0);
}

/* calccoord creates a vector of real coordinates: vs[i] = s0 + inc * i.
   For each of those coordinates it chooses an integer position vk0,
   for the start of the convolution function (width nt) and an error
   term d that represents the distance from the center of the function to v[i].
   This error term is then converted into an address vv[i], that points to
   the correct entry in grtable for that error.
*/

INT
 calccoord(trecParams, grtable, s0, inc, vk0, vv, vs)
TREC_PARAMS *trecParams;
REAL32 *grtable;
REAL s0, inc; /* offset and increment for the coordinates */
INT32 *vk0; /* output array of integer coordinates */
REAL32 **vv; /* output array of addresses */
REAL32 *vs; /* a temp storage array */
{
 INT32 nt2, nt4, nfm1, ntodd, nr, fr, ibignum, beg, nr2, r;
 INT32 casize = 2048;
 REAL32 nquantr, rs0, rinc, rnt5, rbignum, zero = 0.0, one = 1.0;
 REAL32 *ca = salcache;

rinc = inc; /* ditto */
 nquantr = trecParams->nq; /* ditto */ nt2 = trecParams->nt / 2;
 nt4 = trecParams->nt * 4;
 nfm1 = trecParams->fwidth - 1;
 ntodd = ((nt2 * 2) != trecParams->nt);
 nr = trecParams->cwidth / 2;
 fr = trecParams->fr;

rs0 = s0; /* need a REAL32 */

/* for nt odd we sub .5 to get error between 0 and 1
    instead of -.5 to .5 */
 if(ntodd) rs0 -= .5;
 rnt5 = trecParams->nt * .5;
 if(ntodd) rnt5 -= .5;
 rbignum = -3 * nr - rnt5;
 ibignum = 3 * nr;
```

```
/* create a vector of coordinates.  our object is to translate this into
   a set of integers plus real fractions.  The fractions are converted
   into addresses into the grtable */
#if 0  /* this way isn't faster than the optimized makecoord */

/* just in case fr might get larger than casize we stripmine
   the data */ for(beg = 0; beg < fr;beg += casize)
   {nr2 = fr - beg;
    if(nr2 > casize) nr2 = casize;

/* the stuff with bignum calcs ceil(vs[i] - nt5) */
    rs0 = s0 + beg * rinc;
    if(ntodd) rs0 -= .5;
    vrampx(&rs0, &rinc, ca, 1, nr2,SAL_C);
    vmovx(ca, 1, vs, 1, nr2, SAL_CN);
    vsaddx(ca, 1, &rbignum, ca, 1, nr2,SAL_CC);
    vfix32x(ca, 1, ca, 1, nr2, SAL_CC);
    vsaddix(ca, 1, &ibignum, ca, 1, nr2, SAL_CC);
    vmovx(ca, 1, vk0 + beg, 1, nr2, SAL_CN);
    /* now we must calculate the error d = (vk0[i] + nt/2) - vs[i]*/
    vsaddix(ca, 1, &nt2, ca, 1, nr2, SAL_CC);
    vflt32x(ca, 1, ca, 1, nr2, SAL_CC);
    vsubx(vs, 1, ca, 1, ca, 1, nr2, SAL_NCC);
    /* need this for nq = 4096 && c100 */
    vclipx(ca, 1, &zero, &one, ca, 1, nr2, SAL_CC);

/* have calculated the fractions and made sure they are between 0 and 1 */
    /* now convert into an address */
    vsmulx(ca, 1, &nquantr, ca, 1, nr2, SAL_CC);
    vfix32x(ca, 1, ca, 1, nr2, SAL_CC);
    vsmulix(ca, 1, &nt4, ca, 1, nr2, SAL_CC);
    vsaddix(ca, 1, &grtable, vv + beg, 1, nr2, SAL_CN);
   }

/* finally we make sure the integers are in the range 0 .. nfm1 */
 for(r = 0; r < fr; r++)
    vk0[r] &= nfm1;
endif makecoord(&rs0, &rinc, vk0, vv, trecParams->nt, &rbignum, &nquantr,
             ibignum, nfm1, grtable, fr);

return(0);
}

/* routine to calc the coordinates.  This was done by ESAL routines,
   but we now have an assemble lang routine to do it.  This explains
   why it has been split off from calccoords
*/
#ifdef UNIX
int makecoord(ars0, arinc, vk0, vv, nt, arbignum, anquantr,
              ibignum, nfm1, grtable, fr)
REAL32 *ars0, *arinc;
INT32 *vk0;
REAL32 **vv;
REAL32 *arbignum, *anquantr;
INT nt, ibignum, nfm1, fr;
REAL32 *grtable;

{INT i, nt4, nt2, itmp;
 REAL32 rtmp1, rtmp2, rbignum, nquantr, rs0, rinc;

nt2 = nt / 2;
rbignum = *arbignum;
nquantr = *anquantr;
rs0 = *ars0;
rinc = *arinc;
rtmp1 = rs0;

for(i=0;i<fr;i++)
  {rtmp2 = rtmp1 + rbignum;
   itmp = rtmp2;
   itmp += ibignum;
   *vk0++ = itmp & nfm1;
```

```
      itmp += nt2;
      rtmp2 = itmp - rtmp1;
      if(rtmp2 > 1.0) rtmp2 = 1.0;
      if(rtmp2 < 0) rtmp2 = 0.0;
      rtmp2 *= nquantr;
      itmp = rtmp2;
      itmp *= nt;
      *vv++ = itmp + grtable;
      rtmp1 += rinc;
      }
}
endif /* vgrid:perform gridding of input vector into the Fourier image */
/* Input is: vectors of length nr: vkx0,vxy0, vvx,vvy,q also gw,
 * a 2D inverse FFT.
 * Output is gw.
 * vkx0,vky0 hold the x and y matrix positions for each point
 * vvx,vvy hold pointers to the x and y gridding function array.
 * q holds the complex point to be gridded.
 *
 * From paper: Backprojection by Upsampled Fourier Series Expansion
 * and Interpolated FFT
 * By: Makoto Tabei and Mitsuhiro Ueda
 * For each point in q we are given the coords (kx0,ky0) of the beginning
 * point in the matrix for the nt x nt rectangle. We also have the
 * horizontal (vx) and vertical (vy) arrays of the separable gridding
 * function.  The array gw is actually of width mx/2 complexes and
 * length my + 2 rows.  The last two rows hold the column at freq mx/2.
 * For each r from 0 to nr-1 we multiply the complex number q[r]
 * by a ntxnt matrix of coefficients vvx[r][j] * vvy[r][k],
 * where j,k go from 0 to nt-1 and add the ntxnt values into gw
 * starting at vkx0[r],vky0[r].
 * I have never tested this with mx != my.
 *
 */
EXPORT INT
vgrid(trecParams, trecMemory, trecTables, vkx0, vky0, vvx, vvy, q)
TREC_PARAMS *trecParams;
TREC_MEMORY *trecMemory;
TREC_TABLES *trecTables;
INT *vkx0, *vky0;
REAL32  **vvx, **vvy;
COMPLEX32 *q;
{INT jx, jy, kx, ky, ky_f, kx0, ky0, r;
 INT mx, my, nt, nr, w;
 REAL32 v_re, v_im, vy_re, q_re, q_im, *vx, *vy;
 INT mxd2;
 COMPLEX32 *gw, *gw1, *qt;

nr = trecParams->fr;
nt = trecParams->nt;
mx = trecParams->fwidth;
my = mx;
gw = (COMPLEX32 *)trecMemory->fimage;

/* a scheme for increasing speed: use smaller nt for higher frequencies */
/* only working for nt = 5 */
if((trecParams->gridr > 1) && (nt == 5))
 {qt = (COMPLEX32 *)trecMemory->gridtmp;
  r = trecParams->gridr;
  w = trecParams->gridw;
  if(w == 200) return(0);/* secret test code */

/* grid the low frequencies */
  vgrid5(gw, mx, my, nt, r - w, vkx0, vky0, vvx, vvy, q);

/* grid the high frequencies */
  vgrid3x(gw, mx, my, nt, nr - r - w, vkx0 + r + w, vky0 + r + w,
          vvx + r + w, vvy + r + w, q + r + w);

if(w == 0) return(0);

/* feather the intermediate frequencies */
  vmul(q + r - w, 1, trecTables->feather, 1, qt, 1, 4 * w);
```

```
    /* grid the intermediate frequencies */
    vgrid5(gw, mx, my, nt, 2 * w, vkx0 + r - w, vky0 + r - w,
           vvx + r - w, vvy + r - w, qt);

/* feather the low end of the high */
    vsub(qt, 1, q + r - w, 1, qt, 1, 4 * w);

/* do the high freq gridding */
    vgrid3x(gw, mx, my, nt, 2 * w, vkx0 + r - w, vky0 + r - w,
            vvx + r - w, vvy + r - w, qt);

return(0);
  }

/* for the cases nt = 4, 5, 7 we use specifically tailored routines
   to maximize speed
*/ if(nt == 5)
  {vgrid5(gw, mx, my, nt, nr, vkx0, vky0, vvx, vvy, q);
   return(0);
  }
else if(nt == 4)
  {vgrid4(gw, mx, my, nt, nr, vkx0, vky0, vvx, vvy, q);
   return(0);
  }
else if(nt == 7)
  {vgrid7(gw, mx, my, nt, nr, vkx0, vky0, vvx, vvy, q);
   return(0);
  }

/* compute some constants. */
mxd2 = mx / 2;

for(r=0; r<nr; r++)
  {
    kx0 = *vkx0++;
    ky0 = *vky0++;
    vx = *vvx++;
    vy = *vvy++;

/* Map 2-D convolution of q onto gw on gw */
    q_re = q[r].re;
    q_im = q[r].im;
      if((kx0 + nt) <= mxd2)
        {
         ky = ky0;
         for(jy = 0; jy < nt; jy++)
           {
             v_re = q_re * vy[jy];
             v_im = q_im * vy[jy];
             kx = kx0;
             gw1 = gw + mxd2 * ky;
             for(jx = 0;jx < nt; jx++)
               {
                 gw1[kx].re += v_re * vx[jx];
                 gw1[kx].im += v_im * vx[jx];
                 kx++;
               }
             if((++ky) == my) ky = 0;
           }
         continue;
        }
      if((kx0 > mxd2) && (kx0 <= mx - nt))
        {
         if(ky0 == 0) ky_f = 0;
         else ky_f = my - ky0;
         for(jy = 0; jy < nt; jy++)
           {
             v_re = q_re * vy[jy];
             v_im = q_im * vy[jy];
             kx = mx - kx0;
             gw1 = gw + mxd2 * ky_f;
             for(jx = 0;jx < nt; jx++)
               {
```

```
          gw1[kx].re += v_re * vx[jx];
          gw1[kx].im -= v_im * vx[jx];
          kx--;
          }
        if((--ky_f) < 0) ky_f = my - 1;
        }
      continue;

}
/* separating out the above special cases speeds up the algorithm.
   the following code can handle all cases, but is slower so we
   use it for what is left over from the above.
*/
    kx = kx0;
    for(jx = 0; jx < nt; jx++)
    {
      v_re = q_re * vx[jx];
      v_im = q_im * vx[jx];
      if(kx <= mxd2)     /* check folding */
        {
        ky = ky0;
        if(kx != mxd2)
          {
          gw1 = gw + kx;
          for(jy = 0; jy < nt; jy++)
            {
            gw1[mxd2 * ky].re += v_re * vy[jy];
            gw1[mxd2 * ky].im += v_im * vy[jy];
            if((++ky) == my) ky = 0;
            }
          }
        /* note the special encoding, the kx = mx/2 column is stored in the
           last two rows */
        else
          {
          gw1 = gw + mxd2 * my;
          for(jy = 0; jy < nt; jy++)
            {
            gw1[ky].re += v_re * vy[jy];
            gw1[ky].im += v_im * vy[jy];
            if((++ky) == my) ky = 0;
            }
          }
        }
      else
        {
        if( ky0 == 0) ky_f = 0;
        else ky_f = my - ky0;
        gw1 = gw + (mx - kx);
        for(jy = 0; jy < nt; jy++)
          {
          gw1[mxd2 * ky_f].re += v_re * vy[jy];
          gw1[mxd2 * ky_f].im -= v_im * vy[jy];
          if((--ky_f) < 0) ky_f = my - 1;
          }
        }
      if((++kx) == mx) kx = 0;
    }
  }
 return(0);
}   /* vgrid */ ifdef UNIX            /* for 860 use assembly lang version */
/* vgrid:perform gridding of input vector into the Fourier image */
/* Input is: vectors of length nr: vkx0,vxy0,vvx,vvy,q also gw,
   a 2D inverse FFT of width mx (i.e. mx/2 complexes) and height my
   For our case mx always equals my.
   Output is gw.
   gw has two extra rows holding the high freq terms of the other rows
   vkx0,vky0 hold the x and y matrix positions for each point
   vvx,vvy hold pointers to the x and y gridding function array.
   q holds the complex point to be gridded.
   For each r from 0 to nr-1 we multiply the complex number q[r]
   by a ntxnt matrix of coefficients vvx[r][j] * vvy[r][k],
   where j,k go from 0 to nt-1 and add the ntxnt values into gw
   starting at vkx0[r],vky0[r].
```

```
*/
/* special version for nt = 5 */

INT
vgrid5(gw, mx, my, nt, nr, vkx0, vky0, vvx, vvy, q)
INT mx, my, nt, nr, *vkx0, *vky0;
REAL32    **vvx, **vvy;
COMPLEX32 *gw, *q;
{INT jx, jy, kx, ky, ky_f, kx0, ky0, r;
 REAL32 v_re, v_im, vy_re, q_re, q_im, *vx, *vy;
 REAL32 v0, v1, v2, v3, v4;
 INT mxd2;
 COMPLEX32 *gw1;

/* compute some constants. */
 mxd2 = mx / 2;

/* main loop */
 for(r=0; r<nr; r++)
   {
   /* get the position in the matrix */
   kx0 = *vkx0++;
   ky0 = *vky0++;
   /* get the address of the gridding fcns */
   vx = *vvx++;
   vy = *vvy++;

/* get the input complex points */
   q_re = q[r].re;
   q_im = q[r].im;

/* get the x gridding coefficients */
   v0 = vx[0];
   v1 = vx[1];
   v2 = vx[2];
   v3 = vx[3];
   v4 = vx[4];

/* divide the work into 3 special cases depending on kx0 */
   /* first is case 1: kx0 + 4 < mx/2 */
   if((kx0 + 5) <= mxd2)
     {
     ky = ky0;
     for(jy = 0; jy < 5; jy++)
       {
       v_re = q_re * vy[jy];
       v_im = q_im * vy[jy];
       kx = kx0;
       gw1 = gw + mxd2 * ky;
       gw1[kx].re += v_re * v0;
       gw1[kx].im += v_im * v0;
       kx++;
       gw1[kx].re += v_re * v1;
       gw1[kx].im += v_im * v1;
       kx++;
       gw1[kx].re += v_re * v2;
       gw1[kx].im += v_im * v2;
       kx++;
       gw1[kx].re += v_re * v3;
       gw1[kx].im += v_im * v3;
       kx++;
       gw1[kx].re += v_re * v4;
       gw1[kx].im += v_im * v4;

if((++ky) == my) ky = 0;
       }
     continue;
     }

/* second is case 2: kx0 > mx/2 and kx0 <= mx - 5 */
   if((kx0 > mxd2) && (kx0 <= mx - 5))
     {
     if(ky0 == 0) ky_f = 0;
     else ky_f = my - ky0;
     for(jy = 0; jy < 5; jy++)
```

```
    {
      v_re = q_re * vy[jy];
      v_im = q_im * vy[jy];
      kx = mx - kx0;
      gw1 = gw + mxd2 * ky_f;
      gw1[kx].re += v_re * v0;
      gw1[kx].im -= v_im * v0;
      kx--;
      gw1[kx].re += v_re * v1;
      gw1[kx].im -= v_im * v1;
      kx--;
      gw1[kx].re += v_re * v2;
      gw1[kx].im -= v_im * v2;
      kx--;
      gw1[kx].re += v_re * v3;
      gw1[kx].im -= v_im * v3;
      kx--;
      gw1[kx].re += v_re * v4;
      gw1[kx].im -= v_im * v4;

if((--ky_f) < 0) ky_f = my - 1;
    }
   continue;
    }

/* separating out the above special cases speeds up the algorithm.
   the following code can handle all cases, but is slower so we
   use it for what is left over from the above.
*/
   kx = kx0;
   for(jx = 0; jx < 5; jx++)
    {
     v_re = q_re * vx[jx];
     v_im = q_im * vx[jx];
     if(kx <= mxd2)      /* check folding */
      {
       ky = ky0;
       if(kx != mxd2)    /* this is the kx < mx/2 case */
        {
         gw1 = gw + kx;
         for(jy = 0; jy < 5; jy++)
          {
           gw1[mxd2 * ky].re += v_re * vy[jy];
           gw1[mxd2 * ky].im += v_im * vy[jy];
           if((++ky) == my) ky = 0;
          }
        }
       /* note the special encoding, the kx = mx/2 column is stored in the
          last two rows */
       else     /* this is the kx = mx/2 case */
        {
         gw1 = gw + mxd2 * my;
         for(jy = 0; jy < 5; jy++)
          {
           gw1[ky].re += v_re * vy[jy];
           gw1[ky].im += v_im * vy[jy];
           if((++ky) == my) ky = 0;
          }
        }
      }
     else /* this is the kx > mx/2 case */
      {
       if( ky0 == 0) ky_f = 0;
       else ky_f = my - ky0;
       gw1 = gw + (mx - kx);
       for(jy = 0; jy < 5; jy++)
        {
         gw1[mxd2 * ky_f].re += v_re * vy[jy];
         gw1[mxd2 * ky_f].im -= v_im * vy[jy];
         if((--ky_f) < 0) ky_f = my - 1;
        }
      }
     if((++kx) == mx) kx = 0;
    }
  }
 return(0);
}    /* vgrid5 */
#endif
```

```c
/* spread out the convolution functions into the Fourier image */
/* special version for nt = 4 */
EXPORT INT
vgrid4(gw, mx, my, nt, nr, vkx0, vky0, vvx, vvy, q)
INT mx, my, nt, nr, *vkx0, *vky0;
REAL32 **vvx, **vvy;
COMPLEX32 *gw, *q;
{INT jx, jy, kx, ky, ky_f, kx0, ky0, r;
 REAL32 v_re, v_im, vy_re, q_re, q_im, *vx, *vy;
 REAL32 v0, v1, v2, v3;
 INT mxd2;
COMPLEX32 *gw1;

/* compute some constants. */
mxd2 = mx / 2;

for(r=0; r<nr; r++)
  {
    kx0 = *vkx0++;
    ky0 = *vky0++;
    vx = *vvx++;
    vy = *vvy++;

/* Map convolution function on gw */
    q_re = q[r].re;
    q_im = q[r].im;

v0 = vx[0];
    v1 = vx[1];
    v2 = vx[2];
    v3 = vx[3];

if((kx0 + 4) <= mxd2)
      {
        ky = ky0;
        for(jy = 0; jy < 4; jy++)
          {
            v_re = q_re * vy[jy];
            v_im = q_im * vy[jy];
            kx = kx0;
            gw1 = gw + mxd2 * ky;
            gw1[kx].re += v_re * v0;
            gw1[kx].im += v_im * v0;
            kx++;
            gw1[kx].re += v_re * v1;
            gw1[kx].im += v_im * v1;
            kx++;
            gw1[kx].re += v_re * v2;
            gw1[kx].im += v_im * v2;
            kx++;
            gw1[kx].re += v_re * v3;
            gw1[kx].im += v_im * v3;

if((++ky) == my) ky = 0;
          }
        continue;
      }
    if((kx0 > mxd2) && (kx0 <= mx - 4))
      {
        if(ky0 == 0) ky_f = 0;
        else ky_f = my - ky0;
        for(jy = 0; jy < 4; jy++)
          {
            v_re = q_re * vy[jy];
            v_im = q_im * vy[jy];
            kx = mx - kx0;
            gw1 = gw + mxd2 * ky_f;
            gw1[kx].re += v_re * v0;
            gw1[kx].im -= v_im * v0;
            kx--;
            gw1[kx].re += v_re * v1;
            gw1[kx].im -= v_im * v1;
            kx--;
            gw1[kx].re += v_re * v2;
            gw1[kx].im -= v_im * v2;
            kx--;
```

```
      gw1[kx].re += v_re * v3;
      gw1[kx].im -= v_im * v3;

if((--ky_f) < 0) ky_f = my - 1;
        }
      continue;

} kx = kx0;
    for(jx = 0; jx < 4; jx++)
     {
      v_re = q_re * vx[jx];
      v_im = q_im * vx[jx];
      if(kx <= mxd2)      /* check folding */
        {
         ky = ky0;
         if(kx != mxd2)
           {
            gw1 = gw + kx;
            for(jy = 0; jy < 4; jy++)
              {
               gw1[mxd2 * ky].re += v_re * vy[jy];
               gw1[mxd2 * ky].im += v_im * vy[jy];
               if((++ky) == my) ky = 0;
              }
           }
         /* note the special encoding, the kx = mx/2 column is stored in the
            last two rows */
         else
           {
            gw1 = gw + mxd2 * my;
            for(jy = 0; jy < 4; jy++)
              {
               gw1[ky].re += v_re * vy[jy];
               gw1[ky].im += v_im * vy[jy];
               if((++ky) == my) ky = 0;
              }
           }
        }
      else
        {
         if( ky0 == 0) ky_f = 0;
         else ky_f = my - ky0;
         gw1 = gw + (mx - kx);
         for(jy = 0; jy < 4; jy++)
           {
            gw1[mxd2 * ky_f].re += v_re * vy[jy];
            gw1[mxd2 * ky_f].im -= v_im * vy[jy];
            if((--ky_f) < 0) ky_f = my - 1;
           }
        }
      if((++kx) == mx) kx = 0;
     }
   }
 return(0);
}   /* vgrid4 */

/* spread out the convolution functions into the Fourier image */
/* special version for nt = 7 */
EXPORT INT
vgrid7(gw, mx, my, nt, nr, vkx0, vky0, vvx, vvy, q)
INT mx, my, nt, nr, *vkx0, *vky0;
REAL32  **vvx, **vvy;
COMPLEX32 *gw, *q;
{INT jx, jy, kx, ky, ky_f, kx0, ky0, r;
 REAL32 v_re, v_im, vy_re, q_re, q_im, *vx, *vy;
 REAL32 v0, v1, v2, v3, v4, v5, v6;
 INT mxd2;
 COMPLEX32 *gw1;

/* compute some constants. */
 mxd2 = mx / 2;
```

```c
for(r=0; r<nr; r++)
{
  kx0 = *vkx0++;
  ky0 = *vky0++;
  vx = *vvx++;
  vy = *vvy++;

/* Map 2-D convolution function on gw */
  q_re = q[r].re;
  q_im = q[r].im;

v0 = vx[0];
  v1 = vx[1];
  v2 = vx[2];
  v3 = vx[3];
  v4 = vx[4];
  v5 = vx[5];
  v6 = vx[6];

if((kx0 + 7) <= mxd2)
  {
    ky = ky0;
    for(jy = 0; jy < 7; jy++)
    {
      v_re = q_re * vy[jy];
      v_im = q_im * vy[jy];
      kx = kx0;
      gw1 = gw + mxd2 * ky;
      gw1[kx].re += v_re * v0;
      gw1[kx].im += v_im * v0;
      kx++;
      gw1[kx].re += v_re * v1;
      gw1[kx].im += v_im * v1;
      kx++;
      gw1[kx].re += v_re * v2;
      gw1[kx].im += v_im * v2;
      kx++;
      gw1[kx].re += v_re * v3;
      gw1[kx].im += v_im * v3;
      kx++;
      gw1[kx].re += v_re * v4;
      gw1[kx].im += v_im * v4;
      kx++;
      gw1[kx].re += v_re * v5;
      gw1[kx].im += v_im * v5;
      kx++;
      gw1[kx].re += v_re * v6;
      gw1[kx].im += v_im * v6;

if((++ky) == my) ky = 0;
    }
    continue;
  }
  if((kx0 > mxd2) && (kx0 <= mx - 7))
  {
    if(ky0 == 0) ky_f = 0;
    else ky_f = my - ky0;
    for(jy = 0; jy < 7; jy++)
    {
      v_re = q_re * vy[jy];
      v_im = q_im * vy[jy];
      kx = mx - kx0;
      gw1 = gw + mxd2 * ky_f;
      gw1[kx].re += v_re * v0;
      gw1[kx].im -= v_im * v0;
      kx--;
      gw1[kx].re += v_re * v1;
      gw1[kx].im -= v_im * v1;
      kx--;
      gw1[kx].re += v_re * v2;
      gw1[kx].im -= v_im * v2;
      kx--;
      gw1[kx].re += v_re * v3;
      gw1[kx].im -= v_im * v3;
      kx--;
      gw1[kx].re += v_re * v4;
      gw1[kx].im -= v_im * v4;
```

```
        kx--;
        gw1[kx].re += v_re * v5;
        gw1[kx].im -= v_im * v5;
        kx--;
        gw1[kx].re += v_re * v6;
        gw1[kx].im -= v_im * v6;

if((--ky_f) < 0) ky_f = my - 1;
      }
    continue;
  } kx = kx0;
  for(jx = 0; jx < 7; jx++)
  {
    v_re = q_re * vx[jx];
    v_im = q_im * vx[jx];
    if(kx <= mxd2)        /* check folding */
      {
        ky = ky0;
        if(kx != mxd2)
          {
            gw1 = gw + kx;
            for(jy = 0; jy < 7; jy++)
              {
                gw1[mxd2 * ky].re += v_re * vy[jy];
                gw1[mxd2 * ky].im += v_im * vy[jy];
                if((++ky) == my) ky = 0;
              }
          }
        /* note the special encoding, the kx = mx/2 column is stored in the
           last two rows */
        else
          {
            gw1 = gw + mxd2 * my;
            for(jy = 0; jy < 7; jy++)
              {
                gw1[ky].re += v_re * vy[jy];
                gw1[ky].im += v_im * vy[jy];
                if((++ky) == my) ky = 0;
              }
          }
      }
    else
      {
        if( ky0 == 0) ky_f = 0;
        else ky_f = my - ky0;
        gw1 = gw + (mx - kx);
        for(jy = 0; jy < 7; jy++)
          {
            gw1[mxd2 * ky_f].re += v_re * vy[jy];
            gw1[mxd2 * ky_f].im -= v_im * vy[jy];
            if((--ky_f) < 0) ky_f = my - 1;
          }
      }
    if((++kx) == mx) kx = 0;
  }
}
return(0);
  }   /* vgrid7 */ ifdef UNIX
INT
vgrid3x(gw, mx, my, nt, nr, vkx0, vky0, vvx, vvy, q)
INT mx, my, nt, nr, *vkx0, *vky0;
REAL32  **vvx, **vvy;
COMPLEX32 *gw, *q;
{INT jx, jy, kx, ky, ky_f, kx0, ky0, r;
 REAL32 v_re, v_im, vy_re, q_re, q_im, *vx, *vy;
 REAL32 v0, v1, v2, v3, v4;
 INT mxd2;
 COMPLEX32 *gw1;

/* compute some constants. */
 mxd2 = mx / 2;
```

```
for(r=0; r<nr; r++)
 {
  kx0 = *vkx0++;
  ky0 = *vky0++;
  vx = *vvx++;
  vy = *vvy++;

/* Map 2-D convolution function on gw */
  q_re = q[r].re;
  q_im = q[r].im;

v1 = vx[1];
  v2 = vx[2];
  v3 = vx[3];

if((kx0 + 5) <= mxd2)   /* i.e. kx0 + 4 < mx/2 */
    {
     ky = ky0;
     if((++ky) == my) ky = 0;

for(jy = 1; jy < 4; jy++)
       {
        v_re = q_re * vy[jy];
        v_im = q_im * vy[jy];
        kx = kx0 + 1;
        gw1 = gw + mxd2 * ky;
        gw1[kx].re += v_re * v1;
        gw1[kx].im += v_im * v1;
        kx++;
        gw1[kx].re += v_re * v2;
        gw1[kx].im += v_im * v2;
        kx++;
        gw1[kx].re += v_re * v3;
        gw1[kx].im += v_im * v3;
        if((++ky) == my) ky = 0;
       }
     continue;
    }
  if((kx0 > mxd2) && (kx0 <= mx - 5))
    {
     if(ky0 == 0) ky_f = 0;
     else ky_f = my - ky0;
     if((--ky_f) < 0) ky_f = my - 1;

for(jy = 1; jy < 4; jy++)
       {
        v_re = q_re * vy[jy];
        v_im = q_im * vy[jy];
        gw1 = gw + mxd2 * ky_f;

kx = mx - kx0 - 1;
        gw1[kx].re += v_re * v1;
        gw1[kx].im -= v_im * v1;
        kx--;
        gw1[kx].re += v_re * v2;
        gw1[kx].im -= v_im * v2;
        kx--;
        gw1[kx].re += v_re * v3;
        gw1[kx].im -= v_im * v3;

if((--ky_f) < 0) ky_f = my - 1;
       }
     continue;
    }

}

/* separating out the above special cases speeds up the algorithm.
   the following code can handle all cases, but is slower so we
   use it for what is left over from the above.
*/
  if(1) continue;
  kx = kx0;
  if((++kx) == mx) kx = 0;
  for(jx = 1; jx < 4; jx++)
    {
     v_re = q_re * vx[jx];
```

```
        v_im = q_im * vx[jx];
        if(kx <= mxd2)      /* check folding */
          {
          ky = ky0;
          if((++ky) == my) ky = 0;
          if(kx != mxd2)   /* this is the kx < mx/2 case */
            {
            gw1 = gw + kx;
            for(jy = 1; jy < 4; jy++)
              {
              gw1[mxd2 * ky].re += v_re * vy[jy];
              gw1[mxd2 * ky].im += v_im * vy[jy];
              if((++ky) == my) ky = 0;
              }
            }
          /* note the special encoding, the kx = mx/2 column is stored in the
             last two rows */
          else     /* this is the kx = mx/2 case */
            {
            gw1 = gw + mxd2 * my;
            for(jy = 1; jy < 4; jy++)
              {
              gw1[ky].re += v_re * vy[jy];
              gw1[ky].im += v_im * vy[jy];
              if((++ky) == my) ky = 0;
              }
            }
          }
        else /* this is the kx > mx/2 case */
          {
          if( ky0 == 0) ky_f = 0;
          else ky_f = my - ky0;
          if((--ky_f) < 0) ky_f = my - 1;
          gw1 = gw + (mx - kx);
          for(jy = 1; jy < 4; jy++)
            {
            gw1[mxd2 * ky_f].re += v_re * vy[jy];
            gw1[mxd2 * ky_f].im -= v_im * vy[jy];
            if((--ky_f) < 0) ky_f = my - 1;
            }
          }
        if((++kx) == mx) kx = 0;
        }
    }
   return(0);

}    /* vgrid3x */
#endif

/******************** End Of trecTbp.c ********************/
/*
 * File Name: trecTable.c
 *
 * Author    : Jon Harman
 *
 * Brief Description: Creates tables for trec.
 *
 * Copyright 1993 Imatron, Inc.
 *
 * Command Line Synopsis:
 *
 * Long Description:
 *
 * Deficiencies / bugs:
 *
 * Return (status) codes, error messages:
 *
 * Abbreviations used:
 *
 * Revision History (latest updates first!): 3/10/93(jonh) New.
 */
/* LINTLIBRARY *//* suppresses some unneeded lint messages */

/* 1.) "Imported" data types and defines: */
/* 1.a.) Standard C include files   */
#include        <stdio.h>
#include        <math.h>
```

```
/* 1.b.) Imatron ../include files */
include        "../include/imatron.h"  /* first Imatron include */

/* 1.c.) Project include files                                */
#include        "trec.h"

/* 1.d.) Other include files                                  */

/* 2.) Externals defined in this file (declarations only): */
FORWARD INT trecRBTable();

/* 3.) "Imported" externals: */
/* 3.a.) Imported from standard C Library                     */

/* 3.b.) Imported from ../xxxxx                       */

/* 3.c.) Imported from other files in this dtrectory */
/* 3.d.) Imported from elsewhere */
PRIVATE INT debug = 0;

/* 4.) "Private" data types, defines, data and code */
/* for debugging purposes */
PRIVATE INT isd = -1, isgd = -1;
PRIVATE REAL tsinc(), gridfcn();

/* 5.) Exported Functions and Data: */

/*
 * rebinning table creation routine. the tables created are nnsigma,
 * nnbeta, phi, psi. memory is allocated for them, total memory used is
 * added to memtot
 */

EXPORT INT
trecRBTable(trecParams, trecTables)
   TREC_PARAMS *trecParams;      /* parameters that define the rebinning */
   TREC_TABLES *trecTables;      /* pointers to memory for tables */
{
   REAL soffset = -.5, r = 1000.0;
   REAL beta0, dbeta, theta0, dtheta, sigma0, dsigma, s0, ds;
   REAL sigma, beta, bmin, bmax, accum, accumk;
   REAL ang, rnk, rnl;

INT32 nbeta, ntheta, nsigma, ns, nphi;
   INT32 ibeta, itheta, isigma, is, itheta0;

INT32 i, k, l, ll, iang, betaflag, maxb, minb, minviews;
   INT32 nnl, nnk;

UINT16 *nnsigma, *nnbeta;
   REAL32 *phi, *psi;

CHAR str[100];

/*
    * Allocate the nearest neighbor tables.  These give the closest fan
    * geometry point to a given parallel geometry point.
    */ nnsigma = (UINT16 *) malloc(trecParams->rwidth * sizeof(*nnsigma));
   nnbeta = (UINT16 *) malloc(trecParams->nsamps * sizeof(*nnbeta));
   if (!nnbeta || !nnsigma)
   {
      printf("trecTable: Cannot get memory for nn tables\n");
      return (-1);
   }
   /*
    * Allocate the phi and psi tables.  These are the main interpolation
    * tables. psi[is,isigma] phi[isigma,ibeta].
    */ phi = (REAL32 *)
      malloc(trecParams->nsamps * trecParams->nl * 2 * sizeof(REAL32));
   psi = (REAL32 *)
```

```
      malloc(trecParams->rwidth * trecParams->nk * 2 * sizeof(REAL32));
   if (!psi || !phi)
   {
      printf("trecTable: Cannot get memory for psi,phi tables\n");
      return (-2);
   }
   /* update memory usage */
   trecTables->memtot += trecParams->rwidth * sizeof(*nnsigma) +
      trecParams->nsamps * sizeof(*nnbeta) +
      (trecParams->nsamps * trecParams->nl * 2 +
      trecParams->rwidth * trecParams->nk * 2) * sizeof(REAL32);
   trecTables->nnsigma = nnsigma;
   trecTables->nnbeta = nnbeta;
   trecTables->phi = phi;
   trecTables->psi = psi;

if (debug)
   {
      isd = 100;
      isgd = 100;
/*    printf("Enter isd[%d] isgd[%d]:", isd, isgd);
      gets(str);
      if (strlen(str) > 0)
         sscanf(str, "%d %d", &isd, &isgd);
*/
   }
   /* first we determine the limits for our variables */

/* beta is the fan geometry view number */
   beta0 = 0.0;
   dbeta = PI / trecParams->pviews;
   nbeta = trecParams->pviews * 2;
   trecParams->minviews =
      (trecParams->fanang + PI) * trecParams->pviews / PI + .5;
   nnl = 2 * trecParams->nl;
   nnk = 2 * trecParams->nk;
   rnl = (REAL) trecParams->nl;
   rnk = (REAL) trecParams->nk;

/* sigma is the fan geometry sample position, equal angle samples. */
   dsigma = trecParams->fanang / (trecParams->nsamps - 1);
   sigma0 = (-trecParams->fanang / 2.0) + trecParams->sampoffset * dsigma;
   nsigma = trecParams->nsamps;

/* theta is the parallel geometry view number */
   ntheta = nbeta / 2;
   dtheta = dbeta;                 /* dtheta must = dbeta to use the phi table */
   theta0 = beta0 + dbeta * trecParams->nl + (nsigma - 1) * dsigma + sigma0;
   itheta0 = theta0 / dtheta + .5;
   itheta0++;                      /* a little extra */
   theta0 = itheta0 * dtheta;      /* we want theta0 to be a power of dtheta */
   theta0 += trecParams->tshift;

/* s is the parallel geometry sample position */
   ds = 2 * r * sin(trecParams->fanang / 2.0) / (trecParams->rwidth - 1);
   s0 = r * sin(-trecParams->fanang / 2.0) + soffset * ds;
   ns = trecParams->rwidth;
   /*
    * Create the nearest neighbor tables.  These give the closest fan
    * geometry point to a given parallel geometry point.
    */ bmin = TWOPI;
   bmax = 0.0;
   for (is = 0; is < ns; is++)
   {
      sigma = asin((is * ds + s0) / r);
      i = (sigma - sigma0) / dsigma - trecParams->nk + 1.0;
      if (i < 0)
         i = 0;
      if (i > nsigma - nnk)
         i = nsigma - nnk;
      if (is == isd)
         printf("is:%d sigma:%g nnsigma:%d\n", is, sigma, i);
      nnsigma[is] = i;
   }
```

```
minb = trecParams->minviews;
maxb = 0;
for (isigma = 0; isigma < nsigma; isigma++)
{
  sigma = isigma * dsigma + sigma0;
  beta = theta0 - sigma;
  if (beta < bmin)
    bmin = beta;
  if (beta > bmax)
    bmax = beta;
  ibeta = (beta - beta0) / dbeta - trecParams->nl + 1.0;
  if (isigma == isgd)
    printf("isg:%d sigma:%g beta:%g nnbeta:%d\n",
           isigma, sigma, beta, ibeta),
  if(ibeta < minb) minb = ibeta;
  if(ibeta > maxb) maxb = ibeta;
  nnbeta[isigma] = ibeta;
} if(maxb - minb + ntheta > trecParams->minviews)
  trecParams->minviews = maxb - minb + ntheta;

if (debug)
  printf("rbtable: Finished with nn tables. min:%d max:%d\n",minb, maxb);
/*
 * Create the phi and psi tables.  These are the main interpolation
 * tables. psi[is,k] phi[l,isigma].
 */ if (debug)
  printf("rbtable: Making psi and phi Tables.\n");

/*
 * make the phi table.  This is used for the initial (beta, sigma) to
 * (theta, sigma) interpolation
 */ for (isigma = 0; isigma < nsigma; isigma++)
{
  accum = 0.0;
  for (l = 0; l < nnl; l++)
  {
    sigma = isigma * dsigma + sigma0;
    beta = (nnbeta[isigma] + l) * dbeta + beta0;
    ang = beta + sigma - theta0;
    if (ang > PI)
      ang = ang - TWOPI;
    if (ang < -PI)
      ang = ang + TWOPI;
    ang = ang / dbeta;
    accumk = tsinc(ang * trecParams->rl, rnl, trecParams->ecl);
    /*
     * if(nnl > 2) accumk = tsinc(ang * trecParams->rl, rnl,
     * trecParams->ecl); else { if(ang > 0) accumk = 1.0 - ang; else
     * accumk = 1.0 + ang; }
     */ phi[l + isigma * nnl] = accumk;
    accum += accumk;
    if (isigma == isgd)
       printf("isg:%d l:%d sigma:%g beta:%g ang:%g phi:%g accum:%g\n",
              isigma, l, sigma, beta, ang, phi[l * nsigma + isigma], accum);
  }
  if (accum > 0.0)
    for (l = 0; l < nnl; l++)
      phi[l + isigma * nnl] /= accum;
}

/* adjust nnbeta to start at 0 */
for (isigma = 0; isigma < nsigma; isigma++) nnbeta[isigma] -= minb;

/*
 * make the psi table.  This is used in the (theta,sigma) to (theta,s)
 * interpolation
 */
for (is = 0; is < ns; is++)
{
```

```
accum = 0.0;
for (k = 0; k < nnk; k++)
{
  sigma = (nnsigma[is] + k) * dsigma + sigma0;
  ang = asin((is * ds + s0) / r) - sigma;
  if (ang > PI)
    ang = ang - TWOPI;
  if (ang < -PI)
    ang = ang + TWOPI;
  ang = ang / dsigma;
  accumk = tsinc(ang * trecParams->rk, rnk, trecParams->eck);
  accum += accumk;
  psi[k * ns + is] = accumk;
  if (is == isd)
    printf("is:%d k:%d sigma:%g ang:%g psi:%g accum:%g\n",
           is, k, sigma, ang, psi[k * ns + is], accum);
  } if (accum > 0.0)
      for (k = 0; k < nnk; k++)
        psi[k * ns + is] /= accum;
  }
  if (debug)
    printf("\n");
  if (debug)
    printf("rbtable: Finished with psi and phi tables.\n");
  return (0);
}

/*
 * truncated, tapered sinc interpolation for rebinning. x is the point at
 * which we evaluate the interp function. n is the order of the
 * interpolation (i.e. uses 2n points). it is used to scale the gaussian
 * taper, larger n less taper. k is also used to scale the taper, larger k
 * more taper.  I have also used k to allow for linear interp or for
 * 4 point interpolation using Wallschlaeger's algorithm.  If k is negative
 * then Wallschlaeger's algorithm is used with w = -k -1.
 */
PRIVATE REAL
tsinc(x, n, k)
  REAL x, k, n;
{
  REAL xn;

if (x < 0.0)
    x = -x;
  if (x == 0.0)
    return 1.0;
  xn = x / n;
  if(k >= 0)  return (sin(x * PI) / (x * PI)) *  exp(-x * xn * k);
  else /* try Wallschlager's interpolation function */
    {if(x > 2.0) return(0.0);
     if(x > 1.0) return((-k - 1.0) * (.5 * x - 1.0));
     return(-k + (1.5 * k + .5) * x);
    }
}

/* make the constant data needed for TBP routines.  This includes:
    FFT weights: used by Mercury in fft routines
    convolution kernel: parallel beam Laks kernel. Others can be input
    interpolation filter: filter for folded transformed view
    table for convolution function
    spatial domain transform of convolution function.  Used to norm image.
    ramp for shifttrans
*/

EXPORT INT
trecTBPTable(trecParams, trecTables)
  TREC_PARAMS *trecParams;     /* parameters that define the rebinning */
  TREC_TABLES *trecTables;     /* pointers to memory for tables */
{
 INT i, j, k, kw, fr, tsize;
 CHAR kerfile[100]; /* string specifying a kernel file */
 FILE *fps;
 REAL32 rtemp1, rtemp2;
 REAL beta2;
```

```
  /* AP fft routines need weights table */
#ifndef CSPI
  kw = MAX(trecParams->cwidth, trecParams->fwidth);

trecTables->weights = (REAL32 *) malloc(kw * sizeof(REAL32) * 2);

if (!trecTables->weights)
  {
    printf("trec: Cannot get memory for weights array.\n");
    return(-1);
  } trecTables->memtot += kw * sizeof(REAL32) * 2;

/* initialize */
  fftwts(trecTables->weights,kw,kw);
#endif

/* next get memory and initialize the convolution kernel */
  trecTables->kernel = (REAL32 *) malloc(trecParams->cwidth * sizeof(REAL32));

if (!trecTables->kernel)
  {
    printf("trec: Cannot get memory for kernel.\n");
    return(-1);
  } trecTables->memtot += trecParams->cwidth * sizeof(REAL32);

if(trecParams->ktype <= -1)
  {
   printf("Enter kernel file name:");
   gets(kerfile);
   fps = fopen(kerfile, "r");
   if (!fps)
    {
     printf("Unable to open kernel file %s.\n", kerfile);
     trecParams->ktype = 0;
    }
   else
    {
      i = fread(trecTables->kernel, sizeof(REAL32), trecParams->cwidth, fps);
      if(i != trecParams->cwidth)
       {
         printf("Kernel file too small! cwidth:%d size:%d\n",
              trecParams->cwidth, i);
         trecParams->ktype = 0;
       }
      fclose(fps);
    }
  } if(trecParams->ktype >= 0)
   makekernel(trecParams->cwidth, trecParams->ktype,
            trecParams->cutoff, trecTables->kernel);

/* next get memory and initialize the interpolation filter */
 trecTables->ifil = (REAL32 *) malloc(trecParams->cwidth * sizeof(REAL32));

if (!trecTables->ifil)
 {
   printf("trec: Cannot get memory for interpolation filter.\n");
   return(-1);
 } trecTables->memtot += trecParams->cwidth * sizeof(REAL32);

for(i=0;i<trecParams->cwidth;i++)trecTables->ifil[i] = 0.0;

fr = trecParams->fr;
if(!trecParams->si) fr = trecParams->cwidth / 2;
make_ifil(fr, trecParams->itype, trecTables->ifil, trecParams->gridr,
          trecParams->gridw);

/* just for debugging */
if(trecParams->itype > 5) trecParams->gridr = -1;
```

```
/* make the table of Kaiser bessel values for the transform domain
   convolution function
*/
tsize = trecParams->nq *  trecParams->nt;
if(trecParams->gridr > 0)
 {tsize += trecParams->gridw * 4;
 }
trecTables->grtable = (REAL32 *) malloc(tsize * sizeof(REAL32));
if (!trecTables->grtable)
  {
  printf("trec: Cannot get memory for kb table.\n");
  return(-1);
  } trecTables->memtot += tsize * sizeof(REAL32);

if(trecParams->gridr > 0)
   trecTables->feather = trecTables->grtable + trecParams->nq * trecParams->nt;
else trecParams->gridw = -1;
make_grtable(trecParams->nt, trecParams->beta,
             trecTables->grtable, trecParams->nq, trecParams->gridw);

/* make the table of values for the spatial domain transform
    of the gridding function.
*/ trecTables->imgwin =
   (REAL32 *) malloc(trecParams->fwidth * sizeof(REAL32));
if (!trecTables->imgwin)
  {
  printf("trec: Cannot get memory for transform kb table.\n");
  return(-1);
  } trecTables->memtot += trecParams->fwidth * sizeof(REAL32);

make_imgwin(trecParams, trecTables->imgwin);

/* make a ramp for shift routine */
trecTables->ramp = (REAL32 *) malloc(trecParams->cwidth * sizeof(REAL32));
if (!trecTables->ramp)
  {
  printf("trec: Cannot get memory for ramp.\n");
  return(-1);
  } trecTables->memtot += trecParams->cwidth * sizeof(REAL32);

rtemp1 = 0.0;
rtemp2 = 1.0;
vramp(&rtemp1, &rtemp2, trecTables->ramp, 2, trecParams->cwidth / 2);
rtemp2 = -1.0;
vramp(&rtemp1, &rtemp2, trecTables->ramp + 1, 2, trecParams->cwidth / 2);

return(0);
}

/* makekernel: make the Imatron kernels.
   ktype determines the kernel type
   0: a straight laks kernel
   1: the Imatron normal kernel:Butterworth 830,.93 1020,.00028",
   2: reserved (currently straight laks)
   3: head 1:w .01633 .3266 .9 times Blackmann 650 1024
   4: head 2:w .02768 .3266 .8305 times Blackmann 650 1024
   5: head smooth:w .01633 .3266 .9 times Hamming 500 1024
   6: sharp:diff of G .5,3 1,-1
   7: very sharp:3 pt -1,3
   8: smooth:Hanning 0 1024
    9: special:3 pt -2,5 then scaled by .5
*/

INT
makekernel(cwidth, ktype, cutoff, kernel)
   INT cwidth, ktype;
   REAL cutoff;
   REAL32 *kernel;
```

```c
{
 INT i, start, stop;
 REAL t,tt;

/* first make a straight laks kernel with cutoff */ for (i = 0; i < cwidth; i++)
  {
    kernel[i] = 0.0;
  }

/* set up the kernel: do it in spatial domain then transform it */

/* parallel geometry */
 tt = 1.0;
 kernel[0] = .25 * tt;
 for (i = 1; i < cwidth/2; i += 2)
  {
    t = -tt / (i * i * PI * PI);
    kernel[i] = t;
    kernel[cwidth - i] = t;
  }

/* transform into freq domain */ rfft(kernel, cwidth, 1);

/* add a filter */
 if (cutoff > 0.0)
  {
    for (i = 0; i < cwidth/2; i++)
      {
        t = i / ((cwidth/2) * cutoff);
        tt = exp(-.5 * t * t);
        kernel[i*2] *= tt;
        kernel[i * 2 + 1] *= tt;
      }
    kernel[1] *= exp(-.5 / (cutoff * cutoff));
  }

/* next make the special filters */ switch(ktype)
 {
 case 0:
 default:
  break;
 case 1: /* normal use cutoff of 1.5,i=0 to approximate noise in fbp version */
  start = (830 * cwidth) / 2048;
  stop = (1020 * cwidth) / 2048;
  butter(kernel, cwidth, start, .93, stop, .00028);
  break;
 case 2:
  break;
 case 3:
  walterman(kernel, cwidth, .01633, .3266, .9);
  start = (650 * cwidth) / 2048;
  stop = (1024 * cwidth) / 2048;
  black(kernel, cwidth, start, stop);
  break;
 case 4:
  walterman(kernel, cwidth, .02768, .3266, .8305);
  start = (650 * cwidth) / 2048;
  stop = (1024 * cwidth) / 2048;
  black(kernel, cwidth, start, stop);
  break;
 case 5:
  walterman(kernel, cwidth, .01633, .3266, .9);
  start = (500 * cwidth) / 2048;
  stop = (1024 * cwidth) / 2048;
  hamm(kernel, cwidth, start, stop);
  break;
 case 6:
  dog(kernel, cwidth, .5, 3.0, 1.0, -1.0);
  break;
 case 7:
```

```
    threept(kernel, cwidth, -1.0, 3.0);
    break;
  case 8:
    start = (0 * cwidth) / 2048;
    stop = (1024 * cwidth) / 2048;
    hann(kernel, cwidth, start, stop);
    break;
  case 9:
    threept(kernel, cwidth, -2.0, 5.0);
    for(i=0;i<cwidth;i++) kernel[i] *= .5;
    break;

} return(0);
}

/* make the interpolation filter.  We have various types possible.
     Type 0 is close to linear interpolation
     Type 1 is intermediate
     Type 2 is close to cubic interpolation.
     Type 3 is a Gaussian, smoother than linear
     Type 4 is constant at 1.0
     Type 5 is sharper than cubic
*/

INT
make_ifil(fr, itype, ifil, cutpt, delta)
  INT fr, itype, cutpt, delta;
  REAL32 *ifil;
{
  INT i;
  /* create the interpolation filter fr gives the number of
     complex elements in the filter*/ ifil[0] = 1.0;
  ifil[1] = 1.0;
  if(cutpt == -1) cutpt = 512;
  if(delta <= 0) delta = 20;

if(itype > 5) printf("**** special test mode cut:%d delta:%d\n",cutpt, delta);

if((itype == 7) || (itype == 9))
    {
    ifil[0] = 0.0;
    ifil[1] = 0.0;
    }
  for(i = 1; i < fr;i++)
    {
    switch(itype)
      {
      case 0:/* linear interp */
      default:
        ifil[2 * i] = sin(PI * i / (REAL) fr)/ (PI * i / (REAL) fr);
        ifil[2 * i] *= ifil[2 * i];
        break;
      case 1:/* a little bit sharper */
        ifil[2 * i] = .5 * (1.0 + cos(PI * i / (REAL)(fr)));
        break;
      case 2:/* equivalent of cubic interp */
        ifil[2 * i] = (8.0 + 9 * cos(PI * i / (REAL)(fr)) -
                  cos(3.0 * PI * i / (REAL)(fr))) / 16.0;
        break;
      case 3:
        ifil[2 * i] = exp(-2 * PI * (REAL) i * i / ((REAL)fr * fr));
        break;
      case 4:
        ifil[2 * i] = 1.0;
        break;
      case 5:
        ifil[2 * i] = sqrt(1.0 / (1.0 + pow(2.0 * i / (REAL)fr,8.0)));
        break;
      case 6:
        ifil[2 * i] = sin(PI * i / (REAL) fr)/ (PI * i / (REAL) fr);
        ifil[2 * i] *= ifil[2 * i];
        if(i > cutpt + delta) ifil[2 * i] = 0.0;
```

```
          else if(i > cutpt - delta) ifil[2 * i] *=
              .5 - .5 * sin((i - cutpt) * PI / (2.0 * delta));
          break;
        case 7:
          ifil[2 * i] = sin(PI * i / (REAL) fr)/ (PI * i / (REAL) fr);
          ifil[2 * i] *= ifil[2 * i];
          if(i <= cutpt - delta) ifil[2 * i] = 0.0;
          else if(i <= cutpt + delta)  ifil[2 * i] *=
              .5 + .5 * sin((i - cutpt) * PI / (2.0 * delta));
          break;
        case 8:
          ifil[2 * i] = (8.0 + 9 * cos(PI * i / (REAL)(fr)) -
                    cos(3.0 * PI * i / (REAL)(fr))) / 16.0;
          if(i > cutpt + delta) ifil[2 * i] = 0.0;
          else if(i > cutpt - delta) ifil[2 * i] *=
              .5 - .5 * sin((i - cutpt) * PI / (2.0 * delta));
          break;
        case 9:
          ifil[2 * i] = (8.0 + 9 * cos(PI * i / (REAL)(fr)) -
                    cos(3.0 * PI * i / (REAL)(fr))) / 16.0;
          if(i <= cutpt - delta) ifil[2 * i] = 0.0;
          else if(i <= cutpt + delta)  ifil[2 * i] *=
              .5 + .5 * sin((i - cutpt) * PI / (2.0 * delta));
          break;
        } ifil[2 * i + 1] = ifil[2 * i];
      }
    return(0);
}

/* modified Bessel function I0(x).  from Numerical Recipies in C */

REAL besseli0(x)
     REAL x;
{
 REAL ax, ans, y;
 if((ax = fabs(x)) < 3.75)
    {y = x / 3.75;
    y *= y;
    ans = 1.0 + y * (3.5156229 + y * (3.0899424 + y * (1.2067492
        + y * (0.2659732 + y * (0.360768e-1 + y * 0.45813e-2)))));
    }
  else
    {
    y = 3.75 / ax;
    ans = (exp(ax) / sqrt(ax)) * (0.39894228 + y * (0.1328592e-1
        + y * (0.225319e-2 + y * (-0.157565e-2 + y * (0.916281e-2
        + y * (-0.2057706e-1 + y * (0.2635537e-1 + y * (-0.1647633e-1
        + y * 0.392377e-2))))))));
    }
  return ans;
}

/* make the table of 1D gridding functions for quantized dx's .
            I0(beta * sqrt(1 - (2 * (u + dx)/ nt)**2) / nt
            where -nt/2  <= u <= nt/2   (nt odd)
*/

EXPORT INT
   make_grtable( nt, beta, table, nquant, gridw)
REAL    beta;
INT     nt, nquant, gridw;
REAL32 *table;
{
 REAL u, dx;
 REAL32 *vx;
 INT jx, nq;

/* table contains nt entries for each quantizied fraction nq */ for(nq = 0; nq < nquant; nq++)
    {
```

```c
    vx = table + nq * nt;

if(((nt / 2) * 2) == nt)  /* 0 <= dx < 1., nt: even. */
       dx = (nq + .5) / (REAL) nquant;
    else /* -.5 <= dx < .5, nt: odd. */
       dx = -.5 + (nq + .5) / (REAL) nquant;

/* Generate gridding function for this fraction */ for(jx = 0; jx < nt; jx++)
      {
       u = jx - nt/2 + dx;
       vx[jx] = gridfcn(beta, nt, u);
      }

.}
  if(debug) for(jx = 0; jx < nt;jx++) printf("k:%d grtable:%g\n",
                                              jx,table[jx]);
  if(gridw <= 0) return(0);

/* create the feathering table for transition between low and high freq */
 vx = table + nquant * nt;

for(jx = 0; jx < gridw * 2; jx++)
   {
    vx[2 * jx] = .5 - .5 * sin((jx - gridw) * PI / (2.0 * gridw));
    vx[2 * jx + 1] = vx[2 * jx];
   } return(0);

}

/* make the transformed grid function used to normalize the
   image */

INT
make_imgwin(trecParams, imgwin)
TREC_PARAMS *trecParams;
REAL32 *imgwin;
{
 INT i, jx;
 REAL u, scale;
 REAL32 *line;
 for(jx = 0; jx < trecParams->fwidth; jx++) imgwin[jx] = 0.0;

for(jx = 0; jx <= trecParams->nt/2; jx++)
   {
    u = jx;
    imgwin[jx * 2] = gridfcn(trecParams->beta, trecParams->nt, u);
    if(debug) printf("jx:%d imgwin:%g\n",jx, imgwin[jx * 2]);
   } rfftsh(imgwin, trecParams->fwidth, 1, 1, 1);

if(debug) printf("imgwin:fw/2:%g 3*fw/4:%g fw-1:%g\n",
                    imgwin[trecParams->fwidth / 2],
                    imgwin[3 * trecParams->fwidth / 4],
                    imgwin[trecParams->fwidth - 1]);
 if(debug)
   {
    line = (REAL32 *) malloc (trecParams->fwidth * 8);
    for(jx = 0; jx < trecParams->fwidth * 2; jx++) line[jx] = 0.0;

for(jx = 0; jx <= trecParams->nt; jx++)
      {
       u = jx / 2.0;
       line[jx * 2] = gridfcn(trecParams->beta, trecParams->nt, u);
      } rfftsh(line, trecParams->fwidth * 2, 1, 1, 1);

printf("line:fw:%g 5fw/4:%g 3fw/2:%g 7fw/4:%g 2fw-1:%g\n",
             line[trecParams->fwidth],
             line[5 * trecParams->fwidth / 4],
             line[3 * trecParams->fwidth / 2],
```

```
                    line[7 * trecParams->fwidth / 4],
                    line[2 * trecParams->fwidth - 1]);
    free(line);

} scale = trecParams->scale * .9932 * PI * PI /
    ((REAL)trecParams->pviews * trecParams->cwidth);

if(trecParams->cb) scale *= .5;

scale = sqrt(scale);

for(i=0;i<trecParams->fwidth;i++)
    if(imgwin[i] != 0.0)
       imgwin[i] = scale / (imgwin[i] * trecParams->fwidth);

return(0);
}

/* the gridding function in the transform domain */

PRIVATE REAL gridfcn(beta, nt, u)
REAL beta;
INT nt;
REAL u;
{
 REAL usqr, besseli0();
 usqr = u * u * 4.0 / (nt * nt);
 return (besseli0(beta * sqrt(1.0 - usqr)) / besseli0(beta));
/*
 usqr = TWOPI * u / nt;
 return(.42323 + .49755 * cos( usqr) + .07922 * cos(2 * usqr));
*/

}

/* kernel building routines.  These implement various filters which
   are multiplied times the kernel
*/

/* butter: a Butterworth filter */
PRIVATE INT
butter(kernel, cwidth, ip, pval, is, sval)
REAL32 *kernel;
INT cwidth, ip, is;
REAL pval,sval;
{
 REAL e1, e2, e4, order, fm, filter;
 INT i;

e1 = sqrt(1.0/pval - 1.0);
 e2 = e1 * e1;
 e4 = e2 * e2;

order = log(((1.0 / (sval * sval)) - 1.0)/(e4 + 2.0 * e2)) /
   log((REAL)is/(REAL)ip);
 fm = (REAL) ip / pow(e1 * sqrt(2.0 + e2),2.0 / order);

for(i = 0; i < cwidth / 2;i++)
   {
    filter = 1.0 / (sqrt(1.0 + pow((REAL)i / fm, order)));
    kernel[2 * i] *= filter;
    if(i > 0) kernel[2 * i + 1] *= filter;
   } kernel[1] *= filter; /* use last value for kernel[1] */ return(0);

}

/* Blackman filter */
PRIVATE INT
```

```
black(kernel, cwidth, start, stop)
REAL32 *kernel;
INT cwidth, start, stop;
{
 INT i, nw;
 REAL filter;

nw = stop - start;
 for(i = 0; i < cwidth / 2;i++)
   {
    if(i < start) filter = 1.0;
    else if(i > stop) filter = 0.0;
    else filter = .42 - .5 * cos(PI * (i - start) / nw + PI) +
      .08 * cos(2.0 * (PI * (i - start) / nw + PI));

kernel[2 * i] *= filter;
    if(i > 0) kernel[2 * i + 1] *= filter;
   }
  kernel[1] *= filter;

return(0);

}
/* Hanning filter */
PRIVATE INT
hann(kernel, cwidth, start, stop)
REAL32 *kernel;
INT cwidth, start, stop;
{
 INT i, nw;
 REAL filter;

nw = stop - start;

for(i = 0; i < cwidth / 2;i++)
   {
    if(i < start) filter = 1.0;
    else if(i > stop) filter = 0.0;
    else filter = .5 * (1.0 - cos(PI * (i - start) / nw + PI));

kernel[2 * i] *= filter;
    if(i > 0) kernel[2 * i + 1] *= filter;
   }
  kernel[1] *= filter;

return(0);

}

/* Hamming filter */
PRIVATE INT
hamm(kernel, cwidth, start, stop)
REAL32 *kernel;
INT cwidth, start, stop;
{
 INT i, nw;
 REAL filter;

nw = stop - start;
 for(i = 0; i < cwidth / 2;i++)
   {
    if(i < start) filter = 1.0;
    else if(i > stop) filter = 0.0;
    else filter = .54 - .46 * cos(PI * (i - start) / nw + PI);

kernel[2 * i] *= filter;
    if(i > 0) kernel[2 * i + 1] *= filter;
   }
  kernel[1] *= filter;

return(0);

}

/* Difference of Gaussians filter */
  PRIVATE INT
```

```
dog(kernel, cwidth, sigma1, scale1, sigma2, scale2)
REAL32 *kernel;
INT cwidth;
REAL sigma1, scale1, sigma2, scale2;
{
 INT i;
 REAL32 filter[2048];
 REAL gauss(), x;

for (i = 0; i < cwidth; i++)
   {
    x = cwidth / 2 - i;
    filter[i] = scale1 * gauss(x, sigma1) + scale2 * gauss(x, sigma2);
   }
 rfftsh(filter, cwidth, 0, 1);
 /*
  * some ad hoc corrections until I take the time to understand what is
  * going on
  */ x = 1.0 / filter[2];
 for (i = 0; i < cwidth; i ++)
   {
    filter[i] *= x;
   }
 filter[0] = 1.0;

for (i = 0; i < cwidth; i ++)
   {
    kernel[i] *= filter[i];
   } return(0);

}

/* Three point filter */
PRIVATE INT
threept(kernel, cwidth, c1, c2)
REAL32 *kernel;
INT cwidth;
REAL c1, c2;
{
 INT i;
 REAL32 filter[2048];
 REAL x;

for (i = 0; i < cwidth; i++)
   {
    filter[i] = 0.0;
   }
 filter[cwidth / 2 - 1] = c1;
 filter[cwidth / 2] = c2;
 filter[cwidth / 2 + 1] = c1;

rfftsh(filter, cwidth, 0, 1);
 /*
  * some ad hoc corrections until I take the time to understand what is
  * going on
  */ filter[0] = 1.0;
 x = filter[2];
 filter[1] /= x;
 for (i = 2; i < cwidth; i += 2)
   {
    filter[i] /= x;
    filter[i + 1] = filter[i];
   } for(i=0;i<cwidth;i++) kernel[i] *= filter[i];

return(0);

}
```

```
/* Walterman head kernel:c1 * exp(-c2|x|) + c3 * delta(x) */
PRIVATE INT
walterman(kernel, cwidth, c1, c2, c3)
REAL32 *kernel;
INT cwidth;
REAL c1, c2, c3;
{
  INT i;
  REAL32 filter[2048];
  REAL x;

for (i = 0; i < cwidth; i++)
    {
      x = cwidth / 2 - i;
      if(x < 0.0) x = -x;
      filter[i] = c1 * exp(-c2 * x);
    }
  filter[cwidth/2] += c3;

rfftsh(filter, cwidth, 0, 1);
  /*
   * some ad hoc corrections until I take the time to understand what is
   * going on
   */

/* the head kernel is set up as a deconvolution */
  filter[0] = 1.0;
  x = filter[2];
  filter[1] = x / filter[1];
  for (i = 2; i < cwidth; i += 2)
    {
      filter[i] = x / filter[i];
      filter[i + 1] = filter[i];
    } for(i=0;i<cwidth;i++) kernel[i] *= filter[i];

return(0);

}

PRIVATE REAL
gauss(x, sigma)
  REAL x, sigma;
{
  x = x / sigma;
  return exp(-(x * x / 2.0));
}

/******************* End Of trecTable.c ********************/

/*
 * trec.h  -- Definitions for trec
 *
 *      ===> trec: Imatron TBP Reconstruction
 *
 * Revision History(latest updates first!):
 *      3/12/93(jonh) New.
 */ define PI 3.141592654
define TWOPI 6.283185307
#define TESTR1 3  /* code to indicate an alternate recon (test geometry) */
#define SAVEC 1   /* bit position of savec bit in saveflg */
#define SAVET 2   /* bit position of savet bit in saveflg */
define NCALC 8   /* size of ncalc for cone beam */ typedef struct
{
```

```c
  float re;
  float im;
}
COMPLEX32;

/* this structure holds all the parameters that govern the reconstruction
   process from rebinning through final image */
typedef struct TRECPARAMS
{
  INT32 nviews;  /* number of views over 360 degrees */
  INT32 nsamps;  /* number of samples per view */
  INT32 pviews;  /* number of views in parallel sinogram after rebinning */
  INT32 minviews; /* min number of fan beam views (calc by RBtable) */
  INT32 rwidth;  /* width of the rebinned parallel sinogram */
  INT32 rot;     /* number of views to rotate */
  INT32 dofold;  /* whether to fold or not */
  INT32 docf;    /* whether to do corner-filling or not */
  INT32 doflip;  /* whether to flip or not */
  INT32 si;      /* smooth interpolation filter if fr < 1 */
  INT32 cb;      /* do cone beam recon */
  INT32 nl;      /* order of theta interpolations in rebinning */
  INT32 nk;      /* order of s interpolations in rebinning */
  INT32 reverse;/* true if rotation is reverse */
  INT32 fwidth;  /* width (and height) of the Fourier image */
  INT32 cwidth;  /* size (in R32's) of the convolution kernel */
  INT32 iwidth;  /* width (and height) of the output image */
  INT32 nt;      /* size of tbp convolution */
  INT32 nq;      /* size of grid table */
  INT32 fr;      /* length of interpolation filter (in complex elements)*/
  INT32 gridr;   /* radius of transition from first to second gridding fcn */
  INT32 gridw;   /* half width of transition from first to second gridding fcn */
  INT32 ktype;   /* type of convolution kernel */
  INT32 itype;   /* type of interpolation kernel */
  INT32 zout;    /* zero out image outside of recon circle */
  INT32 npviews;/* number of phantom views */
  INT32 cfblim; /* corner fill const */
  INT32 cfslim; /* corner fill const */
  REAL fanang;  /* fan angle in radians */
  REAL reconr;  /* recon radius 0 to 1 */
  REAL coner;   /* cone radius */
  REAL cbdist;  /* cone beam distance */
  REAL rscale;  /* rebinning scale factor */
  REAL scale;   /* tbp scale factor */
  REAL cutoff;  /* cutoff for smoothing filter */
  REAL sampoffset; /* offset of samples wrt center of fan (usually 0) */
  REAL clip2d;  /* clip2d parameter in rebinning */
  REAL tshift;  /* shift for theta0 in rebinning */
  REAL beta;    /* beta for tbp gridding function */
  REAL ecl;     /* const for theta interps in rebinning */
  REAL eck;     /* const for s interps in rebinning */
  REAL rl;      /* reach for theta interps in rebinning */
  REAL rk;      /* reach for s interps in rebinning */
  REAL x0;      /* position of center of image (-1 to 1) */
  REAL y0;      /* position of center of image (-1 to 1) */
  REAL32 ctmin; /* minimum CT number (0) */
  REAL32 ctmax; /* max CT number (4095) */
  REAL32 ctconst; /* const added to ct numbers a la Siemens */
} TREC_PARAMS;

/* this structure holds all the memory pointers for tables */
typedef struct TRECTABLES
{
  UINT32 memtot; /* total memory used in tables */
  REAL32 *phi;   /* phi table for rebinning */
  REAL32 *psi;   /* psi table for rebinning */
  UINT16 *nnsigma; /* nnsigma table for rebinning */
  UINT16 *nnbeta;  /* nnbeta table for rebinning */
  REAL32 *kernel; /* kernel */
  REAL32 *ifil;  /* bp interp filter */
  REAL32 *weights; /* weights for FFT's */
  REAL32 *grtable; /* table of gridding values */
  REAL32 *feather; /* feathering for transition between gridding fcns */
  REAL32 *imgwin;  /* transformed grid fcn for normalization of image */
  REAL32 *ramp;    /* used in shift */
} TREC_TABLES;
```

```c
/* this structure holds all the memory pointers for data memory */
/* this includes intermediate results and work areas */
/* the memory areas need not be disjoint, two named areas may share
   memory: one name may be used by one part of recon, a second by
   another at a different time.
*/
typedef struct TRECMEMORY
{
 UINT32 memtot; /* total memory used for data */
 CHAR *chunk1; /* first memory chunk */
 UINT32 size1; /* size of first chunk */
 CHAR *chunk2; /* second memory chunk */
 UINT32 size2; /* size of second chunk */
 CHAR *chunk3; /* third memory chunk */
 UINT32 size3; /* size of third chunk */
 CHAR *chunk4; /* fourth memory chunk */
 UINT32 size4; /* size of fourth chunk */
 REAL32 *fansino; /* fan beam sinogram input data */
 REAL32 *fansino2; /* fan beam sinogram input data */
 REAL32 *rbtmem; /* rebinning temp memory */
 REAL32 *view1; /* view 1 size: cwidth */
 REAL32 *view2; /* view 2 size: cwidth */
 REAL32 *view3; /* view 3 size: cwidth */
 REAL32 *view4; /* view 4 size: cwidth */
 REAL32 *gridtmp; /* temp area for gridding size: cwidth */
 REAL32 *cbview1; /* cbview1 size: cwidth */
 REAL32 *cbview2; /* cbview2 size: cwidth */
 REAL32 *cbview3; /* cbview3 size: cwidth */
 REAL32 *cbview4; /* cbview4 size: cwidth */
 REAL32 *shiftmem;  /* shift temp memory size: cwidth */
 INT32  *vkx0; /* backp memory size: cwidth / 2*/
 INT32  *vky0; /* backp memory size: cwidth / 2*/
 REAL32 **vvx; /* backp memory size: cwidth / 2*/
 REAL32 **vvy; /* backp memory size: cwidth / 2*/
 REAL32 *vs; /* backp memory size: cwidth / 2*/
 REAL32 *cbtemp1; /* used in fbackpcb size: cwidth*/
 REAL32 *cbtemp2;/* used in fbackpcb size: cwidth*/
 REAL32 *cbcoords;/* used in cbcc size: cwidth * 8*/
 REAL32 *xsino; /* intermediate rebinning sinogram */
 REAL32 *xsino2; /* intermediate rebinning sinogram */
 REAL32 *isino; /* intermediate rebinning sinogram */
 REAL32 *isino2; /* intermediate rebinning sinogram */
 REAL32 *psino; /* parallel beam sinogram */
 REAL32 *psino2; /* parallel beam sinogram */
 REAL32 *fimage; /* Real image or Fourier transform of image */
 INT16 *image; /* i16 output image */
} TREC_MEMORY;

/********************* end trec.h ***********************/
 /*
 * File Name: trecMisc.c
 *
 * Author   : Jon Harman
 *
 * Brief Description: Misc functions for trec.
 *
 * Copyright 1993 Imatron, Inc.
 *
 * Command Line Synopsis:
 *
 * Long Description:
 *
 * Deficiencies / bugs:
 *
 * Return (status) codes, error messages:
 *
 * Abbreviations used:
 *
 * Revision History (latest updates first!): 3/15/93(jonh) New.
 */
/* LINTLIBRARY *//* suppresses some unneeded lint messages */

/* 1.) "Imported" data types and defines: */
/* 1.a.) Standard C include files  */
 #include       <stdio.h>
 #include       <math.h>
 #include       <string.h>
```

```c
/* #include        <sys/types.h> */
#ifdef      MC860
#include        <mcos.h>
#include        <sal_defs.h>
endif /* 1.b.) Imatron ../include files */
include        "../include/imatron.h"  /* first Imatron include */

/* 1.c.) Project include files                          */
#include        "trec.h"

/* 1.d.) Other include files                            */

/* 2.) Externals defined in this file (declarations onry): */
FORWARD INT rfftsh();
FORWARD INT rfft2dsh();
FORWARD INT allocmem();

/* 3.) "Imported" externals: */
/* 3.a.) Imported from standard C Library               */
IMPORT CHAR *malloc();

/* 3.b.) Imported from ../xxxxx                 */

/* 3.c.) Imported from other files in this dtrectory */
/* 3.d.) Imported from elsewhere */

/* 4.) "Private" data types, defines, data and code */
#ifdef MC860
IMPORT REAL32 salcache[4];
#else
#define SAL_NC  1
#define SAL_NCC 1
#define SAL_CCN 1
#define SAL_CNC 1
#define SAL_CN  1
#define SAL_CC  1
#define SAL_C   1
PRIVATE REAL32 salcache[2048];
endif /* 5.) Exported Functions and Data: */

/* a shell for rfft which includes inv and flip */
/* inv is a boolean for inverse rather than the dir (+-1) used by Mercury */
/*
 * flip causes a 180deg shift in the position of the spatial data by
 * multiplying the transform by +-1
 */
/* doscale = TRUE does correct scaling */
INT
rfftsh(f, n, inv, flip, doscale)
  REAL32 *f;
  INT n, inv, flip, doscale;
{
  INT dir, i;
  REAL32 neg1 = -1, scale, *ca = salcache;

if (inv)
    dir = -1;
  else
    dir = 1;

if (flip && inv)
  {
    vsmul(&f[2], 4, &neg1, &f[2], 4, n / 4);
    vsmul(&f[3], 4, &neg1, &f[3], 4, n / 4);
  } rfft(f, n, dir);

if (flip && !inv)
  {
```

```c
      vsmul(&f[2], 4, &neg1, &f[2], 4, n / 4);
      vsmul(&f[3], 4, &neg1, &f[3], 4, n / 4);
    }
    if (doscale)
    {
      if (inv)
        scale = 1.0 / (REAL) n;
      else
        scale = .5;
      vsmul(f, 1, &scale, f, 1, n);
    }
    return (0);
}

/* this just does the flip from rfftsh */
EXPORT INT
flip(f, n)
  REAL32 *f;
  INT n;
{
  REAL32 neg1 = -1;
  vsmul(&f[2], 4, &neg1, &f[2], 4, n / 4);
  vsmul(&f[3], 4, &neg1, &f[3], 4, n / 4);
  return (0);
}

/* a shell for 2D rfft which includes inv and flip */
INT rfft2dsh(f, nc, nr, inv, flip, doscale)
REAL32 *f;
INT nc, nr, inv, flip, doscale;
{
 INT dir, i, j, itwo = 2, twonc = 2 * nc, ni, ii, jj, kk, mtwo=-2,n2;
 REAL32 neg1 = -1, scale, two = 2.0,half = .5;
 PRIVATE REAL32 cnq[4096];

if(inv) dir = -1;
  else dir = 1;

if (flip && inv)
  {
    for (i = 0; i < nr; i += 2)
    {
     /* even rows */
      vsmul(&f[i * nc + 2], 4, &neg1, &f[i * nc + 2], 4, nc / 4);
      vsmul(&f[i * nc + 3], 4, &neg1, &f[i * nc + 3], 4, nc / 4);
     /* odd rows */
      vsmul(&f[(i + 1) * nc + 4], 4, &neg1, &f[(i + 1) * nc + 4], 4,
           nc / 4 - 1);
      vsmul(&f[(i + 1) * nc + 5], 4, &neg1, &f[(i + 1) * nc + 5], 4,
           nc / 4 - 1);
    }
    vsmul(&f[2 * nc], 4 * nc, &neg1, &f[2 * nc], 4 * nc, nr / 4);
    vsmul(&f[3 * nc], 4 * nc, &neg1, &f[3 * nc], 4 * nc, nr / 4);
    vsmul(&f[2 * nc + 1], 4 * nc, &neg1, &f[2 * nc + 1], 4 * nc, nr / 4);
    vsmul(&f[3 * nc + 1], 4 * nc, &neg1, &f[3 * nc + 1], 4 * nc, nr / 4);
  }
#if 0
  if (flip && inv)
  {
    for (i = 0; i < nr; i += 2)
    {
      vsmul(&f[i * nc + 2], 4, &neg1, &f[i * nc + 2], 4, nc / 4);
      vsmul(&f[i * nc + 3], 4, &neg1, &f[i * nc + 3], 4, nc / 4);
      vsmul(&f[(i + 1) * nc], 4, &neg1, &f[(i + 1) * nc + 4], 4,
           nc / 4);
      vsmul(&f[(i + 1) * nc + 1], 4, &neg1, &f[(i + 1) * nc + 5], 4,
           nc / 4);
    } vsmul(&f[nr * nc + 2], 4, &neg1, &f[nr * nc + 2], 4, nc / 4);
    vsmul(&f[nr * nc + 3], 4, &neg1, &f[nr * nc + 3], 4, nc / 4);
  }
endif ifndef CSPI
 rfft2d(f,nc,nr,dir);
```

```c
#else
 if(dir == 1)
   {
    for(i=0;i<1024;i++) cnq[i] = -1.0;
    rft2fr_(f, cnq, &itwo, f, &nr, &nc);
    /* do packing of cnq array into mercury format here */
    ni = nr / 2 - 1;
    ii = -nc;
    jj = 2 * nc;
    vmov_(f + (nr - 1)* nc, &ii, f + 2 * nc, &jj, &ni);
    ii = nc;
    vmov_(f + nc + 1, &ii, f + 3 * nc, &jj, &ni);
    f[nc] = f[nc * nr / 2];
    ii = 1;
    vmov_(cnq, &ii, f + 1, &nc, &nr);
    f[nc + 1] = cnq[nr];
   }
  else
   {
    /* do unpacking from mercury format col 1 to cnq array here */
    /* something is fishy here.  cnq is a nr * 2 complex array, yet I
       fill up only half of it.  The output equals mercury though.
    */
    ii = 1;
    vclr(cnq, 1, nr * 2);
    vmov_(f + 1, &nc, cnq, &ii, &nr);
    cnq[nr] = f[nc + 1];
    cnq[nr + 1] = 0.0;
    cnq[1] = 0.0;
/*
    ni = nr / 2 - 1;
    vmov_(cnq+2, &itwo, cnq+nr-2, &mtwo, &ni);
    vmov_(cnq+3, &itwo, cnq+nr-1, &mtwo, &ni);
    this is close, but not quite right.  I give up!
*/ cnq[0] *= .5;

n2 = nr * 2;
    vsmul_(cnq, &ii, &two, cnq, &ii, &n2);

ni = nc / 2 - 1;
    /* fix up cols 0 and 1 */
    ii = nc;
    jj = 2 * nc;
    vmov_(f + 3 * nc, &jj, f + nc + 1, &ii, &ni);
    jj = -nc;
    vneg_(f + nc + 1, &ii, f + (nr - 1) * nc + 1, &jj, &ni);
    ii = 2 * nc;
    jj = 1;
    vmov_(f + 2 * nc, &ii, cnq + 2 * nr, &jj, &ni); /* temp storage */
    ii = 1;
    jj = -nc;
    vmov_(cnq + 2 * nr, &ii, f + (nr - 1) * nc, &jj, &ni);
    f[nc * nr / 2] = f[nc];
    ii = -nc;
    jj = nc;
    vmov_(f + (nr - 1) * nc, &ii, f + nc, &jj, &ni);
    f[1] = 0.0;
    f[nr * nc /2 + 1] = 0.0;
    rft2ir_(f, cnq, &itwo, f, &nr, &nc);
   }
endif if (flip && !inv)
   {
    for (i = 0; i < nr; i += 2)
     {
      vsmul(&f[i * nc + 2], 4, &neg1, &f[i * nc + 2], 4, nc / 4);
      vsmul(&f[i * nc + 3], 4, &neg1, &f[i * nc + 3], 4, nc / 4);
      vsmul(&f[(i + 1) * nc + 4], 4, &neg1, &f[(i + 1) * nc + 4], 4,
           nc / 4 - 1);
      vsmul(&f[(i + 1) * nc + 5], 4, &neg1, &f[(i + 1) * nc + 5], 4,
           nc / 4 - 1);
     }
    vsmul(&f[2 * nc], 4 * nc, &neg1, &f[2 * nc], 4 * nc, nr / 4);
    vsmul(&f[3 * nc], 4 * nc, &neg1, &f[3 * nc], 4 * nc, nr / 4);
```

```
      vsmul(&f[2 * nc + 1], 4 * nc, &neg1, &f[2 * nc + 1], 4 * nc, nr / 4);
      vsmul(&f[3 * nc + 1], 4 * nc, &neg1, &f[3 * nc + 1], 4 * nc, nr / 4);
  } if(doscale)
    {
       if(inv) scale = 1.0 / ((REAL)nc * (REAL)nr);
       else scale = .5;
       vsmul(f,1,&scale,f,1,nc * nr);
    } return(0);
 }

PRIVATE INT
imax(a, b)
   INT a, b;
{
  if (a > b)
    return (a);
  return (b);
}

/*
    * allocate data memory. We calculate the sizes of the biggest
      chunks of memory needed.  Then distribute the actual memory
      needs within the chunks.  Note that there are usually
      two big chunks in use: fansino, xsino: first rebin step
                             xsino, isino: second rebin step
                             isino, psino: final rebin step
                             psino, fimage: backprojection

*/

EXPORT INT
allocmem(trecParams, trecMemory, dorebin)
   TREC_PARAMS *trecParams;
   TREC_MEMORY *trecMemory;
   INT dorebin;
{
   INT i, fansize, psize, minviews1, rsize, tsize, fsize;

/* calc sizes needed for the chunks first */ if(dorebin)
     minviews1 = trecParams->minviews + 2 * trecParams->nl;
   else
     minviews1 = 4;

/* tsize is the size of temp memory chunk */
   /* rebinning temp */
   tsize = trecParams->rwidth;

/* area for views and other data during backprojection, shared with rbtemp */
   tsize = imax(tsize, trecParams->cwidth * 9);
   if(trecParams->cb)
      tsize = imax(tsize, trecParams->cwidth * (15 + NCALC));
   tsize *= sizeof(REAL32);

fansize = minviews1 * trecParams->nsamps * sizeof(REAL32);
   psize = trecParams->rwidth * trecParams->pviews * sizeof(REAL32);
   rsize = imax(fansize, psize); /* size for rebinning memory chunks*/

/* Fourier image size */
   fsize = trecParams->fwidth * (trecParams->fwidth + 2) * sizeof(REAL32);

trecMemory->size1 = imax(fsize, rsize);
   trecMemory->size2 = rsize;
   trecMemory->size3 = 4096;/* not used */
   trecMemory->size4 = tsize;
   if(trecParams->cb)
     {
      trecMemory->size2 = rsize;
      trecMemory->size3 = rsize;
      trecMemory->size4 = tsize;
     }
```

```
/* for the 860 */
trecMemory->size1 = ((4095 + trecMemory->size1) / 4096) * 4096;
trecMemory->size2 = ((4095 + trecMemory->size2) / 4096) * 4096;
trecMemory->size3 = ((4095 + trecMemory->size3) / 4096) * 4096;
trecMemory->size4 = ((4095 + trecMemory->size4) / 4096) * 4096;

#ifdef MC860
  trecMemory->chunk1 = (CHAR *) memalign(4096, trecMemory->size1);
  i = mcntl(MC_CACHE, trecMemory->chunk1, trecMemory->size1);
  if (i)
    printf("mcntl error for chunk1.\n");
  trecMemory->chunk2 = (CHAR *) memalign(4096, trecMemory->size2);
  i = mcntl(MC_CACHE, trecMemory->chunk2, trecMemory->size2);
  if (i)
    printf("mcntl error for chunk2.\n");
  trecMemory->chunk3 = (CHAR *) memalign(4096, trecMemory->size3);
  i = mcntl(MC_CACHE, trecMemory->chunk3, trecMemory->size3);
  if (i)
    printf("mcntl error for chunk3.\n");
  trecMemory->chunk4 = (CHAR *) memalign(4096, trecMemory->size4);
  i = mcntl(MC_CACHE, trecMemory->chunk4, trecMemory->size4);
  if (i)
    printf("mcntl error for chunk4.\n");
#else
  trecMemory->chunk1 = (CHAR *) malloc(trecMemory->size1);
  trecMemory->chunk2 = (CHAR *) malloc(trecMemory->size2);
  trecMemory->chunk3 = (CHAR *) malloc(trecMemory->size3);
  trecMemory->chunk4 = (CHAR *) malloc(trecMemory->size4);
endif if (!trecMemory->chunk1)
  {
    printf("trec. Cannot get memory(%d) for chunk1, memtot:%d.\n",
        trecMemory->size1, trecMemory->memtot);
    return (-1);
  }
  trecMemory->memtot += trecMemory->size1;

if (!trecMemory->chunk2)
  {
    printf("trec. Cannot get memory(%d) for chunk2, memtot:%d.\n",
        trecMemory->size2, trecMemory->memtot);
    return (-1);
  }
  trecMemory->memtot += trecMemory->size2;

if (!trecMemory->chunk3)
  {
    printf("trec. Cannot get memory(%d) for chunk3, memtot:%d.\n",
        trecMemory->size3, trecMemory->memtot);
    return (-1);
  }
  trecMemory->memtot += trecMemory->size3;

if (!trecMemory->chunk4)
  {
    printf("trec. Cannot get memory(%d) for chunk4, memtot:%d.\n",
        trecMemory->size4, trecMemory->memtot);
    return (-1);
  }
  trecMemory->memtot += trecMemory->size4;

/*
   * next we apportion out the data areas inside the chunk. This is not so
   * easy.  Any changes in program flow must carefully be examined for
   * effect on memory allocation
   */ trecMemory->fansino = (REAL32 *) trecMemory->chunk1;
  trecMemory->xsino = (REAL32 *) trecMemory->chunk2;
  trecMemory->isino = (REAL32 *) trecMemory->chunk1;
  trecMemory->psino = (REAL32 *) trecMemory->chunk2;
  trecMemory->rbtmem =(REAL32 *) trecMemory->chunk4;
  trecMemory->shiftmem = (REAL32 *) trecMemory->chunk4;
  trecMemory->vkx0 = (INT32 *) (trecMemory->shiftmem + trecParams->cwidth);
  trecMemory->vky0 = trecMemory->vkx0 + trecParams->cwidth/2;
```

```
    trecMemory->vvx = (REAL32 **) (trecMemory->vky0 + trecParams->cwidth/2);
    trecMemory->vvy = trecMemory->vvx + trecParams->cwidth/2;
    trecMemory->vs = (REAL32 *) trecMemory->vvy + trecParams->cwidth / 2;
    trecMemory->view1 = (REAL32 *) trecMemory->vs + trecParams->cwidth / 2;
    trecMemory->view2 = trecMemory->view1 + trecParams->cwidth;
    trecMemory->view3 = trecMemory->view2 + trecParams->cwidth;
    trecMemory->view4 = trecMemory->view3 + trecParams->cwidth;
    trecMemory->gridtmp = trecMemory->view4 + trecParams->cwidth;
    trecMemory->fimage = (REAL32 *) trecMemory->chunk1;
    trecMemory->image = (INT16 *) trecMemory->chunk1;
    if(trecParams->cb)
      {
        trecMemory->fansino = (REAL32 *) trecMemory->chunk2;
        trecMemory->fansino2 = (REAL32 *) trecMemory->chunk3;
        trecMemory->xsino = (REAL32 *) trecMemory->chunk1;
        trecMemory->xsino2 = (REAL32 *) trecMemory->chunk2;
        trecMemory->isino = (REAL32 *) trecMemory->chunk3;
        trecMemory->isino2 = (REAL32 *) trecMemory->chunk1;
        trecMemory->psino = (REAL32 *) trecMemory->chunk2;
        trecMemory->psino2 = (REAL32 *) trecMemory->chunk3;
        trecMemory->cbview1 = trecMemory->view4 + trecParams->cwidth;
        trecMemory->cbview2 = trecMemory->cbview1 + trecParams->cwidth;
        trecMemory->cbview3 = trecMemory->cbview2 + trecParams->cwidth;
        trecMemory->cbview4 = trecMemory->cbview3 + trecParams->cwidth;
        trecMemory->cbtemp1 = trecMemory->cbview4 + trecParams->cwidth;
        trecMemory->cbtemp2 = trecMemory->cbtemp1 + trecParams->cwidth;
        trecMemory->gridtmp = trecMemory->cbtemp2 + trecParams->cwidth;
        trecMemory->cbcoords = trecMemory->gridtmp + trecParams->cwidth;
      }
    return (0);
}

/*
 * fill in extra views for a fan beam sinogram. This version assumes that
 * sampoffset = 0, hence that -isigma = width - isigma - 1
 * view: view number of view to fillin,
 * view0: first existing view
 * ngood: number of existing views
 * width: width of views
 * fanang: fanangle in radians
 */

EXPORT INT
fanfillin(sino, view, view0, ngood, nviews, width, fanang)
  REAL32 *sino;
  INT view, view0, ngood, nviews, width;
  REAL fanang;
{
  INT i, j, k, n, isigma, iview, lview = view0 + ngood - 1;
  INT vhalf = view0 + ngood/2;
  REAL d0, d1, dsigma, sigma, sigma0, beta, rview;
  REAL32 *sino1 = sino + view * width;

/*
   * we use the relation sino(sigma,beta) = sino(-sigma,PI + beta + 2 *
   * sigma) if sampoffset = 0 then -sigma will fall at an integer we do
   * linear interpolation between views
   */ dsigma = fanang / (width - 1);
  sigma0 = -fanang / 2.0;
  beta = view * TWOPI / (REAL) nviews;

for (isigma = 0, sigma = sigma0; isigma < width; isigma++, sigma += dsigma)
    {
      if (view > vhalf)
        rview = (beta - PI + 2 * sigma) * nviews / TWOPI;
      else
        rview = (beta + PI + 2 * sigma) * nviews / TWOPI;
      iview = rview;
      if ((iview < view0) || (iview >= lview))
        sino1[isigma] = 0.0;          /* outside */
      else
        {
          d0 = rview - iview;
          d1 = 1 - d0;
```

```
        k = iview * width + width - isigma - 1;
        sino1[isigma] = d1 * sino[k] + d0 * sino[width + k];
      }
    } return (0);
}

/* read in the input sinogram from a file.  Can be fan beam or parallel.
   returns number of views actually read, or -1 if not enough
*/
EXPORT INT
  readinput(fansino, psino, trecParams, dorebin, skip, fp)
REAL32 *fansino, *psino;
TREC_PARAMS *trecParams;
INT dorebin, skip;
FILE *fp;
{
 INT nsamps = trecParams->nsamps, nl = trecParams->nl;
 INT psize, ssize, viewsread, nclr;
 REAL32 *readstart;

if (dorebin)
   {
     if (skip)
       fread(fansino, sizeof(REAL32), skip * nsamps, fp);
     vclr(fansino, 1, nl * nsamps);
     readstart = fansino + nl * nsamps;
     ssize = (trecParams->minviews + nl) * nsamps;
     nclr = ssize;
     ssize = fread(readstart, sizeof(REAL32), ssize, fp);
     viewsread = ssize / nsamps;
     nclr = nclr - viewsread * nsamps;
     if(nclr > 0) vclr(fansino + (viewsread + nl) * nsamps, 1, nclr);
     if(viewsread < trecParams->minviews) viewsread = -1;
   }
 else
   {
     psize = trecParams->rwidth * trecParams->pviews;
     ssize = fread(psino, sizeof(REAL32), psize, fp);
     viewsread = ssize / trecParams->rwidth;
     if(viewsread < trecParams->pviews) viewsread = -1;
   }
 return(viewsread);
}

/* mformat: put the inverse fft matrix into Mercury real 2D FFT format.
     See the Mercury documentation for a description of their format.
     One wrinkle is that I have stored the last complex column as the
     last two rows.
  */
INT mformat(image, nx, ny)
REAL32 *image;
INT nx, ny;
{INT i;
 REAL32 t;

/* deal with the first complex column */ image[0] *= 2.0;
  for(i = 1; i < ny/2;i++)
    {
      image[i * nx] += image[(ny - i) * nx];
      image[i * nx + 1] -= image[(ny - i) * nx + 1];
    } t = image[ny / 2 * nx];
  for(i=ny/2 - 1;i > 0;i--)
    {
      image[i * 2 * nx] = image[i * nx];
      image[(i * 2 + 1) * nx] = image[i * nx + 1];
    }
  image[nx] = 2.0 * t; /* factor of 2 seems to improve things */

/* the last complex column is stored as two extra rows.
   it gets stuffed into the second column of the packed image */
```

```
for(i=1;i < ny/2; i++)
  {
   image[nx * ny + 2 * i] += image[nx * ny + (ny - i) * 2];
   image[nx * ny + 2 * i + 1] -= image[nx * ny + (ny - i) * 2 + 1];
  } for(i = 1; i <ny/2;i++)
  {
   image[nx * 2 * i + 1] = image[nx * ny + 2 * i];
   image[nx * (2 * i + 1) + 1] = image[nx * ny + 2 * i + 1];
  } image[1] = 2.0 * image[nx * ny];
image[nx + 1] = 0.0;

return(0);

}

/* shifttransv: shift views in a sinogram.

The basis of this algorithm is that the parallel beam sinogram when
   transformed becomes a polar coordinate version of the 2D fft of the
   image.  Thus to shift the image the Fourier shift theorem can be applied
   to the sinogram.  I do this by multiplying  F(u,v) by exp(-2PI*i*sh*u) *
   exp(-2PI*i*sv*v)).  In polar coords u = r cos(view), v = r sin(view). I
   use the ramp to create r's for each point in the view then multiply by a
   scalar -2PI*sh*cos(view) (for sh).  Then I use vcos and vsin to get the
   real and imag parts of the exp. This needs two shifts, one horiz, one
   vert. This is a much slower version then shifttrans, but it is
   easy to implement in a view by view recon algorithm.

This version shifts 2 views (4 views for cone beam) at once.
   We use the fact that sin(PI - angle) = sin(angle)
                        cos(PI - angle) = -cos(angle).
   Thus the same cos and sin tables can be used for two angles at once.

*/ shifttransv(trecTables, trecMemory, trecParams, angle, view0,
          view1, view2, cbview1, cbview2)
     TREC_TABLES *trecTables;
     TREC_MEMORY *trecMemory;
     TREC_PARAMS *trecParams;
     REAL angle;
     INT view0;
     REAL32 *view1, *view2;
     REAL32 *cbview1, *cbview2;
{
 REAL32 rtemp1,rtemp2;
 INT i, width = trecParams->cwidth, fr = trecParams->fr;
 REAL sh, sv;
 REAL32 *ramp = trecTables->ramp;
 REAL32 *tmem = trecMemory->shiftmem;

sh = trecParams->x0 * width / 2;
 if(trecParams->doflip) sh = -sh;
 sv = -trecParams->y0 * width / 2;

if(fabs(sh) > 0.0)
    {
      rtemp1 = (TWOPI * sh * -cos(angle)) / width;
      vsmul(ramp, 1, &rtemp1, tmem, 1, fr * 2);
      vcos(tmem, 2, tmem, 2, fr);
      vsin(tmem + 1, 2,tmem + 1, 2, fr);
      cvmul(view1 + 2, 2,tmem + 2, 2, view1 + 2, 2, fr - 1,1);
      if(trecParams->cb)
          cvmul(cbview1 + 2, 2,tmem + 2, 2, cbview1 + 2, 2, fr - 1,1);
   /* view 0 is a special case.
      then view1 is at 0, view2 is at PI / 2.
      so cos(angle) = 1 for view1, = 0 for view2.
      for view2 this shift is not needed since tmem is a complex vector
      of all (1,0)'s.
   */
      if(view0 != 0)
         {
```

```
    /* view2 (cbview2) is at PI - angle, cos(PI - angle) = -cos(angle)
       so the vsin above needs to be negated for view2 */
    vneg(tmem + 1, 2, tmem + 1, 2, fr);
    cvmul(view2 + 2, 2,tmem + 2, 2, view2 + 2, 2, fr - 1,1);
    if(trecParams->cb)
       cvmul(cbview2 + 2, 2,tmem + 2, 2, cbview2 + 2, 2, fr - 1,1);
   }
 }
 if(fabs(sv) > 0.0)
 {
  rtemp1 = (TWOPI * sv * -sin(angle)) / width;
  vsmul(ramp, 1, &rtemp1, tmem, 1, fr * 2);
  vcos(tmem, 2, tmem, 2, fr);
  vsin(tmem + 1, 2,tmem + 1, 2, fr);
  cvmul(view1 + 2, 2,tmem + 2, 2, view1 + 2, 2, fr - 1,1);
  if(trecParams->cb)
     cvmul(cbview1 + 2, 2,tmem + 2, 2, cbview1 + 2, 2, fr - 1,1);
  if(view0 != 0)
    {
     /* here sin(PI - angle) = sin(angle) */
     cvmul(view2 + 2, 2,tmem + 2, 2, view2 + 2, 2, fr - 1,1);
     if(trecParams->cb)
        cvmul(cbview2 + 2, 2,tmem + 2, 2, cbview2 + 2, 2, fr - 1,1);
    }
  else
    /* view 0 is a special case.
       then view1 is at 0, view2 is at PI / 2.
       so sin(angle) = 0 for view1, = 1 for view2.
       */
    {
     rtemp1 = (-TWOPI * sv) / width;
     vsmul(ramp, 1, &rtemp1, tmem, 1, fr * 2);
     vcos(tmem, 2, tmem, 2, fr);
     vsin(tmem + 1, 2,tmem + 1, 2, fr);
     cvmul(view2 + 2, 2,tmem + 2, 2, view2 + 2, 2, fr - 1,1);
     if(trecParams->cb)
        cvmul(cbview2 + 2, 2,tmem + 2, 2, cbview2 + 2, 2, fr - 1,1);
    }
 } return(0);
}

/* init the Fourier image, as of now this just means zeroing it out */
INT
init_img(image, width)
REAL32 * image;
INT width;
{
 vclr(image, 1, width * (width + 2));
 return(0);
}

/* norm_image:prepare the final image.
   This entails:
   1. Normalization to eliminate doming of image due to convolution
      in the transform domain.  We multiply with the coefficients
      stored in imgwin.  The doming is separable so we can use a 1-D
      array to normalize the 2D image.  Note that a scale factor is
      hidden into the imgwin array.
   2. Adding a constant to the image if desired.  (Siemens adds 24.)
   3. Clipping the image to ctmin(0) and ctmax(4095).
   4. Fix to a 16 bit unsigned integer.
   5. Optionally zero out any area of the image outside the recon
      area.
 */
INT
   norm_image(trecTables, trecMemory, trecParams, skipint)
TREC_TABLES *trecTables;
TREC_MEMORY *trecMemory;
TREC_PARAMS *trecParams;
INT skipint; /* if true, skip conversion to an integer */
{
 REAL reconr;
 REAL32 *imgwin = trecTables->imgwin, *fimage = trecMemory->fimage;
 REAL32 clip0, clip1;
 INT i, j, iwidth = trecParams->iwidth, fwidth = trecParams->fwidth;
```

```c
/* first divide the image by the transform of the window function */
j = (fwidth - iwidth) / 2;
/* do the horizontal normalization */
for(i = j;i < j + iwidth;i++)
  vmul(imgwin + j, 1,fimage + fwidth * i + j, 1, fimage + fwidth * i + j, 1,
      iwidth);
/* do the vertical normalization and squeese down image to iwidth x iwidth */
for(i = j;i < j + iwidth;i++)
  vsmul(fimage + fwidth * i + j, 1, imgwin + i, fimage + iwidth * (i - j),
      1, iwidth);

/* add a constant */
if(trecParams->ctconst != 0.0)
  vsadd(fimage, 1, &trecParams->ctconst, fimage, 1, iwidth * iwidth);

if(skipint) return(0); /* skip the conversion to an integer */

/* clip to 0 .. 4095 */
vclip(fimage, 1, &trecParams->ctmin, &trecParams->ctmax, fimage, 1,
      iwidth * iwidth);

/* fix to int16 */
vfix(fimage, 1, trecMemory->image, 1, iwidth * iwidth);

/* zero out area outside of recon circle */
/* if iwidth != fwidth / 2 then an adjustment is needed */
reconr = trecParams->reconr * 2.0 * trecParams->iwidth /
   (REAL) trecParams->fwidth;

if(trecParams->zout)
    zero_out(trecMemory->image, trecParams->iwidth, reconr,
             trecParams->x0, trecParams->y0);
return(0);
}
/* zero out part of image outside of recon circle.
   coords are x,y.  recon circle is (x,y):x**2 + y**2 <= 1.0.
   image is centered at (xoff,yoff) width nmat.
   the integer image coordinates are changed to (x,y)
   nmat = 2 * reconr in x,y coords.
*/
EXPORT INT
zero_out(image, nmat, reconr, xoff, yoff)
UINT16 *image;
INT nmat;
REAL reconr, xoff, yoff;
{
 INT i, j, k, l;
 REAL dx, x0, y, xbeg, ys;
 UINT16 *line;

dx = 2.0 * reconr / nmat;
 x0 = xoff - reconr;
 y = yoff - reconr;
 for(j=0;j<nmat;j++)
   {line = image + j * nmat;
    ys =y * y;
    if(ys > 1.0) {for(i = 0;i < nmat;i++) line[i] = 0;}
    else
     {
      xbeg = sqrt(1.0 - ys);
      k = (-xbeg - x0) / dx;
      if(k > nmat) k = nmat;
      for(i = 0; i < k; i++) line[i] = 0;
      l = (xbeg - x0) / dx;
      if(l < k) l = k;
      if(l < 0) l = 0;
      for(i = l;i < nmat; i++) line[i] = 0;
     }
    y += dx;
   }
 return(0);
}

/******************* End Of trecMisc.c ********************/
```

```
/*
 * File Name: trecRebin.c
 *
 * Author   : Jon Harman
 *
 * Brief Description: Does rebinning based on interpolation tables.
 *
 * Copyright 1993 Imatron, Inc.
 *
 * Command Line Synopsis:
 *
 * Long Description:
 *
 * Deficiencies / bugs:
 *
 * Return (status) codes, error messages:
 *
 * Abbreviations used:
 *
 * Revision History (latest updates first!): 6/14/93(jonh) New.
 */
/* LINTLIBRARY *//* suppresses some unneeded lint messages */

/* 1.) "Imported" data types and defines: */
/* 1.a.) Standard C include files   */
#include        <stdio.h>
#include        <math.h>
#include        <string.h>
#ifndef CSPI
#include        <sys/types.h>
#endif
#ifdef      MC860
#include        <mcos.h>
#include        <sal_defs.h>
endif
/* 1.b.) Imatron ../include files */
#include        "../include/imatron.h"   /* first Imatron include */
#include        "../include/scanner_config.h" /* scanner config */

/* 1.c.) Project include files                               */
#include        "trec.h"

/* 1.d.) Other include files                                 */

/* 2.) Externals defined in this file (declarations only): */
FORWARD INT trecRebin();
PRIVATE REAL weights();
FORWARD INT allocmem();

/* 3.) "Imported" externals: */
/* 3.a.) Imported from standard C Library                    */
IMPORT CHAR *malloc();
IMPORT REAL atof();
IMPORT FILE *pu_fopen();

/* 3.b.) Imported from ../xxxxx                              */

/* 3.c.) Imported from other files in this dtrectory */

/* 3.d.) Imported from elsewhere */

/* 4.) "Private" data types, defines, data and code */
#ifdef MC860
IMPORT REAL32 salcache[4];
#else
#define SAL_NC  1
#define SAL_NCC 1
#define SAL_CNC 1
#define SAL_CN  1
#define SAL_CC  1
#define SAL_CCN 1
PRIVATE REAL32 salcache[2048];
endif
PRIVATE INT test = 0, saveinter = 0;

/* 5.) Exported Functions and Data: */
```

```
/*
 * This is the main rebinning program.  Its input is a fan beam sinogram
 * plus the rebinning tables.  Its output is the parallel beam sinogram
 */

EXPORT INT
trecRebin(trecParams, trecTables, trecMemory)
     TREC_PARAMS *trecParams;
     TREC_TABLES *trecTables;
     TREC_MEMORY *trecMemory;
{
  REAL32 beta, sigma, dsigma, sigma0;
  REAL32 accum;
  REAL32 *phi1, *fs1, *psi1, *psi0, *is0, *is1, *islim, *ps1;
  REAL32 *fansino, *xsino, *psino, *isino, *tmem;
  REAL32 *fansino2, *xsino2, *psino2, *isino2;

/* the following are handy abbreviations for elements in trecParams */
  INT nbeta, ntheta, nsigma, ns, minviews;
  INT nl2, nk2;

INT ibeta, isigma, is;

INT i, k, l;
  INT minviews1;

CHAR fname[80];
  FILE *fp;

REAL32 coeff;

/*
   memory requirements.
     fansino: minviews1 * nsamps
     xsino:   minviews * nsamps
     isino:   pviews * rwidth
     psino:   pviews * rwidth
     tmem:    max of minviews1, rwidth
     fansino != xsino xsino != isino psino != isino tmem != any other memory
   */ fansino = trecMemory->fansino;
  xsino = trecMemory->xsino;
  isino = trecMemory->isino;
  psino = trecMemory->psino;
  fansino2 = trecMemory->fansino2;
  xsino2 = trecMemory->xsino2;
  isino2 = trecMemory->isino2;
  psino2 = trecMemory->psino2;
  tmem = trecMemory->rbtmem;

minviews = trecParams->minviews;
  minviews1 = minviews + 2 * trecParams->nl;
  nl2 = 2 * trecParams->nl;
  nk2 = 2 * trecParams->nk;
  nbeta = trecParams->pviews * 2;
  ntheta = nbeta / 2;
  nsigma  = trecParams->nsamps;
  ns = trecParams->rwidth;
     /* if reverse we flip the sinogram.  Obviously this is not
        optimized, rather it's just something quick and dirty
        to allow us to have the capability. */ if (trecParams->reverse)
       for (ibeta = 0; ibeta < minviews1; ibeta++)
       {
         is = ibeta * nsigma;
         for (isigma = 0; isigma < nsigma / 2; isigma++)
         {
           accum = fansino[is + isigma];
           fansino[is + isigma] = fansino[is + nsigma - isigma - 1];
           fansino[is + nsigma - isigma - 1] = accum;
           if(trecParams->cb)
             {
               accum = fansino2[is + isigma];
               fansino2[is + isigma] = fansino2[is + nsigma - isigma - 1];
```

```
              fansino2[is + nsigma - isigma - 1] = accum;
        }
    }
  }

/* optionally do 2D clipping.  need tmem of length nsigma
   This used to be done at the end of rebinning.  But I think
   putting it at the beginning is better. */ clip2d(fansino, tmem, minviews1, nsigma, trecParams->clip2d);
if(trecParams->cb)
   clip2d(fansino2, tmem, minviews1, nsigma, trecParams->clip2d);

/* now do the initial rebinning: from (sigma, beta) to (theta, sigma) */ btot(fansino, xsino, trecTables->phi, minviews, nsigma, nl2);
if(trecParams->cb)
   btot(fansino2, xsino2, trecTables->phi, minviews, nsigma, nl2);

/* next fold the information in the corners into the area used for the
   final output parallel sinogram */
if (trecParams->dofold)
  {
   if(!trecParams->cb)
      foldinter(xsino, trecTables->nnbeta, trecParams);
   else
      foldintercb(xsino, xsino2, trecTables->nnbeta, trecParams);
  } if (saveinter) return(0);

/* Now do the final interpolation from (theta, sigma) to (s, theta)
   This goes from xsino to isino.  The rows and columns are
   exchanged again.
*/ stos(xsino, isino, trecTables, minviews, ns, nk2, ntheta);
if(trecParams->cb)
   stos(xsino2, isino2, trecTables, minviews, ns, nk2, ntheta);

/*
 * finally go from isino to psino.  This involves transposing the data
 * and rotating
 */ tandr(isino, psino, ns, ntheta, trecParams->rot, trecParams->rscale);
if(trecParams->cb)
   tandr(isino2, psino2, ns, ntheta, trecParams->rot, trecParams->rscale);

return (0);
 }

INT
   clip2d(fansino, tmem, minviews1, nsigma, rclip2d)
REAL32 *fansino;/* input sinogram */
REAL32 *tmem;  /* some temp memory of width nsigma */
REAL rclip2d;  /* clip factor, 0 means don't do anything */
INT minviews1, nsigma; /* length and width of sinogram */
{
 REAL32 clip2d, mclip2d, half = .5;
 INT ibeta, is;
 REAL32 *ca = salcache, *ca1 = salcache + 1024;

if(rclip2d <= 0.0) return(0);
 if(nsigma > 1024) return(-1);

clip2d = rclip2d;
 mclip2d = -clip2d;
 for (ibeta = 0; ibeta < minviews1; ibeta++)
    {
     is = ibeta * nsigma;
     tmem[0] = 2 * fansino[is];
     tmem[nsigma - 1] = 2 * fansino[is + nsigma - 1];
     vadd(fansino + is, 1, fansino + is + 2, 1, tmem + 1, 1, nsigma - 2);
```

```
#if CSPI
    tkclip2d(fansino + is, tmem, &mclip2d, &clip2d, &nsigma);
#else
    vsmulx(tmem, 1, &half, ca, 1, nsigma, SAL_NC);
    vsubx(ca, 1, fansino + is, 1, ca1, 1, nsigma, SAL_CNC);
    vclipx(ca1, 1, &mclip2d, &clip2d, ca1, 1, nsigma, SAL_CC);
    vaddx(ca, 1, ca1, 1, fansino + is, 1, nsigma, SAL_CCN);
#endif
   }
 return(0);
}

/* btot creates the intermediate sinogram (beta to theta).
   It starts with a nsamps x minviews + 2*nl fan beam sinogram. (sigma,beta)
   It results in a minviews x nsamps intermediate sinogram. (theta,sigma)
   Note that the sinogram has its rows and columns exchanged in this step.
   The 2*nl extra input rows are needed for the interpolation and disappear
   after this step.
*/
  INT
    btot(fansino, xsino, phi, minviews, nsigma, nl2)
       REAL32 *xsino, *fansino, *phi;
    INT minviews, nsigma, nl2;
{
  INT i, isigma, w;

w = minviews + nl2; /* width of the transposed matrix */

/* first transpose the input matrix */
  mtrans(fansino, 1, xsino, 1, nsigma, w);

/* convolve the rows with the phi function */ for(isigma = 0;isigma < nsigma;isigma++)
    {
     myconv(xsino + isigma * w, 1, phi + isigma * nl2, 1,
         xsino + isigma * minviews, 1, minviews, nl2);
    }
  return(0);
}

/*
 * foldinter folds the corners of the intermediate sinogram into the part
 * that gets used in the final result.
   For each sample isigma the points that are not in the final result are
   0 .. nnbeta[isigma] - 1 and
   nnbeta[isigma] + ntheta .. minviews - 1
 */
INT
foldinter(xsino, nnbeta, trecParams)
      TREC_PARAMS *trecParams;
      REAL32 *xsino;
      UINT16 *nnbeta;
{
 INT i, j, k, n, cfslim = 0, cfend, npviews = 1, cfblim = 0;
 INT minviews, ntheta, nsamps, nnb;
 REAL w, w1, w2, x1, x2, x, dsigma, dtheta;
 REAL32 *corner1, *corner2, *final1, *final2, zero = 0.0, half = .5;
 CHAR str[100];

ntheta = trecParams->pviews;
 nsamps = trecParams->nsamps;
 minviews = trecParams->minviews;
 dsigma = trecParams->fanang / (nsamps - 1);
 dtheta = PI / ntheta;

npviews = trecParams->npviews;
 cfslim = trecParams->cfslim;
 cfblim = trecParams->cfblim;

if(test)
    {
     while(1)
       {
        printf("Enter i:");gets(str);i = atoi(str);
        if(i < 0) break;
```

```
      printf("nnbeta[i]:%d, enter j:", nnbeta[i]);gets(str); j = atoi(str);
      w = weights(i, j - nnbeta[i], ntheta, nsamps, trecParams->fanang);
      k = nsamps - i - 1;/* this is -sigma */
      w1 = weights(k, minviews - j - nnbeta[k], ntheta, nsamps,
                   trecParams->fanang);
      corner1 = xsino + i * minviews;
      corner2 = xsino + k * minviews + minviews;

final1 = xsino + k * minviews + nnbeta[k] - nnbeta[i] + ntheta;
      final2 = corner1 - nnbeta[k] + nnbeta[i] + minviews - ntheta;
      printf("w:%g c1:%g f1:%g c2:%g f2:%g\n",
             w, corner1[j], final1[j], corner2[-j], final2[-j]);
    } printf("Enter npviews[%d]:",npviews);
    gets(str);
    if(strlen(str)) npviews = atoi(str);
    printf("Enter cfslim[%d]:",cfslim);
    gets(str);
    if(strlen(str)) cfslim = atoi(str);
    printf("Enter cfblim[%d]:",cfblim);
    gets(str);
    if(strlen(str)) cfblim = atoi(str);
  } if(trecParams->docf == 3) /* for cone beam zero out the corners */
  {
    for (i = 0; i < nsamps; i++)
      {
        nnb = nnbeta[i];
        if(nnb > 0) vfill(&zero, xsino + i * minviews, 1, nnb);
        n = minviews - nnb - ntheta;
        if(n > 0) vfill(&zero, xsino + i * minviews + nnb + ntheta, 1, n);
      }
  }
  if(trecParams->docf == 4) /* for cone beam zero out the center */
    {
      for (i = 0; i < nsamps; i++)
        vfill(&zero, xsino + i * minviews + nnbeta[i], 1, ntheta);
    } x1 = trecParams->fanang; /* x1 = fanang - is * dsigma */
  for (i = 0; i < nsamps; i++)
    {
      k = nsamps - i - 1;/* this is -sigma */
      nnb = nnbeta[i];
      /* at sample i first corner starts at 1, goes to nnbeta[i] - 1
         the first point (j=0) has a weight of 0 so can be ignored
      */
      corner1 = xsino + i * minviews;
      /* at sample k second corner starts at minviews - 1 goes to
         minviews - nnbeta[i] + 1, then last point is done separately,
         it always has a weight of .5
      */
      corner2 = xsino + k * minviews + minviews;

final1 = xsino + k * minviews + nnbeta[k] - nnb + ntheta;
      final2 = corner1 - nnbeta[k] + nnb + minviews - ntheta;
      if (i >= cfslim)
        cfend = 1;
      else
        cfend = (cfblim * (cfslim - i)) / cfslim;
      if (cfend < npviews)
        cfend = npviews;
      /* j must start at 1 for corner2 and final2 addresses to be ok */
      /* therefore always have npviews at least equal to 1 */
      /* all those points up to cfend are deemed to be corner filled, hence
         do not need to be folded */
      x2 = (cfend - nnb) * dtheta;
      for (j = cfend; j < nnb; j++)
        {
/*
          w = weights(i, j - nnb, ntheta, nsamps, trecParams->fanang);
*/
          x = (x2 + x1) / (2.0 * x1);
          if(x > 0.0)
            {
```

```
          w = x * x * (3.0 - 2.0 * x);
          if (w > 0.0)
            {
              final1[j] += w * (corner1[j] - final1[j]);
              final2[-j] += w * (corner2[-j] - final2[-j]);
/*
              final1[j] = corner1[j];
              final2[-j] = corner2[-j];
*/
            }
        }
      x2 += dtheta;
    }
    final2[-nnb] += .5 * (corner2[-nnb] - final2[-nnb]); /* w is always .5 */
    x1 -= dsigma;
  }
}

/* cone beam version of foldinter.
   has two sinograms to fold.  corner area of one gets mapped to other
*/
INT
foldintercb(xsino, xsino2, nnbeta, trecParams)
     TREC_PARAMS *trecParams;
     REAL32 *xsino, *xsino2;
     UINT16 *nnbeta;
{
INT i, j, k, n, cfslim = 0, cfend, npviews = 1, cfblim = 0;
INT minviews, ntheta, nsamps, nnb;
REAL w, w1, w2, x1, x2, x, dsigma, dtheta;
REAL32 *corner1, *corner2, *final1, *final2, *cor21, *cor22, *fin21, *fin22;
REAL32 zero = 0.0, half = .5;
CHAR str[100];

ntheta = trecParams->pviews;
  nsamps = trecParams->nsamps;
  minviews = trecParams->minviews;
  dsigma = trecParams->fanang / (nsamps - 1);
  dtheta = PI / ntheta;

npviews = trecParams->npviews;
  cfslim = trecParams->cfslim;
  cfblim = trecParams->cfblim;

x1 = trecParams->fanang; /* x1 = fanang - is * dsigma */
  for (i = 0; i < nsamps; i++)
  {
    k = nsamps - i - 1;/* this is -sigma */
    nnb = nnbeta[i];
    /* at sample i first corner starts at 1, goes to nnbeta[i] - 1
       the first point (j=0) has a weight of 0 so can be ignored
    */
    corner1 = xsino + i * minviews;
    cor21 = xsino2 + i * minviews;
    /* at sample k second corner starts at minviews - 1 goes to
       minviews - nnbeta[i] + 1, then last point is done separately,
       it always has a weight of .5
    */
    corner2 = xsino + k * minviews + minviews;
    cor22 = xsino2 + k * minviews + minviews;

final1 = xsino + k * minviews + nnbeta[k] - nnb + ntheta;
    final2 = corner1 - nnbeta[k] + nnb + minviews - ntheta;
    fin21 = xsino2 + k * minviews + nnbeta[k] - nnb + ntheta;
    fin22 = cor21 - nnbeta[k] + nnb + minviews - ntheta;
    if (i >= cfslim)
      cfend = 1;
    else
      cfend = (cfblim * (cfslim - i)) / cfslim;
    if (cfend < npviews)
      cfend = npviews;
    /* j must start at 1 for corner2 and final2 addresses to be ok */
    /* therefore always have npviews at least equal to 1 */
    /* all those points up to cfend are deemed to be corner filled, hence
       do not need to be folded */
    x2 = (cfend - nnb) * dtheta;
```

```c
      for (j = cfend; j < nnb; j++)
      {
       x = (x2 + x1) / (2.0 * x1);
       if(x > 0.0)
          {
            w = x * x * (3.0 - 2.0 * x);
            if (w > 0.0)
              {
                final1[j] += w * (cor21[j] - final1[j]);
                final2[-j] += w * (cor22[-j] - final2[-j]);
                fin21[j] += w * (corner1[j] - fin21[j]);
                fin22[-j] += w * (corner2[-j] - fin22[-j]);
              }
          }
       x2 += dtheta;
      }
      final2[-nnb] += .5 * (cor22[-nnb] - final2[-nnb]); /* w is always .5 */
      fin22[-nnb] += .5 * (corner2[-nnb] - fin22[-nnb]); /* w is always .5 */
      x1 -= dsigma;
    }
 }

/* stos: sigma to s interpolation.
    This takes an input sinogram (xsino) that has width minviews
    and produces an output sinogram of width ntheta and length ns,
    which is still transposed wrt the final output
*/
#ifndef CSPI
INT
   stos(xsino, isino, trecTables, minviews, ns, nk2, ntheta)
REAL32 *xsino; /* input sinogram, width is minviews */
REAL32 *isino; /* output sinogram, width is ntheta, length is ns */
TREC_TABLES *trecTables;
INT minviews, ns, nk2, ntheta;
{
 INT is, isigma, k;
 REAL32 *cache1 = salcache, coeff;

for (is = 0; is < ns; is++)
   {
     isigma = trecTables->nnsigma[is];

coeff = trecTables->psi[is];
       vsmulx(xsino + isigma * minviews + trecTables->nnbeta[isigma], 1,
              &coeff, cache1, 1, ntheta, SAL_NC);
       for (k = 1; k < nk2; k++)
       {
         coeff = trecTables->psi[k * ns + is];
         vsmax(xsino + (isigma + k) * minviews + trecTables->nnbeta[isigma + k],
               1, &coeff, cache1, 1, cache1, 1, ntheta, SAL_NCC);
       }
ifndef CSPI
       vmovx(cache1, 1, isino + is * ntheta, 1, ntheta, SAL_CN);
#else
       vmovx(cache1, 1, isino + is, ns, ntheta, SAL_CN);
#endif
    }
  return (0);
} else
define VSUMN 6
   stos(xsino, isino, trecTables, minviews, ns, nk2, ntheta)
REAL32 *xsino; /* input sinogram, width is minviews */
REAL32 *isino; /* output sinogram, width is ntheta, length is ns */
TREC_TABLES *trecTables;
INT minviews, ns, nk2, ntheta;
{
 INT is, isigma, k, k1;
 REAL32 *tmem = salcache, coeff;
 REAL32 *a0, *a1, *a2, *a3, *a4, *a5, *b0, *b1, *b2, *b3, *b4, *b5;

for (is = 0; is < ns; is++)
   {
     isigma = trecTables->nnsigma[is];
```

```
        vclr(tmem, 1, ntheta);
        for(k = 0; k <= nk2 - VSUMN; k+=VSUMN)
          {a0 = xsino + (isigma + k) * minviews + trecTables->nnbeta[isigma + k];
           a1 = xsino + (isigma + k + 1) * minviews +
              trecTables->nnbeta[isigma + k + 1];
           a2 = xsino + (isigma + k + 2) * minviews +
              trecTables->nnbeta[isigma + k + 2];
           a3 = xsino + (isigma + k + 3) * minviews +
              trecTables->nnbeta[isigma + k + 3];
           a4 = xsino + (isigma + k + 4) * minviews +
              trecTables->nnbeta[isigma + k + 4];
           a5 = xsino + (isigma + k + 5) * minviews +
              trecTables->nnbeta[isigma + k + 5];

b0 = &trecTables->psi[k * ns + is];
                b1 = &trecTables->psi[(k + 1) * ns + is];
                b2 = &trecTables->psi[(k + 2) * ns + is];
                b3 = &trecTables->psi[(k + 3) * ns + is];
                b4 = &trecTables->psi[(k + 4) * ns + is];
                b5 = &trecTables->psi[(k + 5) * ns + is];

#if VSUMN == 3
              tkvsum3(a0, a1, a2, b0, b1, b2, tmem, &ntheta);
#else
              tkvsum6(a0, a1, a2, a3, a4, a5, b0, b1, b2, b3, b4, b5, tmem, &ntheta);
endif if(k + VSUMN * 2 > nk2)    /* finish off any misc remaining */
                  for(k1 = k + VSUMN; k1 < nk2; k1++)
                    {
                     coeff = trecTables->psi[k1 * ns + is];
                     vsma(xsino + (isigma + k1) * minviews +
                          trecTables->nnbeta[isigma + k1],
                          1, &coeff, tmem, 1, tmem, 1, ntheta);
                    }
             }
           vmov(tmem, 1, isino + is, ns, ntheta);
         }
        return (0);
      } ifdef UNIX
INT
   tkvsum3(a0, a1, a2, b0, b1, b2, tmem, n)
REAL32 *a0, *a1, *a2, *b0, *b1, *b2;
REAL32 *tmem;
INT *n;
{
 vsma(a0, 1, b0, tmem, 1, tmem, 1, *n);
 vsma(a1, 1, b1, tmem, 1, tmem, 1, *n);
 vsma(a2, 1, b2, tmem, 1, tmem, 1, *n);
}
endif endif
if 0
INT
   stos(xsino, isino, trecTables, minviews, ns, nk2, ntheta)
REAL32 *xsino; /* input sinogram, width is minviews */
REAL32 *isino; /* output sinogram, width is ntheta, length is ns */
TREC_TABLES *trecTables;
INT minviews, ns, nk2, ntheta;
{
 INT is, isigma, k;
 REAL32 cache[2056], coeff;
 REAL32 rzero = 0.0, rone = 1.0;
 INT32 i1=1, flip = 0;
 INT32 d, n1;
 INT32 buf1=1, buf2=2, nbuf=2;

#define BUFFERSIZE (700)
 for (d = 0; d < ntheta; d += BUFFERSIZE)
  {
   n1 = ntheta - d;
   if(n1 > BUFFERSIZE) n1 = BUFFERSIZE;
   for (is = 0; is < ns; is++)
    {
```

```
    isigma = trecTables->nnsigma[is];

coeff = trecTables->psi[is];

vsmsa_sc_ (xsino + isigma * minviews + trecTables->nnbeta[isigma] + d,
               &i1, &coeff, &rzero, &buf1, &n1, &nbuf, cache);

for (k = 1; k < nk2; k++)
          {
            coeff = trecTables->psi[k * ns + is];
            vsmsa_sc_ (xsino + (isigma + k) * minviews +
                    trecTables->nnbeta[isigma + k] + d,
                    &i1, &coeff, &rzero, &buf2, &n1, &nbuf, cache);
            vadd_ccc_ (&buf1, &buf2, &buf1, &n1, &nbuf, cache);
/*
            flip = (flip + 1) & 1;
            if(flip)
            vsm2sa_scc_ (xsino + (isigma + k) * minviews +
                    trecTables->nnbeta[isigma + k] + d,
                    &i1, &coeff, &buf1, &rone, &rzero, &buf2, &n1, &nbuf, cache);
            else
            vsm2sa_scc_ (xsino + (isigma + k) * minviews +
                    trecTables->nnbeta[isigma + k]+d,
                    &i1, &coeff, &buf2, &rone, &rzero, &buf1, &n1, &nbuf, cache);
*/
          }
/*
      if(flip) vmov_cs_ (&buf2, isino + is + d * ns, &ns, &n1, &nbuf, cache);
      else vmov_cs_ (&buf1, isino + is + d * ns, &ns, &n1, &nbuf, cache);
*/
      vmov_cs_ (&buf1, isino + is + d * ns, &ns, &n1, &nbuf, cache);
        }
      }
   return (0);
}
endif /* tandr transpose and rotate the output sinogram.
   for CSPI the transpose does not speed things up so we eliminate it.
   A compilcation is that the sinogram is a 180 degree parallel sino.
   So a view at theta + 180 equals reverse of view at theta.
*/

INT
   tandr(isino, psino, ns, ntheta, rot, rscale)
REAL32 *isino, *psino;/* input, output */
INT ns, ntheta, rot;
REAL rscale;
   {
     INT rot1, itheta, k;
     REAL32 scale;

scale = rscale;
     /* rot can be larger than ntheta :
        ntheta represents a rotation of 180 deg
        */
     rot1 = rot % ntheta;

/* first transpose the views.
        It's fastest to do this using Mercury's routine
     */
#ifndef CSPI
     mtrans(isino, 1, psino, 1, ntheta, ns);
     vmov(psino, 1, isino, 1, ntheta * ns);
endif for (itheta = 0; itheta < ntheta; itheta++) /* itheta is the source view */
       {
         k = itheta - rot1; /* k is the destination view */
         if (k < 0)
           k += ntheta;
         /* see if the points in the view need to be reversed */
         if (((itheta < rot) && (rot < ntheta)) || ((itheta >= rot - ntheta) &&
             (rot >= ntheta)))
         {/* yes, reverse the view */
           if (scale == 1.0)
             vmov(isino + itheta * ns + (ns - 1), -1,
```

```
              psino + k * ns + 1, 1, ns - 1);
        else
          vsmul(isino + itheta * ns + (ns - 1), -1, &scale,
                psino + k * ns + 1, 1, ns - 1);
        psino[k * ns] = 0.0;
      } else
      {/* no, straight copy */
        if (scale == 1.0)
          vmov(isino + itheta * ns, 1, psino + k * ns, 1, ns);
        else
          vsmul(isino + itheta * ns, 1, &scale, psino + k * ns, 1, ns);
      }
    }
    return(0);
  }

/* calculate the weights for point in intermediate sinogram */
PRIVATE REAL
weights(is, it, ntheta, nsigma, fanang)
  INT is, it, ntheta, nsigma;
  REAL fanang;
{
  PRIVATE INT init = 1;
  PRIVATE REAL32 sigma0, dsigma, dtheta, const1, maxbeta, b0, fana;
  REAL32 sigma, beta, x, sigma2, w;

if (init)
  {
    sigma0 = -fanang / 2.0;
    dsigma = fanang / (nsigma - 1);
    dtheta = PI / ntheta;
    const1 = PI / 2.0 - fanang / 2.0;
    maxbeta = PI / 2.0 + fanang / 2.0;
    b0 = PI / 2.0;
    fana = fanang;
    init = 0;
  }
  sigma = is * dsigma + sigma0;
  beta = it * dtheta - sigma - b0;
  if(test) printf("beta:%g sigma:%g\n", beta, sigma);
  if (beta < 0.0)
  {
    beta = -beta;
    sigma = -sigma;
  }
  x = maxbeta - beta;
  if (x <= 0.0)
    return (0.0);
  sigma2 = 2.0 * sigma;
  if(test) printf("beta:%g const1-sigma2:%g\n", beta, const1- sigma2);
  if (beta <= const1 - sigma2)
    return (1.0);

x = x / (fana + sigma2);
  w = x * x * (3.0 - 2.0 * x);
  if(test) printf("x:%g w:%g\n", x, w);
/*
      (fana + it * dtheta - is * dsigma) / (2.0 * (fana - is * dsigma)));
*/ return(w);

}

/* an add hoc routine to clean out some garbage in corner fill area */
EXPORT INT
clean_dead(sino, nl, nviews, nsamps, docf)
REAL32 *sino;
INT nl, nviews, nsamps, docf;
{
 INT v, s, v0;
 if(docf == 1) /* 100ms */
 {
```

```
    v0 = 167 + n1;
    for(s=0;s<48;s+=6,v0-=2)
     for(v=v0;v>v0-15;v--)
         vclr(sino+v * nsamps + s, 1, 6);
    v0 = 734 + n1;
    for(s=816;s<nsamps;s+=6,v0-=2)
     for(v=v0;v>v0+15;v++)
         vclr(sino+v * nsamps + s, 1, 6);
  } return(0);

} ifndef CSPI
/* I have had problems with mercury's convolution routine.  Here is
   my own.  It seems to go faster than mercury's.  The speedup
   provided by the esal routines (verses sal in myconv)is .25 sec
   (1.10 vs 1.35).
*/ myconv(a,i,b,j,c,k,n,p)
REAL32 *a, *b, *c;
INT32 i, j, k, n, p;
{
   INT u,v;

vsmulx(a,i,b,salcache,1,n,SAL_NC);
   for(v=1;v<p;v++)
     vsmax(a + v, i, b + v * j, salcache, 1, salcache, 1, n,SAL_NCC);

vmovx(salcache, 1, c, k, n,SAL_CN);
} else myconv(a,i,b,j,c,k,n,p)
REAL32 *a, *b, *c;
INT32 i, j, k, n, p;
{
   INT u,v;
   REAL accum;

REAL32 zero = 0.0, one = 1.0;
   INT32 buf1 = 1;
   INT32 buf2 = 2;
   INT32 nbuf = 2;
   STATIC REAL32 cache[2056];
   INT32 n1, d, flip = 0;
   if((i == 1) && (p == 6))
      {tkconv6(a, b, b + 1, b + 2, b + 3, b + 4, b + 5, c, &k, &n);
       return(0);
      }
#define BUFFERSIZE (700)
   for (d=0; d < n; d+=BUFFERSIZE)
   {
    n1 = n - d;

if(n1 > BUFFERSIZE) n1 = BUFFERSIZE;

vsmsa_sc_ (a + (d * i), &i, b, &zero, &buf2, &n1, &nbuf, cache);
     for (v = 1; v < p;v++)
        {
        vsmsa_sc_ (a + v + (d * i), &i, b + v * j, &zero,
                   &buf1, &n1, &nbuf, cache);
        vadd_ccc_ (&buf1, &buf2, &buf2, &n1, &nbuf, cache);
/*
        flip = (flip + 1) & 1;
        if(flip)
          vsm2sa_scc_ (a + v + (d * i), &i, b + v * j, &buf2, &one, &zero,
                       &buf1, &n1, &nbuf, cache);
        else
          vsm2sa_scc_ (a + v + (d * i), &i, b + v * j, &buf1, &one, &zero,
                       &buf2, &n1, &nbuf, cache);
```

```
*/
  }
/*
  if(flip) vmov_cs_ (&buf1, c + (d * k), &k, &n1, &nbuf, cache);

else vmov_cs_ (&buf2, c + (d * k), &k, &n1, &nbuf, cache);
*/
  vmov_cs_ (&buf2, c + (d * k), &k, &n1, &nbuf, cache);
  }
 }
endif if 0 define TSIZE 16384
define WINC 32

/* this is not quite as fast as mtrans */
mymtrans(a,i,c,k,m,n)

REAL32  *a, *c;
INT32   i, k, m, n;

{
 INT w, wi, rinc, r, ri, t;
 PRIVATE REAL32 temp[TSIZE];

if((i != 1) || (k != 1))
   {
     for(w = 0; w < m; w++)
       vmov(a + i * w, i * m, c + k * n * w, k, n);
     return;
   } for(w = 0; w < m; w += WINC)
   {
     wi = m - w;
     if(wi > WINC) wi = WINC;
     if(wi == 1)
       vmov(a + w, m, c + n * w, 1, n);
     else
       {
         rinc = TSIZE / wi;
         if(rinc > n) rinc = n;
         for(r = 0;r < n;r += rinc)
           {
             ri = n - r;
             if(ri > rinc) ri = rinc;
             for(t = 0;t < rinc; t++)
               vmov(a + (r + t) * m + w, 1, temp + t * wi, 1, wi);
             for(t = 0;t < wi;t++)
               vmov(temp + t, wi, c + (w + t) * n + r, 1, ri);
           }
       }

}
}
endif
/******************** End Of trecRebin.c ********************/
```

What is claimed is:

1. A computer-implemented method for correcting cone beam error in an image reconstructed from data in a sinogram acquired from a fan beam computer tomography X-ray system, the method comprising the following steps:

(a) rebinning fan beam data acquired from said system into parallel beam format, said step of rebinning including the steps of:

(1) performing a first one-dimensional interpolation of columns in said fan beam data sinogram to generate an intermediate sinogram having a rectangular portion that includes non-redundant X-ray data and having first and second corner portions that include redundant X-ray data;

(2) weighting said redundant data in said intermediate sinogram such that a sum of a redundant X-ray weight plus a central X-ray weight is unity, wherein said redundant data are folded over into said rectangular portion such that said weighted central X-ray plus said weighted redundant X-ray replaces said central X-ray value in said intermediate sinogram;

(3) performing a second one-dimensional interpolation of rows in said intermediate sinogram, wherein said fan beam data are now represented in a parallel beam sinogram that includes said redundant data folded into said rectangular portion; and (b) reconstructing data acquired by said fan beam CT system, said step of reconstructing including the steps of:

(1) filtering with a parallel beam kernel said parallel beam sinogram data for each view therein;

(2) circularly shifting data resulting from said step 1(b)(1);

(3) transforming data resulting from said step 1(b)(2);

(4) replicating data resulting from said step 1(b)(3);

(5) multiplying by an interpolation filter data resulting from said step 1(b)(4);

(6) using a gridding function, gridding data resulting from said step 1(b)(5) into a Fourier image at an angle corresponding to the view angle;

(7) convolving each view in said step 1(b)(6) with the transform of a cone beam weight function by multiplying by each non-zero coefficient of the weight function and gridding at an offset from the view angle into a Fourier image;

(8) repeating steps (b)(1) through (b)(7) for each said view;

(9) forming a preliminary image by taking a two-dimensional inverse Fourier transform of said views;

(10) extracting a center portion of said preliminary image;

(11) forming a reconstructed image by multiplying said preliminary image with its center portion extracted by an inverse of the transform of said gridding function;

wherein said reconstructed image is substantially free of cone beam error.

2. The method of claim 1, wherein at step 1(a)(2), said step of weighting is accomplished using short scan fan beam reconstruction weights.

3. For use with a parallel beam procedure that corrects cone beam error in an image reconstructed from data in a sinogram acquired from a fan beam computer tomography X-ray system, a computer-implemented method for rebinning said data in said sinogram into parallel beam format, the method comprising the following steps:

(a) performing a first one-dimensional interpolation of columns of the fan beam data sinogram to generate an intermediate sinogram having a rectangular portion that includes non-redundant data, and having first and second corner portions that include redundant data;

(b) weighting said redundant data in said intermediate sinogram such that a sum of a redundant X-ray weight plus a central X-ray weight is unity, wherein said redundant data are folded over into said rectangular portion such that said weighted central X-ray plus said weighted redundant X-ray replaces said central X-ray value; said intermediate sinogram; and (c) performing a second one-dimensional interpolation of rows in said intermediate sinogram, wherein said fan beam data are now represented in a parallel beam sinogram that includes said redundant data folded into said rectangular portion.

4. The method of claim 3, wherein at step 3(b), said step of weighting is accomplished using short scan fan beam reconstruction weights.

5. A computer-implemented for reducing cone beam error in reconstructing an image from data acquired from a fan beam computer tomography X-ray system and rebinned into parallel beam sinogram, the method including the following steps:

(a) filtering with a parallel beam kernel said parallel beam sinogram data for each view therein;

(b) circularly shifting data resulting from said step 5(a);

(c) transforming data resulting from said step 5(b);

(d) replicating data resulting from said step 5(c);

(e) multiplying by an interpolation filter data resulting from said step 5(d);

(f) using a gridding function, gridding data resulting from said step 5(e) into a Fourier image at an angle corresponding to the view angle;

(g) convolving each view in step 5(f) with the transform of a cone beam weight function by multiplying by each non-zero coefficient of the weight function and gridding at an offset from the view angle into a Fourier image;

(h) repeating said steps (a) through (g) for each view;

(i) forming a preliminary image by taking a two-dimensional inverse Fourier transform of said views;

(j) extracting a center portion of said preliminary image;

(k) forming a reconstructed image by multiplying said preliminary image with its center portion extracted by an inverse of the transform of said gridding function;

wherein said reconstructed image is substantially free of cone beam error.

6. An apparatus for correcting cone beam error in an image reconstructed from data in a sinogram acquired from a fan beam computer tomography X-ray system, the apparatus comprising:

(a) means for rebinning fan beam data acquired from said system into parallel beam format, said means for rebinning including:

(1) means for performing a first one-dimensional interpolation of columns of the fan beam data sinogram to generate an intermediate sinogram having a rectangular portion that includes non-redundant data, and having first and second corner portions that include redundant data;

(2) means for weighting said redundant data such that a sum of a redundant ray weight plus a central ray weight is unity, wherein said redundant data are folded over into said rectangular portion of said intermediate sinogram such that a sum of said weighted central ray plus said weighted redundant ray replaces said central ray value in said intermediate sinogram;

(3) means for performing a second one-dimensional interpolation of rows in said intermediate sinogram, wherein said fan beam data are now represented in a parallel beam sinogram that includes said redundant data folded into said rectangular portion; and (b) means for reconstructing views acquired by said fan beam CT system, said means for reconstructing including:
  (1) means for filtering with a parallel beam kernel said parallel beam sinogram for each view therein;
  (2) means for circularly shifting output data from said means for filtering;
  (3) means for transforming output data from said means for circularly shifting;
  (4) means for replicating output data from said means for transforming;
  (5) means for multiplying by an interpolation filter output data from said means for replicating;
  (6) gridding function means for gridding output data from said means for multiplying into a Fourier image at an angle corresponding to the view angle;
  (8) means for convolving each view in output data provided by said gridding function means with the transform of a cone beam weight function by multiplying by each non-zero coefficient of the weight function and gridding at an offset from the view angle into a Fourier image;
  (9) means for subjecting each such view to said means described in (b)(1) through (b)(4);
  (10) means for forming a preliminary image by taking a two-dimensional inverse Fourier transform of said views;
  (11) means for extracting a center portion of said preliminary image;
  (12) means for forming a reconstructed image by multiplying said preliminary image with its center portion extracted by an inverse of the transform of said gridding function;

wherein said reconstructed image is substantially free of cone beam error.

* * * * *